US008721681B2

(12) United States Patent
Ruff et al.

(10) Patent No.: US 8,721,681 B2
(45) Date of Patent: *May 13, 2014

(54) BARBED SUTURE IN COMBINATION WITH SURGICAL NEEDLE

(75) Inventors: Gregory L. Ruff, Chapel Hill, NC (US); Matthew A. Megaro, Chapel Hill, NC (US); Jeffrey C. Leung, Raleigh, NC (US)

(73) Assignee: Ethicon, Inc., Somerville, NJ (US)

( * ) Notice: Subject to any disclaimer, the term of this patent is extended or adjusted under 35 U.S.C. 154(b) by 104 days.

This patent is subject to a terminal disclaimer.

(21) Appl. No.: 12/495,497

(22) Filed: Jun. 30, 2009

(65) Prior Publication Data
US 2010/0087855 A1    Apr. 8, 2010

Related U.S. Application Data

(63) Continuation of application No. 11/307,901, filed on Feb. 27, 2006, now abandoned, which is a continuation of application No. 10/065,278, filed on Sep. 30, 2002, now abandoned.

(51) Int. Cl.
*A61B 17/04* (2006.01)
(52) U.S. Cl.
USPC .......................................... 606/228
(58) Field of Classification Search
USPC ............... 606/225, 228–231; 24/445
See application file for complete search history.

(56) References Cited

U.S. PATENT DOCUMENTS

| 709,392 | A | 9/1902 | Brown |
|---|---|---|---|
| 733,723 | A | 7/1903 | Lukens |
| 789,401 | A | 5/1905 | Acheson |
| 816,026 | A | 3/1906 | Meier |
| 879,758 | A | 2/1908 | Foster |
| 1,142,510 | A | 6/1915 | Engle |
| 1,248,825 | A | 12/1917 | Dederer |
| 1,321,011 | A | 11/1919 | Cottes |
| 1,558,037 | A | 10/1925 | Morton |
| 1,728,316 | A | 9/1929 | Wachenfeldt |
| 1,886,721 | A | 11/1932 | O'Brien |
| 2,094,578 | A | 10/1937 | Blumenthal |

(Continued)

FOREIGN PATENT DOCUMENTS

| BE | 1014364 | 9/2003 |
|---|---|---|
| CA | 2309844 | 12/1996 |

(Continued)

OTHER PUBLICATIONS

International Search Report for PCT/US2007/074658 dated Jun. 12, 2007, 3 pages.

(Continued)

*Primary Examiner* — Julian Woo

(57) ABSTRACT

A barbed suture for connecting tissue, and a combination surgical needle with a barbed suture. The suture includes an elongated body and a plurality of barbs projecting from the body. Each barb causes the suture to resist movement in an opposite direction from which the barb faces. The disposition of the barbs on the body may be staggered, twist cut multiple spiral, overlapping, or random. Also, the configuration of the barbs may be a certain spirality angle α, barb cut angle θ, barb cut depth, barb cut length, barb cut distance, corrugated barb underside, arcuate barb base, or varying barb size.

19 Claims, 11 Drawing Sheets

(56) References Cited

U.S. PATENT DOCUMENTS

| | | | |
|---|---|---|---|
| 2,201,610 A | 5/1940 | Dawson, Jr. | |
| 2,232,142 A | 2/1941 | Schumann | |
| 2,254,620 A | 9/1941 | Miller | |
| 2,347,956 A | 5/1944 | Lansing | |
| 2,355,907 A | 8/1944 | Cox | |
| 2,421,193 A | 5/1947 | Gardner | |
| 2,452,734 A | 11/1948 | Costelow | |
| 2,472,009 A | 5/1949 | Gardner | |
| 2,480,271 A | 8/1949 | Sumner | |
| 2,572,936 A | 10/1951 | Kulp | |
| 2,684,070 A | 7/1954 | Kelsey | |
| 2,779,083 A | 1/1957 | Eaton | |
| 2,814,296 A | 11/1957 | Everett | |
| 2,817,339 A | 12/1957 | Sullivan | |
| 2,866,256 A | 12/1958 | Matlin | |
| 2,910,067 A | 10/1959 | White | |
| 2,928,395 A | 3/1960 | Forbes et al. | |
| 2,988,028 A | 6/1961 | Alcamo | |
| 3,003,155 A | 10/1961 | Mielzynski | |
| 3,066,452 A | 12/1962 | Bott et al. | |
| 3,066,673 A | 12/1962 | Bott et al. | |
| 3,068,869 A | 12/1962 | Shelden | |
| 3,068,870 A | 12/1962 | Levin | |
| 3,123,077 A | 3/1964 | Alcamo | |
| 3,166,072 A | 1/1965 | Sullivan | |
| 3,187,752 A | 6/1965 | Glick | |
| 3,206,018 A | 9/1965 | Lewis | |
| 3,209,652 A | 10/1965 | Burgsmueller | |
| 3,209,754 A | 10/1965 | Brown | |
| 3,212,187 A | 10/1965 | Benedict | |
| 3,214,810 A | 11/1965 | Mathison | |
| 3,221,746 A | 12/1965 | Noble | |
| 3,234,636 A | 2/1966 | Brown | |
| 3,273,562 A | 9/1966 | Brown | |
| 3,352,191 A | 11/1967 | Crawford | |
| 3,378,010 A | 4/1968 | Codling | |
| 3,385,299 A | 5/1968 | Le Roy | |
| 3,394,704 A | 7/1968 | Dery | |
| 3,494,006 A | 2/1970 | Brumlik | |
| 3,522,637 A | 8/1970 | Brumlik | |
| 3,525,340 A | 8/1970 | Gilbert | |
| 3,527,223 A | 9/1970 | Shein | |
| 3,545,608 A | 12/1970 | Berger | |
| 3,557,795 A | 1/1971 | Hirsch | |
| 3,570,497 A | 3/1971 | Lemole | |
| 3,586,002 A | 6/1971 | Wood | |
| 3,608,095 A | 9/1971 | Barry | |
| 3,608,539 A | 9/1971 | Miller | |
| 3,618,447 A | 11/1971 | Goins | |
| 3,646,615 A | 3/1972 | Ness | |
| 3,683,926 A | 8/1972 | Suzuki | |
| 3,700,433 A | 10/1972 | Duhl | |
| 3,716,058 A | 2/1973 | Tanner, Jr. | |
| 3,720,055 A | 3/1973 | deMestral | |
| 3,748,701 A * | 7/1973 | De Mestral | 24/445 |
| 3,762,418 A | 10/1973 | Wasson | |
| 3,825,010 A | 7/1974 | McDonald | |
| 3,833,972 A | 9/1974 | Brumlik | |
| 3,845,641 A | 11/1974 | Waller | |
| 3,847,156 A | 11/1974 | Trumble | |
| 3,889,322 A | 6/1975 | Brumlik | |
| 3,918,455 A * | 11/1975 | Coplan | 606/225 |
| 3,941,164 A | 3/1976 | Musgrave | |
| 3,951,261 A | 4/1976 | Mandel | |
| 3,963,031 A | 6/1976 | Hunter | |
| 3,977,937 A | 8/1976 | Candor | |
| 3,980,177 A | 9/1976 | McGregor | |
| 3,981,051 A | 9/1976 | Brumlik | |
| 3,981,307 A | 9/1976 | Borysko | |
| 3,985,138 A | 10/1976 | Jarvik | |
| 3,985,227 A | 10/1976 | Thyen | |
| 3,990,144 A | 11/1976 | Schwartz | |
| 4,006,747 A | 2/1977 | Kronenthal | |
| 4,008,303 A | 2/1977 | Glick | |
| 4,027,608 A | 6/1977 | Arbuckle | |
| 4,043,344 A | 8/1977 | Landi | |
| D246,911 S | 1/1978 | Bess, Jr. | |
| 4,069,825 A | 1/1978 | Akiyama | |
| 4,073,298 A | 2/1978 | Le Roy | |
| 4,137,921 A | 2/1979 | Okuzumi | |
| 4,182,340 A | 1/1980 | Spencer | |
| 4,186,239 A | 1/1980 | Mize et al. | |
| 4,198,734 A | 4/1980 | Brumlik | |
| 4,204,541 A | 5/1980 | Kapitanov | |
| 4,204,542 A | 5/1980 | Bokros | |
| 4,259,959 A | 4/1981 | Walker | |
| 4,278,374 A | 7/1981 | Wolosianski | |
| 4,300,424 A | 11/1981 | Flinn | |
| 4,311,002 A | 1/1982 | Hoffmann et al. | |
| 4,313,448 A | 2/1982 | Stokes | |
| 4,316,469 A | 2/1982 | Kapitanov | |
| 4,317,451 A | 3/1982 | Cerwin | |
| 4,372,293 A | 2/1983 | Vijil-Rosales | |
| 4,428,376 A | 1/1984 | Mericle | |
| 4,430,998 A | 2/1984 | Harvey | |
| 4,434,796 A | 3/1984 | Karapetian | |
| 4,449,298 A | 5/1984 | Patz | |
| 4,454,875 A | 6/1984 | Pratt | |
| 4,467,805 A | 8/1984 | Fukuda | |
| 4,490,326 A | 12/1984 | Beroff et al. | |
| 4,492,075 A | 1/1985 | Faure | |
| 4,493,323 A | 1/1985 | Albright | |
| 4,505,274 A | 3/1985 | Speelman | |
| 4,510,934 A | 4/1985 | Batra | |
| 4,531,522 A | 7/1985 | Bedi | |
| 4,532,926 A | 8/1985 | O'Holla | |
| 4,535,772 A | 8/1985 | Sheehan | |
| 4,548,202 A | 10/1985 | Duncan | |
| 4,553,544 A | 11/1985 | Nomoto | |
| 4,610,250 A | 9/1986 | Green | |
| 4,610,251 A | 9/1986 | Kumar | |
| 4,635,637 A | 1/1987 | Schreiber | |
| 4,637,380 A | 1/1987 | Orejola | |
| 4,653,486 A | 3/1987 | Coker | |
| 4,669,473 A | 6/1987 | Richards | |
| 4,676,245 A | 6/1987 | Fukuda | |
| 4,689,882 A | 9/1987 | Lorenz | |
| 4,702,250 A | 10/1987 | Ovil et al. | |
| 4,719,917 A | 1/1988 | Barrows | |
| 4,741,330 A | 5/1988 | Hayhurst | |
| 4,750,910 A | 6/1988 | Takayanagi | |
| 4,751,621 A | 6/1988 | Jenkins | |
| 4,776,337 A | 10/1988 | Palmaz | |
| 4,832,025 A | 5/1989 | Coates | |
| 4,841,960 A | 6/1989 | Garner | |
| 4,865,026 A | 9/1989 | Barrett | |
| 4,873,976 A | 10/1989 | Schreiber | |
| 4,887,601 A | 12/1989 | Richards | |
| 4,895,148 A | 1/1990 | Bays | |
| 4,898,156 A | 2/1990 | Gatturna | |
| 4,899,743 A | 2/1990 | Nicholson | |
| 4,900,605 A | 2/1990 | Thorgersen | |
| 4,905,367 A | 3/1990 | Pinchuk | |
| 4,930,945 A | 6/1990 | Arai | |
| 4,932,962 A | 6/1990 | Yoon | |
| 4,946,468 A | 8/1990 | Li | |
| 4,948,444 A | 8/1990 | Schutz | |
| 4,950,258 A | 8/1990 | Kawai | |
| 4,950,285 A | 8/1990 | Wilk | |
| 4,968,315 A | 11/1990 | Gatturna | |
| 4,976,715 A | 12/1990 | Bays | |
| 4,979,956 A | 12/1990 | Silvestrini | |
| 4,981,149 A | 1/1991 | Yoon | |
| 4,994,073 A | 2/1991 | Green | |
| 4,994,084 A | 2/1991 | Brennan | |
| 4,997,439 A | 3/1991 | Chen | |
| 5,002,550 A | 3/1991 | Li | |
| 5,002,562 A | 3/1991 | Oberlander | |
| 5,007,921 A | 4/1991 | Brown | |
| 5,007,922 A | 4/1991 | Chen | |
| 5,026,390 A | 6/1991 | Brown | |
| 5,037,422 A | 8/1991 | Hayhurst | |
| 5,037,433 A | 8/1991 | Wilk et al. | |
| 5,041,129 A | 8/1991 | Hayhurst | |

(56) References Cited

U.S. PATENT DOCUMENTS

| | | |
|---|---|---|
| 5,046,513 A | 9/1991 | Gatturna |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,101,968 A | 4/1992 | Henderson |
| 5,102,418 A | 4/1992 | Granger |
| 5,102,421 A | 4/1992 | Anspach, Jr. |
| 5,103,073 A | 4/1992 | Danilov |
| 5,112,344 A | 5/1992 | Petros |
| 5,123,911 A | 6/1992 | Granger |
| 5,123,913 A | 6/1992 | Wilk |
| 5,123,919 A | 6/1992 | Sauter |
| 5,127,413 A | 7/1992 | Ebert |
| 5,133,738 A | 7/1992 | Korthoff |
| 5,141,520 A | 8/1992 | Goble |
| 5,147,382 A | 9/1992 | Gertzman |
| 5,156,615 A | 10/1992 | Korthoff et al. |
| 5,156,788 A | 10/1992 | Chesterfield |
| 5,176,692 A | 1/1993 | Wilk |
| 5,179,964 A | 1/1993 | Cook |
| 5,192,274 A | 3/1993 | Bierman |
| 5,192,302 A | 3/1993 | Kensey |
| 5,192,303 A | 3/1993 | Gatturna |
| 5,197,597 A | 3/1993 | Leary |
| 5,207,679 A | 5/1993 | Li |
| 5,207,694 A | 5/1993 | Broome |
| 5,217,486 A | 6/1993 | Rice |
| 5,217,494 A | 6/1993 | Coggins |
| 5,222,508 A | 6/1993 | Contarini |
| 5,222,976 A | 6/1993 | Yoon |
| 5,224,946 A | 7/1993 | Hayhurst |
| 5,234,006 A | 8/1993 | Eaton et al. |
| 5,242,457 A | 9/1993 | Akopov |
| 5,246,441 A | 9/1993 | Ross |
| 5,249,673 A | 10/1993 | Sinn |
| 5,258,013 A | 11/1993 | Granger |
| 5,263,973 A | 11/1993 | Cook |
| 5,269,783 A | 12/1993 | Sander |
| 5,282,832 A | 2/1994 | Toso |
| 5,292,326 A | 3/1994 | Green |
| 5,306,288 A | 4/1994 | Granger |
| 5,306,290 A | 4/1994 | Martins |
| 5,312,422 A | 5/1994 | Trott |
| 5,320,629 A | 6/1994 | Noda et al. |
| 5,330,488 A | 7/1994 | Goldrath |
| 5,330,503 A | 7/1994 | Yoon |
| 5,336,239 A | 8/1994 | Gimpelson |
| 5,341,922 A | 8/1994 | Cerwin |
| 5,342,376 A | 8/1994 | Ruff |
| 5,342,395 A | 8/1994 | Jarrett |
| 5,350,385 A | 9/1994 | Christy |
| 5,352,515 A | 10/1994 | Jarrett |
| 5,354,271 A | 10/1994 | Voda |
| 5,354,298 A | 10/1994 | Lee |
| 5,358,511 A | 10/1994 | Gatturna |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield |
| 5,380,334 A | 1/1995 | Torrie |
| 5,391,173 A | 2/1995 | Wilk |
| 5,395,126 A | 3/1995 | Tresslar |
| 5,403,346 A | 4/1995 | Loeser |
| 5,411,523 A | 5/1995 | Goble |
| 5,414,988 A | 5/1995 | Di Palma |
| 5,417,691 A | 5/1995 | Hayhurst |
| 5,425,746 A | 6/1995 | Proto |
| 5,425,747 A | 6/1995 | Brotz |
| 5,437,680 A | 8/1995 | Yoon |
| 5,450,860 A | 9/1995 | O'Connor |
| 5,451,461 A | 9/1995 | Broyer |
| 5,462,561 A | 10/1995 | Voda |
| 5,464,422 A | 11/1995 | Silverman |
| 5,464,426 A | 11/1995 | Bonutti |
| 5,464,427 A | 11/1995 | Curtis |
| 5,472,452 A | 12/1995 | Trott |
| 5,478,353 A | 12/1995 | Yoon |
| 5,480,403 A | 1/1996 | Lee |
| 5,480,411 A | 1/1996 | Liu |
| 5,484,451 A | 1/1996 | Akopov |
| 5,486,197 A | 1/1996 | Le |
| 5,494,154 A | 2/1996 | Ainsworth |
| 5,500,000 A | 3/1996 | Feagin |
| 5,500,991 A | 3/1996 | Demarest |
| 5,520,084 A | 5/1996 | Chesterfield |
| 5,520,691 A | 5/1996 | Branch |
| 5,522,845 A | 6/1996 | Wenstrom, Jr. |
| 5,527,342 A | 6/1996 | Pietrzak et al. |
| 5,531,760 A | 7/1996 | Alwafaie |
| 5,531,761 A | 7/1996 | Yoon |
| 5,531,790 A | 7/1996 | Frechet |
| 5,533,982 A | 7/1996 | Rizk |
| 5,536,582 A | 7/1996 | Prasad |
| 5,540,705 A | 7/1996 | Meade |
| 5,540,718 A | 7/1996 | Bartlett |
| 5,545,148 A | 8/1996 | Wurster |
| 5,546,957 A | 8/1996 | Heske |
| 5,549,631 A | 8/1996 | Bonutti |
| 5,554,171 A | 9/1996 | Gatturna |
| 5,566,822 A | 10/1996 | Scanlon |
| 5,569,272 A | 10/1996 | Reed et al. |
| 5,571,139 A | 11/1996 | Jenkins, Jr. |
| 5,571,175 A | 11/1996 | Vanney |
| 5,571,216 A | 11/1996 | Anderson |
| 5,573,543 A | 11/1996 | Akopov |
| 5,584,859 A | 12/1996 | Brotz |
| 5,601,557 A | 2/1997 | Hayhurst |
| 5,626,590 A | 5/1997 | Wilk |
| 5,626,611 A | 5/1997 | Liu et al. |
| 5,632,753 A | 5/1997 | Loeser |
| 5,643,288 A | 7/1997 | Thompson |
| 5,643,295 A | 7/1997 | Yoon |
| 5,643,319 A | 7/1997 | Green |
| 5,645,568 A | 7/1997 | Chervitz et al. |
| 5,647,874 A | 7/1997 | Hayhurst |
| 5,649,939 A | 7/1997 | Reddick |
| 5,653,716 A | 8/1997 | Malo |
| 5,662,714 A | 9/1997 | Charvin |
| 5,669,935 A | 9/1997 | Rosenman |
| 5,676,675 A | 10/1997 | Grice |
| D386,583 S | 11/1997 | Ferragamo |
| 5,683,417 A | 11/1997 | Cooper |
| D387,161 S | 12/1997 | Ferragamo et al. |
| 5,693,072 A | 12/1997 | McIntosh |
| 5,695,879 A | 12/1997 | Goldmann et al. |
| 5,697,976 A | 12/1997 | Chesterfield |
| 5,702,397 A | 12/1997 | Goble et al. |
| 5,702,462 A | 12/1997 | Oberlander |
| 5,709,692 A | 1/1998 | Mollenauer |
| 5,716,358 A | 2/1998 | Ochoa |
| 5,716,376 A | 2/1998 | Roby |
| 5,722,991 A | 3/1998 | Colligan |
| 5,723,008 A | 3/1998 | Gordon |
| 5,725,557 A | 3/1998 | Gatturna |
| 5,728,114 A | 3/1998 | Evans |
| 5,741,277 A | 4/1998 | Gordon |
| 5,763,411 A | 6/1998 | Edwardson |
| 5,765,560 A | 6/1998 | Verkerke |
| 5,766,246 A | 6/1998 | Mulhauser et al. |
| 5,779,719 A | 7/1998 | Klein |
| 5,782,864 A | 7/1998 | Lizardi |
| 5,807,403 A | 9/1998 | Beyar |
| 5,807,406 A | 9/1998 | Brauker |
| 5,810,853 A | 9/1998 | Yoon |
| 5,814,051 A | 9/1998 | Wenstrom, Jr. |
| 5,843,087 A | 12/1998 | Jensen |
| 5,843,178 A | 12/1998 | Vanney |
| 5,855,619 A | 1/1999 | Caplan et al. |
| 5,863,360 A | 1/1999 | Wood |
| 5,884,859 A | 3/1999 | Ma |
| 5,887,594 A | 3/1999 | LoCicero, III |
| 5,891,166 A | 4/1999 | Schervinsky |
| 5,893,856 A | 4/1999 | Jacob |

(56) References Cited

U.S. PATENT DOCUMENTS

| | | |
|---|---|---|
| 5,895,395 A | 4/1999 | Yeung |
| 5,895,413 A | 4/1999 | Nordstrom |
| 5,897,572 A | 4/1999 | Schulsinger |
| 5,899,911 A | 5/1999 | Carter |
| 5,916,224 A | 6/1999 | Esplin |
| 5,919,234 A | 7/1999 | Lemperle |
| 5,921,982 A | 7/1999 | Lesh |
| 5,925,078 A | 7/1999 | Anderson |
| 5,931,855 A | 8/1999 | Buncke |
| 5,935,138 A | 8/1999 | McJames, II |
| 5,938,668 A | 8/1999 | Scirica |
| 5,941,899 A | 8/1999 | Granger et al. |
| 5,950,633 A | 9/1999 | Lynch |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet |
| 5,972,024 A | 10/1999 | Northrup, III |
| 5,984,933 A | 11/1999 | Yoon |
| 5,993,459 A | 11/1999 | Larsen |
| 6,001,111 A | 12/1999 | Sepetka |
| 6,012,216 A | 1/2000 | Esteves |
| 6,015,410 A | 1/2000 | Tormala |
| 6,024,757 A | 2/2000 | Hase |
| 6,027,523 A | 2/2000 | Schmieding |
| 6,039,741 A | 3/2000 | Meislin |
| 6,056,778 A | 5/2000 | Grafton |
| 6,063,105 A | 5/2000 | Totakura |
| 6,071,292 A | 6/2000 | Makower et al. |
| 6,074,419 A | 6/2000 | Healy |
| 6,076,255 A | 6/2000 | Shikakubo |
| 6,083,244 A | 7/2000 | Lubbers |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| 6,129,741 A | 10/2000 | Wurster et al. |
| D433,753 S | 11/2000 | Weiss |
| 6,146,406 A | 11/2000 | Shluzas |
| 6,146,407 A | 11/2000 | Krebs |
| 6,149,660 A | 11/2000 | Laufer |
| 6,163,948 A | 12/2000 | Esteves |
| 6,165,203 A | 12/2000 | Krebs |
| 6,168,633 B1 | 1/2001 | Shoher |
| 6,174,324 B1 | 1/2001 | Egan |
| 6,183,499 B1 | 2/2001 | Fischer |
| 6,187,095 B1 | 2/2001 | Labrecque |
| 6,203,565 B1 | 3/2001 | Bonutti et al. |
| 6,206,908 B1 | 3/2001 | Roby |
| 6,214,030 B1 | 4/2001 | Matsutani et al. |
| 6,231,911 B1 | 5/2001 | Steinback et al. |
| 6,235,869 B1 | 5/2001 | Roby |
| 6,241,747 B1 | 6/2001 | Ruff |
| 6,251,143 B1 | 6/2001 | Schwartz |
| 6,264,675 B1 | 7/2001 | Brotz |
| 6,267,772 B1 | 7/2001 | Mulhauser |
| 6,270,517 B1 | 8/2001 | Brotz |
| 6,315,788 B1 | 11/2001 | Roby |
| 6,319,231 B1 | 11/2001 | Andrulitis |
| 6,322,581 B1 | 11/2001 | Fukuda et al. |
| 6,334,865 B1 | 1/2002 | Redmond |
| 6,383,201 B1 | 5/2002 | Dong |
| 6,387,363 B1 | 5/2002 | Gruskin |
| 6,388,043 B1 | 5/2002 | Langer |
| 6,395,029 B1 | 5/2002 | Levy |
| D462,766 S | 9/2002 | Jacobs |
| 6,443,962 B1 | 9/2002 | Gaber |
| 6,463,719 B2 | 10/2002 | Dey |
| 6,471,715 B1 | 10/2002 | Weiss |
| 6,478,809 B1 | 11/2002 | Brotz |
| 6,485,503 B2 | 11/2002 | Jacobs |
| 6,491,701 B2 | 12/2002 | Tierney |
| 6,491,714 B1 | 12/2002 | Bennett |
| 6,494,898 B1 | 12/2002 | Roby |
| 6,495,127 B1 | 12/2002 | Wallace |
| RE37,963 E | 1/2003 | Thal |
| 6,506,190 B1 | 1/2003 | Walshe |
| 6,511,488 B1 | 1/2003 | Marshall |
| 6,514,265 B2 | 2/2003 | Ho |
| 6,527,795 B1 | 3/2003 | Lizardi |
| 6,548,002 B2 | 4/2003 | Gresser et al. |
| 6,548,569 B1 | 4/2003 | Williams et al. |
| 6,551,343 B1 | 4/2003 | Tormala |
| 6,554,802 B1 | 4/2003 | Pearson |
| 6,565,597 B1 | 5/2003 | Fearnot |
| 6,592,609 B1 | 7/2003 | Bonutti |
| 6,596,296 B1 | 7/2003 | Nelson |
| 6,599,310 B2 | 7/2003 | Leung |
| 6,607,541 B1 | 8/2003 | Gardiner |
| 6,610,078 B1 | 8/2003 | Bru-Magniez |
| 6,613,059 B2 | 9/2003 | Schaller |
| 6,613,254 B1 | 9/2003 | Shiffer |
| 6,616,982 B2 | 9/2003 | Merrill |
| 6,623,492 B1 | 9/2003 | Berube |
| 6,626,930 B1 | 9/2003 | Allen |
| 6,632,245 B2 | 10/2003 | Kim |
| 6,641,592 B1 | 11/2003 | Sauer |
| 6,641,593 B1 | 11/2003 | Schaller |
| 6,645,226 B1 | 11/2003 | Jacobs |
| 6,645,227 B2 | 11/2003 | Fallin |
| 6,645,228 B2 | 11/2003 | Renz |
| 6,648,921 B2 | 11/2003 | Anderson |
| 6,656,182 B1 | 12/2003 | Hayhurst |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,712,859 B2 | 3/2004 | Rousseau et al. |
| 6,716,234 B2 | 4/2004 | Grafton |
| 6,720,402 B2 | 4/2004 | Langer |
| 6,726,705 B2 | 4/2004 | Peterson |
| 6,746,443 B1 | 6/2004 | Morley |
| 6,746,458 B1 | 6/2004 | Cloud |
| 6,749,616 B1 | 6/2004 | Nath |
| 6,773,450 B2 | 8/2004 | Leung |
| 6,783,554 B2 | 8/2004 | Amara |
| 6,814,748 B1 | 11/2004 | Baker |
| 6,818,010 B2 | 11/2004 | Eichhorn |
| 6,838,493 B2 | 1/2005 | Williams |
| 6,848,152 B2 | 2/2005 | Genova |
| 6,852,825 B2 | 2/2005 | Lendlein |
| 6,858,222 B2 | 2/2005 | Nelson |
| 6,860,891 B2 | 3/2005 | Schulze |
| 6,860,901 B1 | 3/2005 | Baker |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman |
| 6,911,035 B1 | 6/2005 | Blomme |
| 6,911,037 B2 | 6/2005 | Gainor |
| 6,913,607 B2 | 7/2005 | Ainsworth |
| 6,921,811 B2 | 7/2005 | Zamora |
| 6,923,819 B2 | 8/2005 | Meade |
| 6,945,021 B2 | 9/2005 | Michel |
| 6,945,980 B2 | 9/2005 | Nguyen |
| 6,960,221 B2 | 11/2005 | Ho |
| 6,960,233 B1 | 11/2005 | Berg |
| 6,974,450 B2 | 12/2005 | Weber |
| 6,981,983 B1 | 1/2006 | Rosenblatt |
| 6,984,241 B2 | 1/2006 | Lubbers |
| 6,986,780 B2 | 1/2006 | Rudnick |
| 6,991,643 B2 | 1/2006 | Saadat |
| 6,996,880 B2 | 2/2006 | Kurtz, Jr. |
| 7,021,316 B2 | 4/2006 | Leiboff |
| 7,033,379 B2 | 4/2006 | Peterson |
| 7,033,603 B2 | 4/2006 | Nelson |
| 7,037,984 B2 | 5/2006 | Lendlein |
| 7,048,748 B1 | 5/2006 | Ustuner |
| 7,056,331 B2 | 6/2006 | Kaplan |
| 7,056,333 B2 | 6/2006 | Walshe |
| 7,057,135 B2 | 6/2006 | Li |
| 7,063,716 B2 | 6/2006 | Cunningham |

(56) References Cited

U.S. PATENT DOCUMENTS

| | | |
|---|---|---|
| 7,070,610 B2 | 7/2006 | Im |
| 7,081,135 B2 | 7/2006 | Smith |
| 7,083,637 B1 | 8/2006 | Tannhauser |
| 7,083,648 B2 | 8/2006 | Yu |
| 7,107,090 B2 | 9/2006 | Salisbury, Jr. |
| 7,112,214 B2 | 9/2006 | Peterson |
| 7,125,403 B2 | 10/2006 | Julian |
| 7,125,413 B2 | 10/2006 | Grigoryants |
| D532,107 S | 11/2006 | Peterson |
| 7,138,441 B1 | 11/2006 | Zhang |
| 7,141,302 B2 | 11/2006 | Mueller |
| 7,144,401 B2 | 12/2006 | Yamamoto |
| 7,144,412 B2 | 12/2006 | Wolf |
| 7,144,415 B2 | 12/2006 | Del Rio |
| 7,150,757 B2 | 12/2006 | Fallin |
| 7,156,858 B2 | 1/2007 | Schuldt-Hempe |
| 7,156,862 B2 | 1/2007 | Jacobs |
| 7,160,312 B2 | 1/2007 | Saadat |
| 7,166,570 B2 | 1/2007 | Hunter |
| 7,172,595 B1 | 2/2007 | Goble |
| 7,172,615 B2 | 2/2007 | Morriss |
| 7,186,262 B2 | 3/2007 | Saadat |
| 7,195,634 B2 | 3/2007 | Schmieding |
| 7,211,088 B2 | 5/2007 | Grafton |
| 7,214,230 B2 | 5/2007 | Brock |
| 7,217,744 B2 | 5/2007 | Lendlein |
| 7,225,512 B2 | 6/2007 | Genova |
| 7,226,468 B2 | 6/2007 | Ruff |
| 7,232,447 B2 | 6/2007 | Gellman |
| 7,244,270 B2 | 7/2007 | Lesh |
| 7,279,612 B1 | 10/2007 | Heaton |
| 7,297,142 B2 | 11/2007 | Brock |
| 7,322,105 B2 | 1/2008 | Lewis |
| 7,371,253 B2 | 5/2008 | Leung |
| 7,513,904 B2 | 4/2009 | Sulamanidze |
| 7,514,095 B2 | 4/2009 | Nelson |
| 7,582,105 B2 | 9/2009 | Kolster |
| 7,601,164 B2 | 10/2009 | Wu |
| 7,624,487 B2 | 12/2009 | Trull et al. |
| 7,806,908 B2 | 10/2010 | Ruff |
| 7,845,356 B2 | 12/2010 | Paraschac et al. |
| 7,857,829 B2 | 12/2010 | Kaplan et al. |
| 7,879,072 B2 | 2/2011 | Bonutti et al. |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |
| 2001/0039450 A1 | 11/2001 | Pavcnik et al. |
| 2001/0044637 A1 | 11/2001 | Jacobs et al. |
| 2001/0051807 A1 | 12/2001 | Grafton |
| 2001/0051815 A1 | 12/2001 | Esplin |
| 2002/0007218 A1 | 1/2002 | Cauthen |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0069617 A1 | 6/2002 | Dey et al. |
| 2002/0077448 A1 | 6/2002 | Antal et al. |
| 2002/0077631 A1 | 6/2002 | Lubbers et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0138009 A1 | 9/2002 | Brockway |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0173807 A1 | 11/2002 | Jacobs |
| 2002/0173822 A1 | 11/2002 | Justin |
| 2002/0179718 A1 | 12/2002 | Murokh |
| 2003/0014077 A1 | 1/2003 | Leung |
| 2003/0040795 A1 | 2/2003 | Elson |
| 2003/0041426 A1 | 3/2003 | Genova |
| 2003/0065360 A1 | 4/2003 | Jacobs |
| 2003/0065402 A1 | 4/2003 | Anderson |
| 2003/0069602 A1 | 4/2003 | Jacobs |
| 2003/0074021 A1 | 4/2003 | Morriss |
| 2003/0074023 A1 | 4/2003 | Kaplan |
| 2003/0078604 A1 | 4/2003 | Walshe |
| 2003/0088270 A1 | 5/2003 | Lubbers |
| 2003/0097150 A1 | 5/2003 | Fallin |
| 2003/0105489 A1 | 6/2003 | Eichhorn |
| 2003/0149447 A1 | 8/2003 | Morency |
| 2003/0158604 A1 | 8/2003 | Cauthen, III |
| 2003/0167072 A1 | 9/2003 | Oberlander |
| 2003/0199923 A1 | 10/2003 | Khairkhahan et al. |
| 2003/0203003 A1 | 10/2003 | Nelson |
| 2003/0204193 A1 | 10/2003 | Gabriel et al. |
| 2003/0204195 A1 | 10/2003 | Keane |
| 2003/0225424 A1 | 12/2003 | Benderev |
| 2003/0229361 A1 | 12/2003 | Jackson |
| 2003/0236550 A1 | 12/2003 | Peterson |
| 2003/0236551 A1 | 12/2003 | Peterson |
| 2004/0006353 A1 | 1/2004 | Bosley, Jr. et al. |
| 2004/0010275 A1 | 1/2004 | Jacobs |
| 2004/0010276 A1 | 1/2004 | Jacobs |
| 2004/0015187 A1 | 1/2004 | Lendlein |
| 2004/0024169 A1 | 2/2004 | Shalaby et al. |
| 2004/0024420 A1 | 2/2004 | Lubbers |
| 2004/0028655 A1 | 2/2004 | Nelson |
| 2004/0030354 A1 | 2/2004 | Leung |
| 2004/0039415 A1 | 2/2004 | Zamierowski |
| 2004/0049224 A1 | 3/2004 | Buehlmann et al. |
| 2004/0059370 A1 | 3/2004 | Greene, Jr. et al. |
| 2004/0059377 A1 | 3/2004 | Peterson |
| 2004/0059378 A1 | 3/2004 | Peterson |
| 2004/0060409 A1 | 4/2004 | Leung |
| 2004/0060410 A1 | 4/2004 | Leung |
| 2004/0068293 A1 | 4/2004 | Scalzo |
| 2004/0068294 A1 | 4/2004 | Scalzo |
| 2004/0088003 A1 | 5/2004 | Leung |
| 2004/0093023 A1 | 5/2004 | Allen |
| 2004/0093028 A1 | 5/2004 | Ruff |
| 2004/0098051 A1 | 5/2004 | Fallin |
| 2004/0106949 A1 | 6/2004 | Cohn |
| 2004/0116620 A1 | 6/2004 | Shalaby et al. |
| 2004/0138683 A1 | 7/2004 | Shelton |
| 2004/0153153 A1 | 8/2004 | Elson |
| 2004/0167572 A1 | 8/2004 | Roth |
| 2004/0167575 A1 | 8/2004 | Roby |
| 2004/0186487 A1 | 9/2004 | Klein et al. |
| 2004/0193191 A1 | 9/2004 | Starksen |
| 2004/0193217 A1 | 9/2004 | Lubbers |
| 2004/0193257 A1 | 9/2004 | Wu |
| 2004/0226427 A1 | 11/2004 | Trull |
| 2004/0230223 A1 | 11/2004 | Bonutti et al. |
| 2004/0237736 A1 | 12/2004 | Genova |
| 2004/0254609 A1 | 12/2004 | Esplin |
| 2004/0260340 A1 | 12/2004 | Jacobs |
| 2004/0265282 A1 | 12/2004 | Wright |
| 2004/0267309 A1 | 12/2004 | Garvin |
| 2005/0004601 A1 | 1/2005 | Kong |
| 2005/0004602 A1 | 1/2005 | Hart |
| 2005/0033324 A1 | 2/2005 | Phan |
| 2005/0033367 A1 | 2/2005 | Leung |
| 2005/0034431 A1 | 2/2005 | Dey |
| 2005/0038472 A1 | 2/2005 | Furst |
| 2005/0049636 A1 | 3/2005 | Leiboff |
| 2005/0055051 A1 | 3/2005 | Grafton |
| 2005/0059984 A1 | 3/2005 | Chanduszko |
| 2005/0065533 A1 | 3/2005 | Magen |
| 2005/0070959 A1 | 3/2005 | Cichocki, Jr. |
| 2005/0080455 A1 | 4/2005 | Schmieding |
| 2005/0085857 A1 | 4/2005 | Peterson et al. |
| 2005/0096698 A1 | 5/2005 | Lederman |
| 2005/0106211 A1 | 5/2005 | Nelson |
| 2005/0113936 A1 | 5/2005 | Brustad |
| 2005/0119694 A1 | 6/2005 | Jacobs |
| 2005/0125020 A1 | 6/2005 | Meade |
| 2005/0125034 A1 | 6/2005 | Cichocki, Jr. |
| 2005/0125035 A1 | 6/2005 | Cichocki, Jr. |
| 2005/0149064 A1 | 7/2005 | Peterson |
| 2005/0149118 A1 | 7/2005 | Koyfman |
| 2005/0154255 A1 | 7/2005 | Jacobs |
| 2005/0171561 A1 | 8/2005 | Songer |
| 2005/0177190 A1 | 8/2005 | Zamierowski |

(56) References Cited

U.S. PATENT DOCUMENTS

| | | |
|---|---|---|
| 2005/0182444 A1 | 8/2005 | Peterson |
| 2005/0182445 A1 | 8/2005 | Zamierowski |
| 2005/0186247 A1 | 8/2005 | Hunter et al. |
| 2005/0197699 A1 | 9/2005 | Jacobs |
| 2005/0199249 A1 | 9/2005 | Karram |
| 2005/0203576 A1 | 9/2005 | Sulamanidze |
| 2005/0209542 A1 | 9/2005 | Jacobs |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0240224 A1 | 10/2005 | Wu |
| 2005/0267531 A1 | 12/2005 | Ruff |
| 2005/0267532 A1 | 12/2005 | Wu |
| 2005/0277984 A1 | 12/2005 | Long |
| 2005/0283246 A1 | 12/2005 | Cauthen |
| 2006/0020272 A1 | 1/2006 | Gildenberg |
| 2006/0030884 A1 | 2/2006 | Yeung |
| 2006/0036266 A1 | 2/2006 | Sulamanidze |
| 2006/0058574 A1 | 3/2006 | Priewe |
| 2006/0058799 A1 | 3/2006 | Elson |
| 2006/0058844 A1 | 3/2006 | White |
| 2006/0063476 A1 | 3/2006 | Dore |
| 2006/0064115 A1 | 3/2006 | Allen |
| 2006/0064116 A1 | 3/2006 | Allen |
| 2006/0064127 A1 | 3/2006 | Fallin |
| 2006/0079935 A1 | 4/2006 | Kolster |
| 2006/0085016 A1 | 4/2006 | Eremia |
| 2006/0089525 A1 | 4/2006 | Mamo |
| 2006/0089672 A1 | 4/2006 | Martinek |
| 2006/0111734 A1 | 5/2006 | Kaplan |
| 2006/0111742 A1 | 5/2006 | Kaplan |
| 2006/0122608 A1 | 6/2006 | Fallin |
| 2006/0135994 A1 | 6/2006 | Ruff |
| 2006/0135995 A1 | 6/2006 | Ruff |
| 2006/0142784 A1 | 6/2006 | Kontos |
| 2006/0193769 A1 | 8/2006 | Nelson |
| 2006/0194721 A1 | 8/2006 | Allen |
| 2006/0200062 A1 | 9/2006 | Saadat |
| 2006/0207612 A1 | 9/2006 | Jackson |
| 2006/0229671 A1 | 10/2006 | Steiner |
| 2006/0235445 A1 | 10/2006 | Birk |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin |
| 2006/0253126 A1 | 11/2006 | Bjerken |
| 2006/0257629 A1 | 11/2006 | Lendlein |
| 2006/0258938 A1 | 11/2006 | Hoffman |
| 2006/0272979 A1 | 12/2006 | Lubbers |
| 2006/0276808 A1 | 12/2006 | Arnal |
| 2006/0282099 A1 | 12/2006 | Stokes |
| 2006/0286289 A1 | 12/2006 | Prajapati |
| 2006/0287675 A1 | 12/2006 | Prajapati |
| 2006/0287676 A1 | 12/2006 | Prajapati |
| 2006/0293710 A1 | 12/2006 | Foerster |
| 2007/0005109 A1 | 1/2007 | Popadiuk |
| 2007/0005110 A1 | 1/2007 | Collier |
| 2007/0021779 A1 | 1/2007 | Garvin |
| 2007/0027475 A1 | 2/2007 | Pagedas |
| 2007/0038249 A1 | 2/2007 | Kolster |
| 2007/0065663 A1 | 3/2007 | Trull |
| 2007/0088391 A1 | 4/2007 | McAlexander |
| 2007/0135840 A1 | 6/2007 | Schmieding |
| 2007/0135843 A1 | 6/2007 | Burkhart |
| 2007/0151961 A1 | 7/2007 | Kleine et al. |
| 2007/0156175 A1 | 7/2007 | Weadock et al. |
| 2007/0167958 A1 | 7/2007 | Sulamanidze et al. |
| 2007/0187861 A1 | 8/2007 | Geneva et al. |
| 2007/0208355 A1 | 9/2007 | Ruff |
| 2007/0208377 A1 | 9/2007 | Kaplan |
| 2007/0219587 A1 | 9/2007 | Accardo |
| 2007/0224237 A1 | 9/2007 | Hwang |
| 2007/0225642 A1 | 9/2007 | Houser |
| 2007/0225761 A1 | 9/2007 | Shetty |
| 2007/0227914 A1 | 10/2007 | Cerwin |
| 2007/0233188 A1 | 10/2007 | Hunt |
| 2007/0239206 A1 | 10/2007 | Shelton, IV |
| 2007/0239207 A1 | 10/2007 | Beramendi |
| 2007/0257395 A1 | 11/2007 | Lindh |
| 2007/0282247 A1 | 12/2007 | Desai |
| 2008/0004490 A1 | 1/2008 | Bosley et al. |
| 2008/0004603 A1 | 1/2008 | Larkin |
| 2008/0009838 A1 | 1/2008 | Schena |
| 2008/0009888 A1 | 1/2008 | Ewers |
| 2008/0009902 A1 | 1/2008 | Hunter |
| 2008/0027273 A1 | 1/2008 | Gutterman |
| 2008/0027486 A1 | 1/2008 | Jones |
| 2008/0046094 A1 | 2/2008 | Han |
| 2008/0058869 A1 | 3/2008 | Stopek |
| 2008/0066764 A1 | 3/2008 | Paraschac |
| 2008/0066765 A1 | 3/2008 | Paraschac |
| 2008/0066766 A1 | 3/2008 | Paraschac |
| 2008/0066767 A1 | 3/2008 | Paraschac |
| 2008/0077181 A1 | 3/2008 | Jones |
| 2008/0082113 A1 | 4/2008 | Bishop |
| 2008/0082129 A1 | 4/2008 | Jones |
| 2008/0086169 A1 | 4/2008 | Jones |
| 2008/0086170 A1 | 4/2008 | Jones |
| 2008/0109036 A1 | 5/2008 | Stopek |
| 2008/0132943 A1 | 6/2008 | Maiorino |
| 2008/0195147 A1 | 8/2008 | Stopek |
| 2008/0208358 A1 | 8/2008 | Bellamkonda |
| 2008/0215072 A1 | 9/2008 | Kelly |
| 2008/0221618 A1 | 9/2008 | Chen |
| 2008/0234731 A1 | 9/2008 | Leung |
| 2008/0248216 A1 | 10/2008 | Yeung |
| 2008/0255611 A1 | 10/2008 | Hunter |
| 2008/0262542 A1 | 10/2008 | Sulamanidze |
| 2008/0281338 A1 | 11/2008 | Wohlert |
| 2008/0312688 A1 | 12/2008 | Nawrocki |
| 2009/0012560 A1 | 1/2009 | Hunter |
| 2009/0018577 A1 | 1/2009 | Leung |
| 2009/0043336 A1 | 2/2009 | Yuan |
| 2009/0076543 A1 | 3/2009 | Maiorino |
| 2009/0099597 A1 | 4/2009 | Isse |
| 2009/0107965 A1 | 4/2009 | D'Agostino |
| 2009/0112236 A1 | 4/2009 | Stopek |
| 2009/0112259 A1 | 4/2009 | D'Agostino |
| 2009/0200487 A1 | 8/2009 | Maiorino |
| 2009/0210006 A1 | 8/2009 | Cohen |
| 2009/0216253 A1 | 8/2009 | Bell et al. |
| 2009/0226500 A1 | 9/2009 | Avelar |
| 2009/0248066 A1 | 10/2009 | Wilkie |
| 2009/0248067 A1 | 10/2009 | Maiorino |
| 2009/0248070 A1 | 10/2009 | Kosa |
| 2009/0250356 A1 | 10/2009 | Kirsch |
| 2009/0259233 A1 | 10/2009 | Bogart |
| 2009/0259251 A1 | 10/2009 | Cohen |
| 2009/0287245 A1 | 11/2009 | Ostrovsky |
| 2009/0299407 A1 | 12/2009 | Yuan |
| 2009/0299408 A1 | 12/2009 | Schuldt-Hempe |
| 2009/0306710 A1 | 12/2009 | Lindh |
| 2010/0023055 A1 | 1/2010 | Rousseau |
| 2010/0057123 A1 | 3/2010 | D'Agostino |
| 2010/0063540 A1 | 3/2010 | Maiorino |
| 2010/0071833 A1 | 3/2010 | Maiorino |
| 2010/0087855 A1 | 4/2010 | Leung |
| 2010/0101707 A1 | 4/2010 | Maiorino |
| 2010/0140115 A1 | 6/2010 | Kirsch |
| 2010/0292718 A1 | 11/2010 | Sholev et al. |
| 2010/0294103 A1 | 11/2010 | Genova |
| 2010/0294104 A1 | 11/2010 | Genova |
| 2010/0294105 A1 | 11/2010 | Genova |
| 2010/0294106 A1 | 11/2010 | Genova |
| 2010/0294107 A1 | 11/2010 | Genova |
| 2010/0298637 A1 | 11/2010 | Ruff |
| 2010/0298867 A1 | 11/2010 | Ruff |
| 2010/0298868 A1 | 11/2010 | Ruff |
| 2010/0298871 A1 | 11/2010 | Ruff et al. |
| 2010/0298878 A1 | 11/2010 | Leung et al. |
| 2010/0298879 A1 | 11/2010 | Leung et al. |
| 2010/0298880 A1 | 11/2010 | Leung et al. |
| 2010/0313723 A1 | 12/2010 | Genova |
| 2010/0313729 A1 | 12/2010 | Genova |

(56) References Cited

U.S. PATENT DOCUMENTS

| | | | |
|---|---|---|---|
| 2010/0313730 A1 | 12/2010 | Genova | |
| 2010/0318122 A1 | 12/2010 | Leung et al. | |
| 2010/0318123 A1 | 12/2010 | Leung et al. | |
| 2011/0009902 A1 | 1/2011 | Leung et al. | |
| 2011/0046669 A1 | 2/2011 | Goraltchouk et al. | |
| 2011/0130774 A1 | 6/2011 | Criscuolo et al. | |
| 2013/0165971 A1* | 6/2013 | Leung et al. | 606/228 |

FOREIGN PATENT DOCUMENTS

| | | |
|---|---|---|
| CN | 2640420 | 9/2004 |
| DE | 1810800 | 6/1970 |
| DE | 3227984 | 7/1982 |
| DE | 4302895 | 8/1994 |
| DE | 19618891 | 4/1997 |
| DE | 19833703 | 2/2000 |
| DE | 102005004317 | 6/2006 |
| EP | 0121362 | 9/1987 |
| EP | 0329787 | 8/1989 |
| EP | 0428253 | 5/1991 |
| EP | 0576337 | 12/1993 |
| EP | 0632999 | 1/1995 |
| EP | 0513736 | 2/1995 |
| EP | 0464479 | 3/1995 |
| EP | 0464480 | 3/1995 |
| EP | 0574707 | 8/1997 |
| EP | 0612504 | 11/1997 |
| EP | 0826337 | 3/1998 |
| EP | 0558993 | 4/1998 |
| EP | 0839499 | 5/1998 |
| EP | 0913123 | 5/1999 |
| EP | 0916310 | 5/1999 |
| EP | 0664198 | 6/1999 |
| EP | 0960600 | 12/1999 |
| EP | 1075843 | 2/2001 |
| EP | 0705567 | 3/2002 |
| EP | 0673624 | 8/2002 |
| EP | 0755656 | 12/2003 |
| EP | 1525851 | 4/2005 |
| EP | 1532942 | 5/2005 |
| EP | 0991359 | 11/2007 |
| EP | 1948261 | 11/2010 |
| EP | 1726317 | 7/2012 |
| EP | 2338421 | 11/2012 |
| FR | 2619129 | 2/1989 |
| FR | 2693108 | 1/1994 |
| FR | 9208059 | 3/1997 |
| GB | 267007 | 3/1927 |
| GB | 1091282 | 11/1967 |
| GB | 1428560 | 3/1976 |
| GB | 1506362 | 4/1978 |
| GB | 1508627 | 4/1978 |
| JP | 51-130091 | 11/1976 |
| JP | 1506362 | 4/1978 |
| JP | 354116419 | 9/1979 |
| JP | 63-500702 | 3/1988 |
| JP | 63288146 | 11/1988 |
| JP | 01113091 | 5/1989 |
| JP | 003-165751 | 7/1991 |
| JP | 4-096758 | 3/1992 |
| JP | 4-226642 | 8/1992 |
| JP | 2004-266749 | 9/1992 |
| JP | 9-103477 | 4/1997 |
| JP | 10-511009 | 10/1997 |
| JP | 10-503389 | 3/1998 |
| JP | 410085225 | 4/1998 |
| JP | 11-313826 | 11/1999 |
| JP | 11332828 | 12/1999 |
| JP | 2002-59235 | 2/2002 |
| JP | 2003-275217 | 9/2003 |
| JP | 2004-530524 | 10/2004 |
| JP | 2005-500119 | 1/2005 |
| JP | 1988/009157 | 7/2006 |
| JP | 2006-517112 | 7/2006 |
| KR | 10-2005-0072908 A | 7/2005 |
| KR | 2006-59142 | 6/2006 |
| NZ | 501224 | 3/2002 |
| NZ | 531262 | 6/2002 |
| RU | 1745214 | 7/1992 |
| RU | 1752358 | 8/1992 |
| RU | 1823791 | 6/1993 |
| RU | 2139690 | 10/1999 |
| RU | 2175855 | 11/2001 |
| RU | 2241389 | 12/2004 |
| RU | 2268752 | 1/2006 |
| SU | 1745214 | 7/1992 |
| SU | 1752358 | 8/1992 |
| WO | 86/00020 | 1/1986 |
| WO | 87/01270 | 3/1987 |
| WO | 89/05618 | 12/1988 |
| WO | 90/09149 | 6/1989 |
| WO | 92/22336 | 8/1990 |
| WO | 90/14795 | 12/1990 |
| WO | 98/55031 | 12/1992 |
| WO | 95/16399 | 6/1995 |
| WO | WO9606565 | 3/1996 |
| WO | WO 9852473 | 11/1998 |
| WO | 99/33401 | 12/1998 |
| WO | WO 9921488 | 5/1999 |
| WO | 99/62431 | 7/1999 |
| WO | WO9995477 | 11/1999 |
| WO | WO 00/51685 | 9/2000 |
| WO | WO0051658 | 9/2000 |
| WO | 01/06952 | 2/2001 |
| WO | 01/56626 | 8/2001 |
| WO | WO03001979 | 1/2003 |
| WO | WO03017850 | 3/2003 |
| WO | WO03045255 | 6/2003 |
| WO | 03/077772 | 9/2003 |
| WO | 03/092758 | 11/2003 |
| WO | 03/105703 | 12/2003 |
| WO | WO03103733 | 12/2003 |
| WO | WO03103972 | 12/2003 |
| WO | WO2004014236 | 2/2004 |
| WO | 2004/030517 | 4/2004 |
| WO | WO2004030520 | 4/2004 |
| WO | WO2004030704 | 4/2004 |
| WO | WO2004030705 | 4/2004 |
| WO | 2004/062459 | 7/2004 |
| WO | 2004/100801 | 11/2004 |
| WO | WO2004112853 | 12/2004 |
| WO | 2005/074913 | 8/2005 |
| WO | 2005/096955 | 10/2005 |
| WO | 2005/096956 | 10/2005 |
| WO | 2005/112787 | 12/2005 |
| WO | WO2006005144 | 1/2006 |
| WO | 2006/012128 | 2/2006 |
| WO | 6013299 A | 2/2006 |
| WO | WO2006061868 | 6/2006 |
| WO | 2006/079469 | 8/2006 |
| WO | WO2006082060 | 8/2006 |
| WO | WO2006099703 | 9/2006 |
| WO | 2007/005291 | 1/2007 |
| WO | 2007/005296 | 1/2007 |
| WO | WO2007053812 | 5/2007 |
| WO | 2007/112024 | 10/2007 |
| WO | WO2007133103 | 11/2007 |
| WO | WO2007145614 | 12/2007 |
| WO | 2008/128113 | 10/2008 |
| WO | 2008/150773 | 12/2008 |
| WO | 2009/042841 | 4/2009 |
| WO | WO2009068252 | 6/2009 |
| WO | WO2009087105 | 7/2009 |
| WO | 2009/097556 | 8/2009 |
| WO | 2009/151876 | 12/2009 |
| WO | WO2010052007 | 5/2010 |

OTHER PUBLICATIONS

International Search Report for PCT/US2008/060127 dated Sep. 23, 2008, 5 pages.

International Search Report for PCT/US2008/064921 dated Nov. 19, 2008, 3 pages.

(56) References Cited

OTHER PUBLICATIONS

International Search Report for PCT/US2008/075849 dated Mar. 18, 2009, 4 pages.
Singapore Search Report for Singapore Patent Application No. 200702625-5 dated Nov. 26, 2008, 7 pages.
Singapore Search Report for Singapore Patent Application No. 200702350-0 dated Nov. 26, 2008, 6 pages.
Singapore Search Report for Singapore Patent Application No. 200703688-2 dated Nov. 26, 2008, 7 pages.
European Search Report for EP07015905.8 dated Oct. 23, 2007, 2 pages.
European Search Report for EP10000629.5. dated Mar. 10, 2010, 4 pages.
European Search Report for EP10011871.0 dated Dec. 3, 2010, 2 pages.
European Search Report for EP10011868.6 dated Dec. 6, 2010, 2 pages.
European Search Report for EP10186592.1 dated Jan. 19, 2011, 2 pages.
Mason, M.L., "Primary and secondary tendon suture. A discussion of the significance of technique in tendon surgery", Surg Gynecol Obstet 70 (1940).
McKee, G.K., "Metal anastomosis tubes in tendon suture", The Lancet, May 26, 1945, 659-660.
Mansberger, et al., "A New Type Pull-Out Wire for Tendon Surgery: A Preliminary Report", Department of Surgery, University Hospital and University of Maryland School of Medicine, Baltimore, Maryland, pp. 119-121.
Jennings et al., "A new technique in primary tendon repair", Surg Gynecol Obstet Nov. 1952;95(5):597-600.
Bunnell, S., "Gig pull-out suture for tendons", J Bone Joint Surg Am. Jul. 1954;36-A(4):850-1.
Verdan, Claude, "Primary Repair of Flexor Tendons", Journal of Bone and Joint Surgery Jun. 1960; 42(4):647-657.
Potenza, Austin, "Tendon Healing Within the Flexor Digital Sheath in the Dog: An Experimental Study", Journal of Bone & Joint Surgery Jan. 1962; 44A(1):49-64.
Pulvertaft, "Suture Materials and Tendon Junctures", American Journal of Surgery Mar. 1965; 109:346-352.
Buncke, Jr., H.J. et al., "The suture repair of one-millimeter vessels, micro-vascular surgery", Report of First Conference; Oct. 6-7, 1966; pp. 24-35 (esp. p. 34), USA.
McKenzie, A.R., "An Experimental Multiple Barbed Suture for the Long Flexor Tendons of the Palm and Fingers", Journal of Bone and Joint Surgery 1967; 49B(3): 440-447.
Zoltan, Janos, "Cicatrix Optimia: Techniques for Ideal Wound Healing", English language edition University Park Press, Baltimore, 1977:Chapter 3; pp. 54-55.
Han, Hongtao et al., "Mating and Piercing Micromechanical Structures for Surface Bonding Applications", Proceedings of the 1991 Micro Electro Mechanical Systems (MEMS >91), An Investigation of Micro Structures, Sensors, Actuators, Machines and Robots, Feb. 1991, pp. 253-258.
Malina, Martin et al., "Endovascular AAA Exclusion: Will Stents With Hooks and Barbs Prevent Stent-Graft Migration", Journal Endovascular Surgery 1998(5): 310-317.
Boenisch, U.W. et al., "Pull-our strength and stiffness of meniscal repair using absorbable arrows or Ti-Cron vertical and horizontal loop sutures", American Journal of Sports Medicine, Sep.-Oct. 1999, pp. 626-631, vol. 27, Issue 5.
Sulamanidze, MD, M.A., et al., "Management of Facial Rhytids by Subcutaneous Soft Tissue Dissection", International Journal of Cosmetic Surgery and Aesthetic Dermatology, vol. 2(4), 2000, pp. 255-259.
Rofin-Baasel, "Laser Marking on Plastic Materials", 2001.RB50.0, Rofin-Baasel Inc. 2001, 2 pages.
Semenov, G. M. et al., "Surgical Suture", 2001, pp. 12-13 and 92-98, Piter, Saint Petersburg.
Sulamanidze, M.A. et al., "Facial lifting with Aptos threads", International Journal of Cosmetic Surgery and Aesthetic Dermatology, 2001, pp. 1-8, No. 4.
Dattillo, Jr., Philip Paul, "Medical Textile: Application of an Absorbable Barbed Bi-Directional Surgical Suture", Journal of Textile and Apparel, Technology and Management, vol. 2(2), Spring 2002, pp. 1-5.
Lendlein, Andreas et al., "Biodegradable, Elastic Shape-Memory Polymers for Potential Biomedical Applications", Science vol. 296; May 31, 2002, pp. 1673-1676.
Leung, J. et al., "Barbed, Bi-directional Medical Sutures: Biomechanical Properties and Wound Closure Efficacy Study", 2002 Society for Biomaterials $28^{th}$ Annual Meeting Transactions, 1 page.
Sulamanidze, MD, M.A., et al., "Removal of Facial Soft Tissue Ptosis with Special Threads", Dermatol Surg 2002; 28; pp. 367-371.
Lendlein, Andreas et al., "Shape-Memory Polymers", Angew, Chem. Int. Ed. 2002, 41, 2034-2057.
Sulamanidze, MD, M.A., et al., "Clinical aspects of bloodless facelift using APTOS filaments", A.V. Vishnevsky Institute of Surgery, Bol=shaya Serpukhovskaya ul., 27, 113811 Moscow, Russia, (2002):24-34.
Sulamanidze, MD, M.A., et al., "Morphological foundations of facelift using APTOS filaments", Bolshaya Serpukhovskaya ul., 27, 113811 Moscow, Russia, (2002): 19-26.
Dattillo, Jr., Philip Paul, et al., "Tissue Holding Performance of Knotless Absorbable Sutures", 2003 Society for Biomaterials $29^{th}$ Annual Meeting Transactions, p. 101.
Ingle, Nilesh P et al., "Mechanical Performance and Finite Element Analysis of Bi-directional Barbed Sutures", Master of Science in Textile Technology & Management at North Carolina State University Aug. 2003, 126 pages.
Kuniholm, Jonathan Fairbank, et al., "Automated Knot Tying for Fixation in Minimally Invasive, Robot Assisted Cardiac Surgery", Master of Science in Mechanical & Aerospace Engineering at North Carolina State University May 2003, 71 pages.
Leung, J. et al., "Barbed Bi-directional Surgical Sutures: In Vivo Strength and Histopathology Evaluations", 2003 Society for Biomaterials $29^{th}$ Annual Meeting Transactions, p. 100.
Li, Yang Yang, et al., "Polymer Replicas of Photonic Porous Silicon for Sensing and Drug Delivery Applications", Science vol. 299; Mar. 28, 2003, pp. 2045-2047.
Leung, Jeffrey C. et al., "Barbed, Bi-Directional Surgical Sutures", International Conference & Exhibition on Healthcare & Medical Textiles, Jul. 8-9, 2003; 1-8.
Szarmach, Robin et al., "An Expanded Surgical Suture and Needle Evauulation and Selection Program by a Healthcare Resource Management Group Purchasing Organization", Journal of Long-Term Effects of Medical Implants 2003; 13(3); 155-170.
Ingle, Nilesh P et al., "Barbed Suture Anchoring Strength: Applicability to Dissimilar Polymeric Materials", College of Textiles, North Carolina State University, $7^{th}$ World Biomaterials Congress 2004, 1 page.
Leung, J. et al., "Performance Enhancement of a Knotless Suture via Barb Geometry Modifications", $7^{th}$ World Biomaterials Congress 2004, 1 page.
Wu, Woffles, "Barbed Sutures in Facial Rejuvenation", Aesthetic Surgery Journal 2004(24): 582-587.
Quill Medical, Inc., "Quill Medical's Novel-Self-Anchoring Surgical Suture Approved for Sale in Europe", Press Release; Research Triangle Park, N.C., May 10, 2004, 1 page.
Buckley, Patrick R., "Actuation of Shape Memory Polymer using Magnetic Fields for Applications in Medical Devices", Master of Science in Mechanical Engineering at the Massachusetts Institute of Technology Jun. 2003, 144 pgs.
Quill Medical, Inc., "Barbed sutures, wrinkle filters give patients more innovative, non-surgical options", Press Release of Program presented at American Society of Plastic Surgeons annual scientific meeting; Philadelphia, Oct. 9, 2004, 3 pages.
Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.

(56) References Cited

OTHER PUBLICATIONS

Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.
Surgical Specialties Corporation, "Wound Closure Catalog"; Summer 2005, 5 pages.
Rodeheaver, G.T. et al., "Barbed Sutures for Wound Closure: In Vivo Wound Security, Tissue Compatibility and Cosmesis Measurements", Society for Biomaterials 30th Annual Meeting Transactions, 2005, 2 pages.
Belkas, J. S. et al., "Peripheral nerve regeneration through a synthetic hydrogel nerve tube", Restorative Neurology and Neuroscience 23 (2005) 19-29.
Ingle, Nilesh P et al., "Testing the Tissue-holding Capacity of Barbed Sutures", College of Textiles, North Carolina State University, Fiber Science, The Next Generation Oct. 17-19, 2005, New Jersey Institute of Technology, Newark, NJ, 4 pages.
Liu, Changdeng et at, "Shape Memory Polymer with Improved Shape Recovery", Mater. Res. Soc. Symp. Proc. vol. 855E, 2005 Materials Research Society, pp. W4.7.1-W4.7.6.
De Persia, Raúl et al., "Mechanics of Biomaterials: Sutures After the Surgery", Applications of Engineering Mechanics in Medicine, GED-University of Puerto Rico, Mayaguez May 2005, p. F1-F27.
Scherman, Peter et al., "Sutures as longitudinal guides for the repair of nerve defects-Influence of suture numbers and reconstruction of nerve bifurcations", Restorative Neurology and Neuroscience 23 (2005) 79-85.
Sulamanidze, MD, M.A., et al., "Soft tissue lifting in the mid-face: old philosophy, new approach-internal stitching technique (APTOS Needle)", Plastic and Aesthetic Surgery Clinic Total SHARM, Moscow, Russia, (2005):15-29.
Bacci, Pier Antonio, "Chirurgia Estetica Mini Invasiva Con Fili Di Sostegno", Collana di Arti, Pensiero e Scienza; Minelli Editore— 2006; 54 pgs.
Bellin, I. et al., "Polymeric triple-shape materials", Proceedings of the National Academy of Sciences of the United States of America Nov. 28, 2006; 2103(48):18043-18047.
Delorenzi, C.L., "Barbed Sutures: Rationale and Technique", Aesthetic Surg J. Mar. 26, 2006(2): 223-229.
Gross, Alex, "Physician perspective on thread lifts", Dermatology Times Feb. 27, 2006(2): 2 pages.
Khademhosseini, Ali et al., "Nanobiotechnology Drug Delivery and Tissue Engineering", Chemical Engineering Progress 102:38-42 (2006).
Murtha et al., "Evaluation of a Novel Technique for Wound Closure Using a Barbed Suture", Journal American Society of Plastic Surgeons 2006; 117(6); 1769-1780.
Ruff, Gregory, "Technique and Uses for Absorbable Barbed Sutures", Aesthetic Surgery Journal Sep./Oct. 2006; 26:620-628.
Behl, Marc et al., "Shape-Memory Polymers", Materials Today Apr. 2007; 10(4); 20-28.
Kaminer, M. et al., "ContourLift™: A New Method of Minimally Invasive Facial Rejuvenation", Cosmetic Dermatology Jan. 2007; 20(1): 29-35.
Kelch et al., "Shape-memory Polymer Networks from Olio[(0-hydroxycaproate)-co-glycolate]dimethacrylates and Butyl Acrylate with Adjustable Hydrolytic Degradation Rate", Biomacromolecules 2007;8(3):1018-1027.
Maitland et al., "Prototype laser-activated shape memory polymer foam device for embolic treatment of aneurysms", Journal of Biomedical Optics May/Jun. 2007;12(3): pp. 030504-1 to 030504-3.
Moran et al., "Bidirectional-Barbed Sutured Knotless Running Anastomosis v Classic van Velthovan in a Model System", Journal of Endourology Oct. 2007; 21(10); 1175-1177.
Mullner, "Metal Foam Has a Good Memory", Dec. 18, 2007 Original story at <http://www.physorg.com/news117214996.html>.
Paul, Malcolm D. and Rui Avelar, "Quill™ SRS Techniques & Procedures a Novel Approach to Soft Tissue Approximation", Canada, Angiotech Pharmaceuticals, Inc., First Edition [8]2007: 20 pages.
Paul, Malcolm D. and Rui Avelar, "Quill™ SRS Techniques & Procedures a Novel Approach to Soft Tissue Approximation", Canada, Angiotech Pharmaceuticals, Inc., Second Edition [8]2008: 20 pages.
Paul, Malcolm D. and Rui Avelar, "Quill™ SRS Techniques & Procedures a Novel Approach to Soft Tissue Approximation", Canada, Angiotech Pharmaceuticals, Inc., Third Edition 2009, [8] 2007-2009: 27 pages.
Paul, Malcolm D. and Rui Avelar, "Quill™ SRS Techniques & Procedures a Novel Approach to Soft Tissue Approximation", Canada, Angiotech Pharmaceuticals, Inc., Fourth Edition 2010, [8] 2007-2010: 27 pages.
Dahlin, Lars, "Techniques of Peripheral Nerve Repair", Scandinavian Journal of Surgery 97: 310-316, 2008.
Madduri, Srinivas, et al., "Neurotrophic factors release from nerve conduits for peripheral axonal regeneration", European Cells and Materials vol. 16; Suppl. 1 (2008), p. 14.
Nie, Zhihong and Kumacheva, Eugenia, "Patterning surfaces with functional polymers", Nature Materials vol. 7(2008): 277-290.
Paul, Malcolm D., "Using Barbed Sutures in Open/Subperiosteal Midface Lifting", Aesthetic Surgery Journal 2006(26): 725-732.
Richert, Ludovic, et al., "Surface Nanopatterning to Control Cell Growth", Advanced Materials 2008(15): 1-5.
Tan Ee Lim et al., "A wireless, passive strain sensor based on the harmonic response of magnetically soft materials", Smart Materials and Structures 17 (2008): pp. 1-6.
Villa, Mark T. et al., "Barbed Sutures: A Review of Literature", Plastic and Reconstructive Surgery; Mar. 2008; vol. 121, No. 3; pp. 102e-108e.
Demyttenaere, Sebastian V. et al., "Barbed Suture for Gastrointestinal Closure: A Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Paul, Malcolm D., "Bidirectional Barbed Sutures for Wound Closure: Evoluation and Applications", Journal of the American College of Certified Wound Specialists (2009) 1, 51-57.
Sulamanidze, Marlen et al., "APTOS Suture Lifting Methods: 10 Years of Experience", Clin Plastic Surg 36 (2009); pp. 281-306.
Ingle, N.P. et al., "Optimizing the tissue anchoring performance of barbed sutures in skin and tendon tissues", Journal of Biomechanics 43 (2010); pp. 302-309.
International Search Report for PCT/US2002/027525 dated Dec. 9, 2002, 3 pages.
European Search Report for EP107006258.3 dated May 4, 2007, 4 pages.
European Search Report for EP07015906 dated Oct. 2, 2007.
International Search Report for PCT/03/30666 dated Dec. 15, 2004.
U.S. Appl. No. 09/943,733, filed Aug. 31, 2001.
U.S. Appl. No. 10/065,280, filed Sep. 30, 2002.
U.S. Appl. No. 10/065279, filed Sep. 30, 2002.
U.S. Appl. No. 10/065,278, filed Sep. 30, 2002.
U.S. Appl. No. 11/307,901, filed Feb. 27, 2006.
U.S. Appl. No. 11/307,900, filed Feb. 27, 2006.
U.S. Appl. No. 11/968,494, filed Jan. 2, 2008.
U.S. Appl. No. 11/968,496, filed Jan. 2, 2008.
U.S. Appl. No. 12/849,991, filed Aug. 4, 2010.
U.S. Appl. No. 12/850,035, filed Aug. 4, 2010.
U.S. Appl. No. 12/850,063, filed Aug. 4, 2010.
U.S. Appl. No. 13/335,220, filed Dec. 22, 2011.
Communication from EPO re: 10000486 dated Apr. 4, 2011.
European Search Report re: EP05025816 dated Jun. 23, 2006.
European Search Report for EP07016222 dated Jan. 7, 2008.
European Search Report re: EP10000486 dated Apr. 23, 2010.
European Search Report for EP10011869 dated Jan. 20, 2011.
International Preliminary Examination Report re: PCT/US1998/10478 dated Dec. 11, 1999.
International Preliminary Report re: PCT/US2008/060127 dated Oct. 13, 2009.
International Preliminary Report re: PCT/US2009/040545 dated Oct. 19, 2010.
International Search Report for PCT/US1998/10478 dated Sep. 23, 1998.

(56) References Cited

OTHER PUBLICATIONS

International Search Report for PCT/US2003/25088 dated Dec. 29, 2003.
International Search Report for PCT/US2009/040545 dated Oct. 29, 2009.
Partial European Search Report re: EP05025816 dated Mar. 20, 2006.
Supplementary European Search Report re: EP98923664 dated Jun. 12, 2001.
Supplementary European Search Report re: EP03785177 dated May 19, 2009.
U.S. Appl. No. 08/859,887, filed May 21, 1997.
U.S. Appl. No. 09/896,455, filed Jun. 29, 2001.
U.S. Appl. No. 09/919,750, filed Jul. 31, 2001.
U.S. Appl. No. 10/216,516, filed Aug. 9, 2002.
U.S. Appl. No. 10/914,755, filed Aug. 9, 2004.
U.S. Appl. No. 10/941,347, filed Sep. 15, 2004.
U.S. Appl. No. 11/154,230, filed Jun. 16, 2005.
U.S. Appl. No. 11/154,863, filed Jun. 16, 2005.
U.S. Appl. No. 11/440,621, filed May 25, 2006.
U.S. Appl. No. 11/440,631, filed May 25, 2006.
U.S. Appl. No. 12/119,749, filed May 13, 2008.
U.S. Appl. No. 12/340,530, filed Dec. 19, 2008.
U.S. Appl. No. 12/495,497, filed Jun. 30, 2009.
U.S. Appl. No. 61/357,018, filed Jun. 21, 2010.
U.S. Appl. No. 12/849,960, filed Aug. 4, 2010.
U.S. Appl. No. 12/849,969, filed Aug. 4, 2010.
U.S. Appl. No. 12/849,977, filed Aug. 4, 2010.
U.S. Appl. No. 12/849,983, filed Aug. 4, 2010.
CCPR Centro De Cirurgia Plastica e Reabilitacao 'Up Lifting (Aptos Threads) http://ccpr.com.br/up1-1.htm, Aug. 19, 2002 pp. 1-2.
Datillo, Jr., P.P. 'Knotless Bi-directional Barned Absorbable Surgical Suture' Dissertation submitted to the Graduate Faculty of North Carolina State University Textile Management and Technology Nov. 2002, 75 pages.
Declaration of Dr. Gregory L. Ruff, dated Aug. 19, 2005, 8 pages, with Exhibits A-E.
Serafetinides, AA 'Short pulse laser beam interactions with polymers biocompatible materials and tissue' Proce SPIE vol. 3052 (1996) pp. 111-123.
Sulzle, Inc. B.G. et al Drilled End Surgical Needles Jul. 2002 Syracuse, New York.
European Search Report for EP09014651 dated Jan. 12, 2010.
European Search Report re: 10004453 dated Jun. 15, 2010.
European Search Report for EP10011872 dated Apr. 20, 2011.
European Search Report for EP10012437 dated Apr. 28, 2011.
European Search Report for EP10184766 dated Apr. 20, 2011.
International Preliminary Report re: PCT/US2008/087788 dated Jun. 22, 2010.
International Search Report for PCT/US1994/09631 dated Dec. 9, 1994.
International Search Report for PCT/US2002/20449 dated May 20, 2003.
International Search Report for PCT/US2003/030424 dated Nov. 1, 2004.
International Search Report for PCT/US2003/030664 dated May 25, 2004.
International Search Report re: PCT/US2003/030674 dated Sep. 2, 2004.
International Search Report re: PCT/US2004/014962 dated Feb. 24, 2005.
International Search Report for PCT/US2005/017028 dated Mar. 26, 2008.
International Search Report for PCT/US2007/002688 dated Oct. 22, 2007.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/034703 dated Sep. 28, 2009.
International Search Report for PCT/US2009/063081 dated Aug. 2, 2010.
International Search Report for PCT/US2009/041685 dated Dec. 22, 2009.
International Search Report for PCT/US2009/044274 dated Jan. 15, 2010.
International Search Report for PCT/US2010/056898 dated Aug. 2, 2011.
International Search Report for PCT/US2010/060889 dated Oct. 11, 2011.
International Search Report for PCT/US2011/034660 dated Feb. 8, 2012.
International Search Report for PCT/US2011/035270 dated Jan. 12, 2012.
International Search Report for PCT/US2011/035271 dated Jan. 12, 2012.
International Search Report re: PCT/US2011/035431 dated Jan. 12, 2012.
International Search Report re: PCT/US2011/040014 dated Feb. 9, 2012.
International Search Report for PCT/US2011/059238 dated May 21, 2012.
International Search Report for PCT/US2011/060069 dated May 18, 2012.
International Search Report for PCT/US2012/030441 dated Sep. 27, 2012.
Supplementary European Search Report re: EP03752630 dated Nov. 17, 2005.
Supplementary European Search Report re: 03770556 dated Nov. 17, 2005.
Supplementary European Search Report re: 03754965 dated Nov. 18, 2005.
Supplementary European Search Report re: 05750101 dated Apr. 7, 2010.
Supplementary European Search Report re: 07017663 dated Nov. 7, 2007.
Up Lifting (Aptos Threads), http://www.ccpr.com.br/upl-l.htm Aug. 19, 2002 pp. 1-2.
US 6,447,535, 09/2002, Jacobs (withdrawn)
US 6,503,260, 01/2003, Schaller (withdrawn)

* cited by examiner

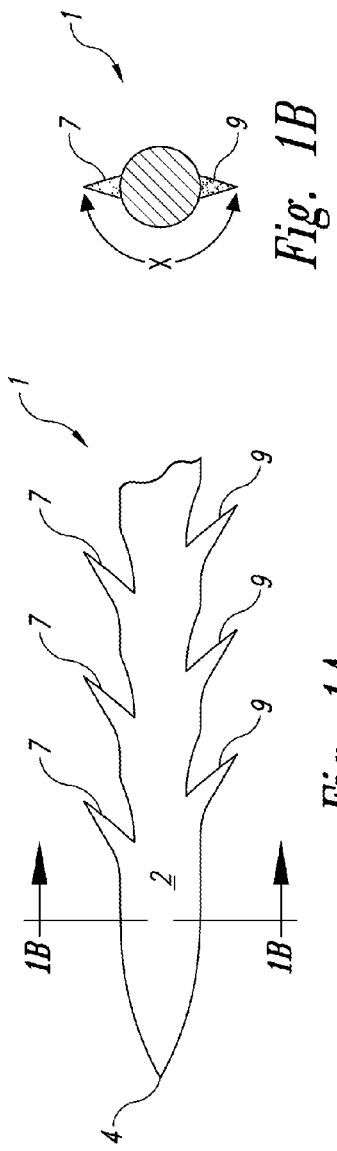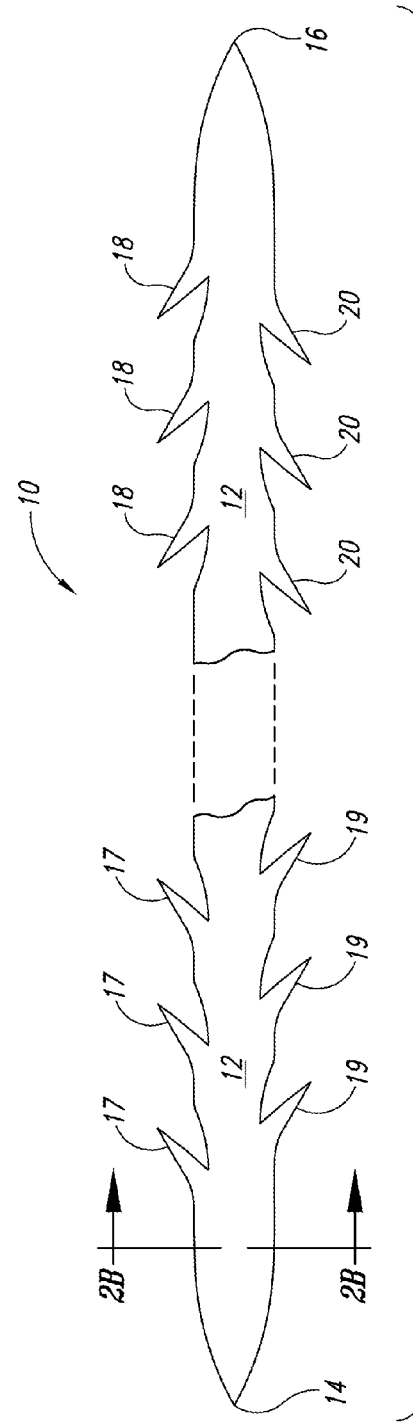

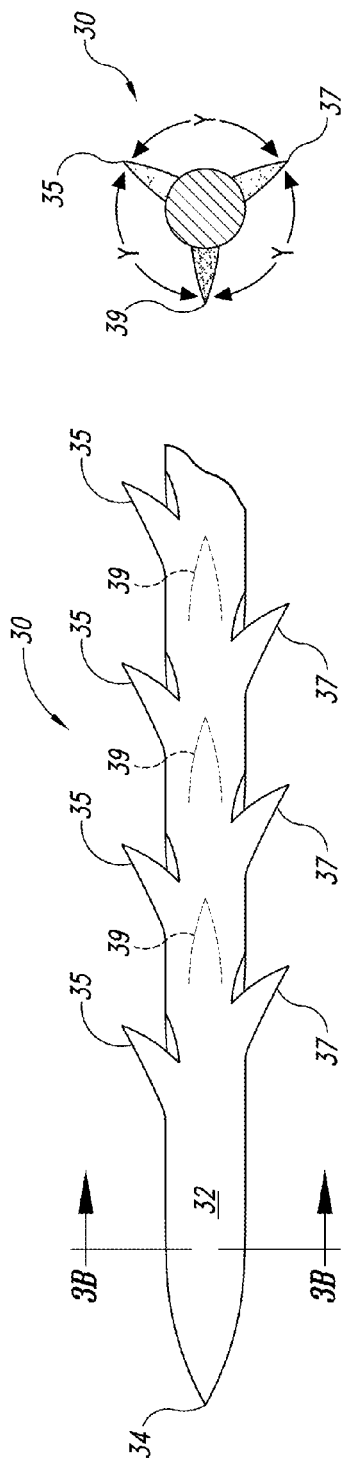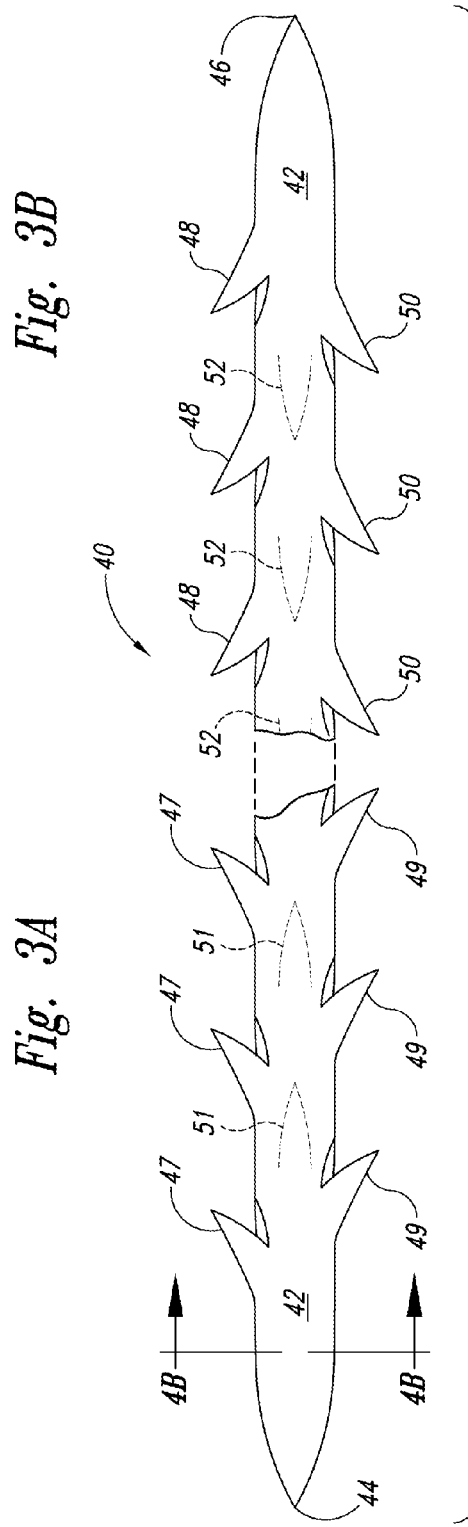
Fig. 3A  Fig. 3B
Fig. 4A  Fig. 4B

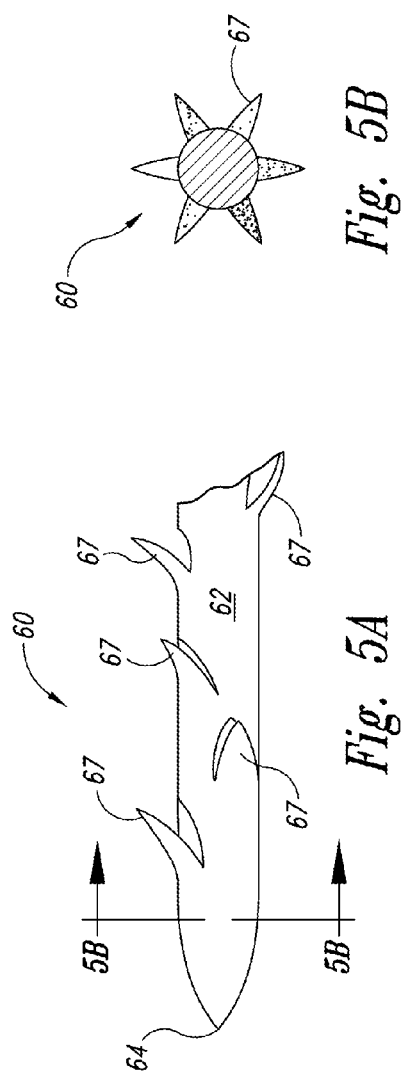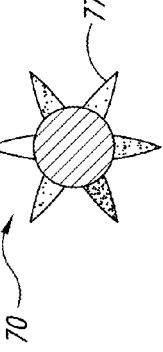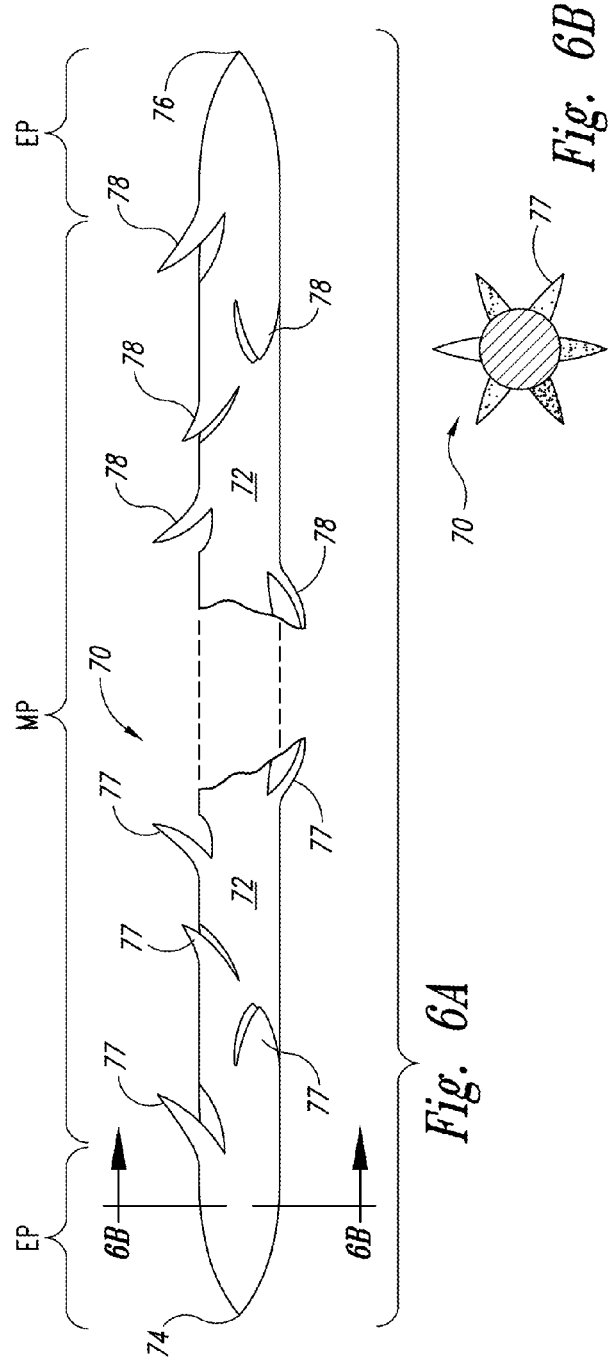

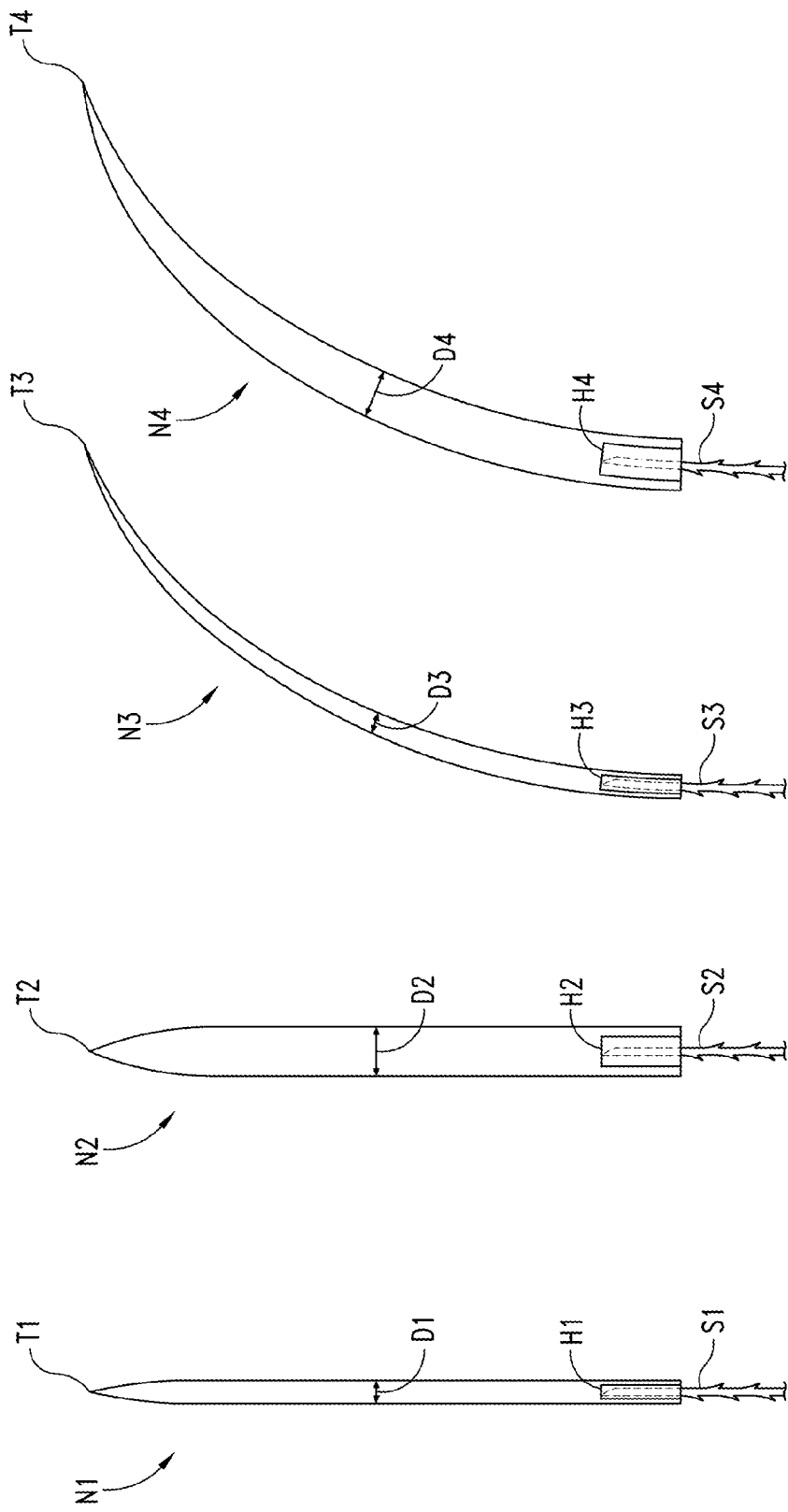

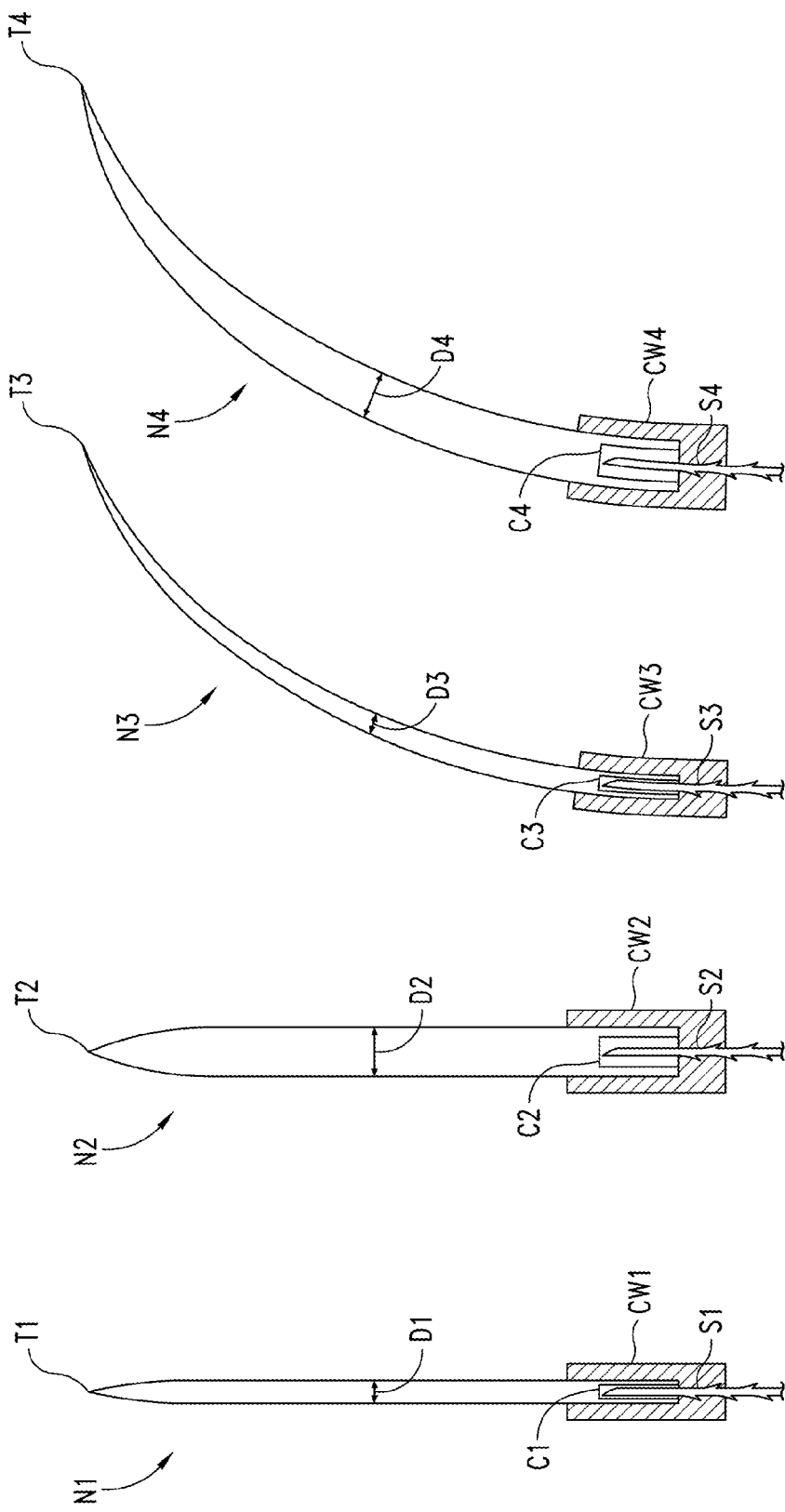

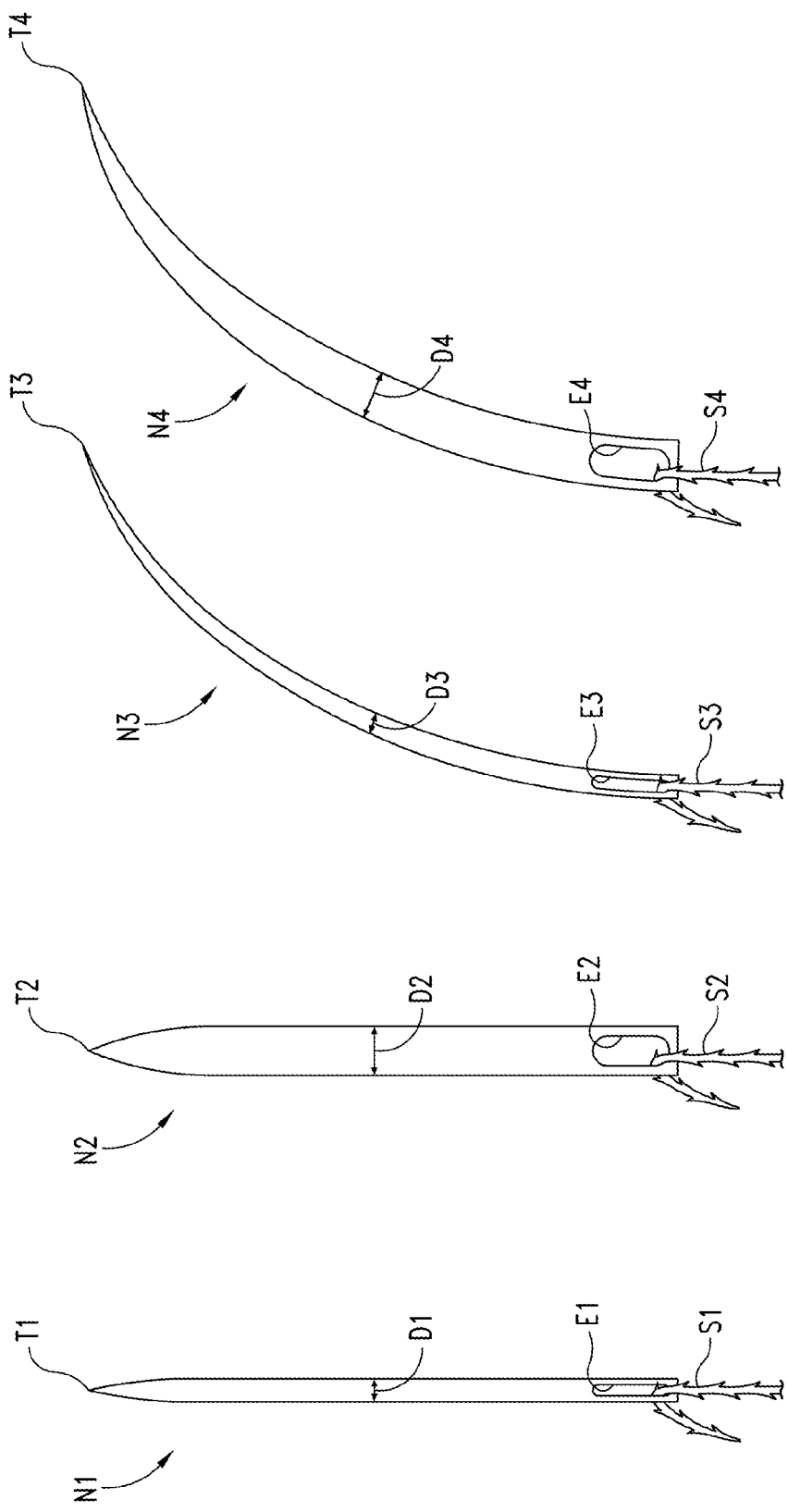

BARBED SUTURE IN COMBINATION WITH SURGICAL NEEDLE

CROSS-REFERENCE TO RELATED APPLICATIONS

This application is continuation of pending U.S. application Ser. No. 11/307,901, filed Feb. 27, 2006; which is a continuation application of U.S. patent application Ser. No. 10/065,278, filed Sep. 30, 2002, the entire contents of which are incorporated herein by reference.

TECHNICAL FIELD

This invention relates, in general, to a barbed suture useful for connecting bodily tissue in various surgical contexts, and more particularly, to the optimization of the disposition and/or configuration of the barbs on such barbed sutures.

BACKGROUND OF THE INVENTION

Various surgical methods employing sutures have been used in the past for closing or binding together wounds in human or animal tissue, such as skin, muscles, tendons, internal organs, nerves, blood vessels, and the like. More specifically, the surgeon may use a surgical needle with an attached conventional suture (which can be a smooth monofilament or can be a multi-filament) to pierce the tissue alternately on opposing faces of the wound and thus sew the wound closed. Whether the wound is accidental or surgical, loop stitching is the method often used, especially for surface wounds. The surgical needle is then removed and the ends of the suture are tied, typically with at least three overhand throws to form a knot.

As is well known, conventional sutures can be of non-absorbable material such as silk, nylon, polyester, polypropylene, or cotton, or can be of bio-absorbable material such as glycolic acid polymers and copolymers or lactic acid polymers and copolymers.

Since the time of their conception, barbed sutures, which are generally of the same materials as conventional sutures, have offered numerous advantages over closing wounds with conventional sutures. A barbed suture includes an elongated body that has one or more spaced barbs, which project from the body surface along the body length. The barbs are arranged to allow passage of the barbed suture in one direction through tissue but resist movement of the barbed suture in the opposite direction. Thus, the main advantage of barbed sutures has been the provision of a non-slip attribute. Accordingly, barbed sutures do not have to be knotted, like conventional sutures. Like a conventional suture, a barbed suture may be inserted into tissue using a surgical needle.

For instance, U.S. Pat. No. 3,123,077 to Alcamo describes an elongated cord for sewing human flesh, where the cord has a body portion and sharp-edged, resilient barbs projecting from the body at acute angles relative to the body. The barbed suture can be passed through tissue in one direction, but resists movement in the opposite direction.

Sutures with barbs disposed in a bi-directional arrangement, also called double-armed sutures, are shown in U.S. Pat. No. 5,931,855 to Buncke and U.S. Pat. No. 6,241,747 to Ruff. More particularly, the suture has barbs facing toward one end of the suture for about half the suture length and barbs facing in the opposite direction toward the other end of the suture for the other half of the suture length. This arrangement allows the barbs to move in the same direction as each respective suture end is inserted into the first and second sides of a wound. Such bi-directional barbed sutures not only are especially suitable for closing wounds with edges prone to separation, but also obviate the need to secure suture ends together with knotted loops.

Of interest is European Published Patent Application No. 1,075,843 A1 to Sulamanidze and Mikhailov, published Feb. 2, 2001, derived from PCT/RU99/00263 (published as WO 00/51658 on Sep. 8, 2000), priority to RU 99103732 (Mar. 3, 1999), which shows conical barbs arranged sequentially along the length of a thread and oriented in a direction opposite to that of the thread tension, with the distance between barbs being not less than 1.5 times the thread diameter.

Also of interest is U.S. Pat. No. 5,342,376 to Ruff. This patent shows an insertion device that is useful for positioning a barbed suture in order to close a wound. The insertion device has a tubular body for receiving a barbed suture, and preferably also has a handle to facilitate manipulation of the device by the surgeon. The insertion device is recommended for use with a barbed suture where the suture portion being inserted includes barbs facing a direction opposed to the direction of insertion. Such sutures with barbs opposing the direction of insertion are also shown in '376 to Ruff.

The disclosures of all patents and patent applications mentioned here are incorporated by reference.

Escarpment of barbs into a monofilament, depending on the barb cut depth, reduces the straight pull tensile strength since the effective suture diameter is decreased. However, the straight pull tensile strength of a barbed suture should be compared to the minimum knot pull strength of a conventional suture (a non-barbed suture) in accordance with the United States Pharmacopoeia since failure of conventional sutures (which have to be knotted and must meet a minimum knot pull tensile strength) occurs most frequently at the knot due to increased local stress.

To optimize the performance of a barbed suture, it is advantageous to consider varying the barb geometry (barb cut angle, barb cut depth, barb cut length, barb cut distance, etc.) and/or the spatial arrangement of the barbs. This should not only enhance the tensile strength of a barbed suture, but also should enhance the ability of a barbed suture in holding and maintaining wound edges together. Unlike conventional sutures, which place tensions directly at the knots, barbed sutures can spread out the tension along the escarped suture length, often evenly along the length. Optimizing the disposition and/or the configuration of the barbs should therefore further increase the effectiveness of the new barbed suture in maximizing the holding strength and minimizing the gap formation along the wound edges. The latter is particularly beneficial for promoting wound healing.

Also, such new barbed sutures should approximate tissue quickly with appropriate tension, alleviate distortion of tissue, and help to minimize scarring, due to the self-retaining benefits imparted by the barbs. The new barbed sutures would be especially useful in surgeries where minimization of scarring is imperative, such as cosmetic surgery, as well as in surgeries where space is limited, such as endoscopic surgery or microsurgery.

SUMMARY OF THE INVENTION

Accordingly, the present invention provides a barbed suture for connecting human or animal tissue. The barbed suture comprises an elongated body having a first end and a second end. The barbed suture further comprises a plurality of barbs projecting from the body. Each barb is adapted for enabling the barbed suture to resist movement, when in tissue, in the direction that is opposite from the direction in which that barb faces. The barbed suture further comprises the barbs being disposed on the body in a disposition selected from a staggered disposition, a twist cut multiple spiral disposition, an overlapping disposition, a random disposition, or combinations thereof.

For the staggered disposition, the twist cut multiple spiral disposition, and/or the overlapping disposition, the barbs may all be facing toward only one of the first and second ends. Alternatively, the barbed suture may have at least a first portion and a second portion, where the barbs of the first portion are facing toward the first end and the barbs of the second portion are facing toward the second end.

Also, in an alternative embodiment, the present invention provides a barbed suture for connecting human or animal tissue, where the suture comprises an elongated body having a first end and a second end. The suture further comprises a plurality of barbs projecting from the body. Each barb is adapted for enabling the suture to resist movement, when the suture is in tissue, in the direction that is opposite from the direction in which that barb faces. The suture further comprises the barbs having a configuration selected from a barb cut angle θ ranging from about 140 degrees to about 175 degrees, a barb cut depth with a ratio of cut depth to suture diameter ranging from about 0.05 to about 0.6, a barb cut length with a ratio of cut length to suture diameter ranging from about 0.2 to about 2, a barb cut distance with a ratio of cut distance to suture diameter ranging from about 0.1 to about 6, a corrugated underside, an arcuate base, varying sizes, or combinations thereof.

For the twist cut multiple spiral disposition, the barbed suture preferably has a spirality α angle ranging from about 5 degrees to about 25 degrees.

For the overlapping disposition, it is meant that at least two adjacent barbs are disposed where one overlaps the other. During escarpment of the barbs, the overlapping is created by a barb (i.e., the overlapping barb) being escarped into the topside of another adjacent barb (i.e., the overlapped barb), and so on. Hence, part of the topside of the overlapped barb becomes part of the underside of the overlapping barb, and so on. Thus, with the overlapping disposition, the barb cut distance between the overlapping barb and the overlapped barb may be shorter than the barb cut length of overlapped second barb, whereas, in general for barbed sutures, the barb cut distance between two barbs≥the barb cut length.

In still another embodiment, the present invention provides a barbed suture for connecting human or animal tissue in combination with a surgical needle, where the combination comprises a barbed suture attached to a surgical needle. The suture comprises a plurality of barbs projecting from an elongated body having a first end and a second end. Each barb is adapted for enabling the suture to resist movement, when the suture is in tissue, in the direction that is opposite from the direction in which that barb faces. The ratio of the surgical needle diameter to the suture diameter preferably is about 3:1 or less. Suitably, any of the inventive barbed sutures described here may be attached to a surgical needle.

BRIEF DESCRIPTION OF THE DRAWINGS

FIG. 1A is a side view of one embodiment of the present invention, showing a barbed suture with barbs disposed in a 180 degree staggered spacing;

FIG. 1B is a sectional view along line 1B-1B of the barbed suture in FIG. 1A;

FIG. 2A is a side view of another embodiment of the present invention, showing a barbed suture that is bi-directional with barbs disposed in a 180 degree staggered spacing;

FIG. 2B is a sectional view along line 2B-2B of the barbed suture in FIG. 2A;

FIG. 3A is a side view of another embodiment of the present invention, showing a barbed suture with barbs disposed in a 120 degree staggered spacing;

FIG. 3B is a sectional view along line 3B-3B of the barbed suture in FIG. 3A;

FIG. 4A is a side view of another embodiment of the present invention, showing a barbed suture that is bi-directional with barbs disposed in a 120 degree staggered spacing;

FIG. 4B is a sectional view along line 4B-4B of the barbed suture in FIG. 4A;

FIG. 5A is a side view of another embodiment of the present invention, showing a barbed suture with barbs disposed in a twist cut multiple spiral disposition;

FIG. 5B is a sectional view along line 5B-5B of the barbed suture in FIG. 5A;

FIG. 6A is a side view of another embodiment of the present invention, showing a barbed suture that is bi-directional with barbs disposed in a twist cut multiple spiral disposition;

FIG. 6B is a sectional view along line 6B-6B of the barbed suture in FIG. 6A;

FIGS. 13A, 13B, 13C, and 13D show various surgical needles, where a barbed suture is attached to each surgical needle.

FIGS. 15A, 15B, 15C, and 15D show various surgical needles, where a barbed suture is attached to each surgical needle by channel wrapping.

FIGS. 16A, 16B, 16C, and 16D show various surgical needles, where a barbed suture is attached to each surgical needle by eyelet threading.

DESCRIPTION

Figure 7A:
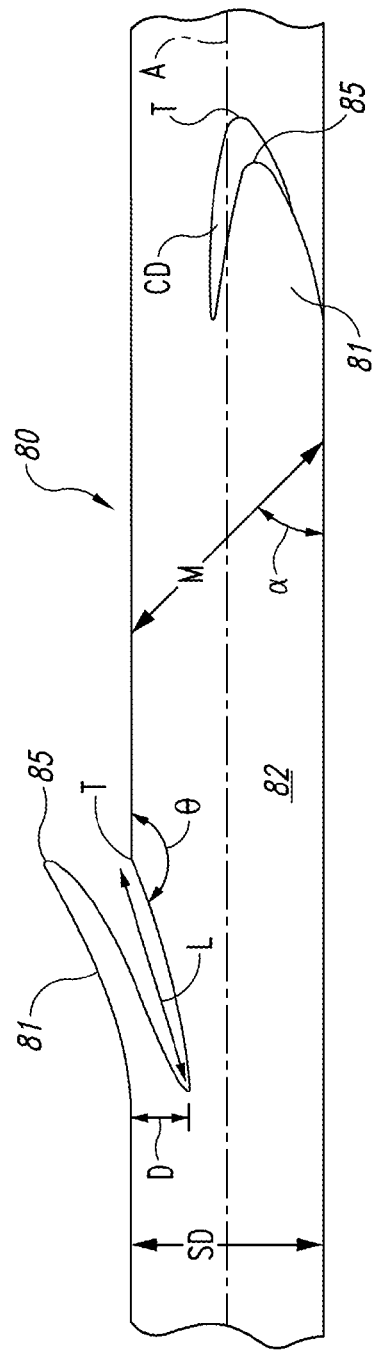
FIG. 7A is a sectional side view of a barbed suture, which is bi-directional with barbs disposed in a twist cut multiple spiral disposition like the barbed suture in FIG. 6A, but illustrated in an enlarged section.

As used here, the term "wound" means a surgical incision, cut, laceration, severed tissue or accidental wound in human or animal skin or other human or animal bodily tissue, or other condition in a human or animal where suturing, stapling, or the use of another tissue connecting device may be required.

Also as used here, the term "tissue" includes, but is not limited to, tissues such as skin, fat, fascia, bone, muscle, organs, nerves, or blood vessels, or fibrous tissues such as tendons or ligaments.

Moreover, the term "polymer" as used here generally includes, but is not limited to, homopolymers, copolymers (such as block, graft, random and alternating copolymers), terpolymers, et cetera, and blends and modifications thereof. Furthermore, the term "polymer" shall include all possible structures of the material. These structures include, but are not limited to, isotactic, syndiotactic, and random symmetries.

Although the sutures are described below in a preferred embodiment with a circular cross section, the sutures could also have a non-circular cross sectional shape that could increase the surface area and facilitate the formation of the barbs. Other cross sectional shapes may include, but are not limited to, oval, triangle, square, parallelepiped, trapezoid, rhomboid, pentagon, hexagon, cruciform, and the like. Typically, barbs are cut into a polymeric filament that has been formed by extrusion using a die with a circular cross section, and thus, the cross section of the filament will be circular, as that is what results during such extrusion. However, extrusion dies can be custom made with any desired cross-sectional shape.

Hence, the term "diameter" as used here is intended to mean the transverse length of the cross section, regardless of whether the cross section is circular or some other shape.

Suitable diameters for the inventive sutures described below may range from about 0.001 mm to about 1 mm, and of course, the diameter may be from about 0.01 mm to about 0.9 mm, or from about 0.015 mm to about 0.8 mm. The typical diameter ranges from about 0.01 mm to about 0.5 mm. The length of the suture can vary depending on several factors such as the length and/or depth of the wound to be closed, the type of tissue to be joined, the location of the wound, and the like. Typical suture lengths range from about 1 cm to about 30 cm, more particularly from about 2 cm to about 22 cm.

The terms "staggered" and "staggering" as used here in relation to the disposition of barbs on a suture are intended to mean that the suture has at least two sets of barbs that are offset with respect to each other, where the first set is aligned longitudinally on the suture and the second set is aligned longitudinally on the suture, but a plane perpendicular to the suture and cutting transversely through the suture and intersecting the base of a barb of the first set will not intersect the base of a barb of the second set.

The barbs project from the exterior surface of the suture body on which the barbs are disposed. Depending on the intended end use of the barbed suture, barbs of different sizes may be employed. In general, larger barbs are more suitable for joining certain types of tissue such as fat tissue or soft tissue. On the other hand, smaller barbs are more suitable for joining other types of tissue, such as collagen dense tissue.

As noted above, barbed sutures may be made from the same materials used for making conventional loop sutures. Any particular chosen material for the barbed suture depends on the strength and flexibility requirements.

More specifically, barbed sutures may be formed from a bio-absorbable material that allows the suture to degrade and thus to be absorbed over time into the tissue as the wound heals. Generally, bio-absorbable materials are polymeric, and depending on the particular polymer selected, the degradation time in the wound ranges from about 1 month to over 24 months. The use of bio-absorbable materials eliminates the necessity of removing the sutures from the patient.

Various bio-absorbable polymers include, but are not limited to, polydioxanone, polylactide, polyglycolide, polycaprolactone, and copolymers thereof. Commercially available examples are polydioxanone (sold as PDS II, a trade name used by Ethicon for selling surgical sutures), copolymer of about 67% glycolide and about 33% trimethylene carbonate (sold as MAXON®, a trademark registered to American Cyanamid for surgical sutures), and copolymer of about 75% glycolide and about 25% caprolactone (sold as MONOCRYL®, a trademark registered to Johnson & Johnson for sutures and suture needles). Barbed sutures made from such bio-absorbable materials are useful in a wide range of applications.

Additionally, barbed sutures may be formed from a non-absorbable material, which may be a polymer. Such polymers include, but are not limited to, polypropylene, polyamide (also known as nylon), polyester (such as polyethylene terephthlate, abbreviated here as PET), polytetrafluoroethylene (such as expanded polytetrafluoroethylene, abbreviated here as ePTFE and sold by Gore as GOR-TEX®), polyetherester (such as polybutester, which is the condensation polymerization of dimethyl terephthlate, polytetramethylene ether glycol, and 1,4-butanediol, and which is marketed by Davis & Geck and by U.S. Surgical, companies owned by Tyco, under the name NOVAFIL®, which is a trademark registered to American Cyanamid for surgical sutures), or polyurethane. Alternatively, the non-absorbable material may be metal (e.g., steel), metal alloys, natural fiber (e.g., silk, cotton, et cetera), and the like.

Most of the barbed sutures discussed below are described as having their ends being pointed and formed of a material sufficiently stiff to allow for piercing tissue. It is contemplated that the ends of the barbed sutures may comprise a surgical needle. In this embodiment, the barbed suture is adapted for attachment, such as by swaging, channel wrapping, heat shrinking, or eyelet threading to the surgical needle for insertion into tissue.

Attachment by swaging is well described and is typically accomplished by inserting the suture end into the surgical needle hole that is longitudinally disposed at one end of the surgical needle (usually the hole has been drilled longitudinally into one end of the needle), followed by crimping the resultant about the needle hole so that the suture is secured to the surgical needle for insertion into tissue. Also, some surgical needles with a longitudinal hole in one end are heat-shrinkable tubes that are heat shrunk after insertion of the suture in order to attach the suture to the surgical needle. Additionally, some surgical needles have a channel or trough at one end, and the suture is laid in the trough, followed by wrapping to secure the suture to the surgical needle. Surgical needles with a conventional eyelet type of hole transversely disposed in one end of the surgical needle could also be used, but are not preferred for barbed sutures. For the present invention, part of the discussion below regards surgical needles swaged with barbed sutures, but it is contemplated that any other suitable means of attaching needles can be employed.

Attachment of sutures and surgical needles is described in U.S. Pat. No. 3,981,307 Borysko, U.S. Pat. No. 5,084,063 to Korthoff, U.S. Pat. No. 5,102,418 to Granger et al., U.S. Pat. No. 5,123,911 to Granger et al., U.S. Pat. No. 5,500,991 to Demarest et al., U.S. Pat. No. 5,722,991 to Colligan, U.S. Pat. No. 6,012,216 to Esteves et al., and U.S. Pat. No. 6,163,948 to Esteves et al. A method for the manufacture of surgical needles is described in U.S. Pat. No. 5,533,982 to Rizk et al. Further, it is noted that the surgical needle may be coated, the coating allowing for the needle of the inventive combination surgical needle/barbed suture to be inserted into tissue with less force than if the surgical needle were not coated. The coating may be a polymer, for instance, a silicone resin coating. For example, an improved siliconized surgical needle that requires significantly less force to effect tissue penetration than a standard siliconized surgical needle is described in U.S. Pat. No. 5,258,013 to Granger et al.

The barbs are disposed in various arrangements on the body of the suture. The barbs may be formed using any suitable method, including injection molding, stamping, cutting, laser, and the like. With regard to cutting, in general, polymeric threads or filaments are purchased, and then the barbs are cut onto the filament body.

The cutting may be manual, but that is labor intensive and not cost effective.

A very suitable cutting machine is disclosed in U.S. patent application Ser. No. 09/943,733 to Genova et al., assignors to Quill Medical, filed Aug. 31, 2001, the disclosure of which is incorporated by reference. Such a cutting machine has a plurality of blades for escarpment of barbs onto a suture filament. A typical cutting machine for manufacturing barbed sutures utilizes a cutting bed, a vise, one or more blade assemblies, and sometimes a template or guide for the blades. The suture filament is placed in the bed and held by the vise, with the transverse direction of the blades generally disposed in the transverse direction of the suture filament, in order to cut a plurality of axially spaced barbs disposed on the exterior of a suture filament.

With reference now to the drawings, where like reference numerals designate corresponding or similar elements throughout the several views, shown in FIG. 1A is a side view of a barbed suture according to the present invention and generally designated at 1.

Suture 1 includes elongated body 2 that is generally circular in cross section and that terminates in end 4. End 4 is illustrated in one embodiment as being pointed for penetrating tissue, but it is contemplated that end 4 may comprise a surgical needle (not shown) for insertion into tissue. (The other end is not shown.) Also, suture 1 includes plurality of closely spaced barbs 7, 9 arranged in a staggered uni-directional disposition. More specifically, axially spaced barbs 7 are radially arranged about 180 degrees from and staggered with respect to axially spaced barbs 9, with barbs 7, 9 facing pointed end 4. First set of barbs 7 define a plane that is substantially coplanar with the plane defined by second set of barbs 9, and consequently, barbs 7, 9 define substantially the same one plane due to the radial 180 degree arrangement.

FIG. 1B, which is a cross sectional view along line 1B-1B of suture 1 in FIG. 1A, more clearly illustrates angle X, namely the radial 180 degree arrangement of barbs 7 with respect to barbs 9. As also can be seen from FIG. 1B, the stippling illustrates that first barb 7 of barbs 7 is closer to pointed end 4 (not shown in FIG. 1B), and thus, seems to be larger than farther away first barb 9 of barbs 9, due to the staggering. A transverse plane that is perpendicular to suture body 2 and that intersects the base of one barb 7 of barbs 7 does not intersect the base of any barb 9 of barbs 9.

Suture 1 may be made with a cutting machine that produces two sets of barbs 7, 9, usually one set at a time, in a staggered position along suture 1, such as the cutting device described in the above-noted Ser. No. 09/943,733 to Genova et al.

First set of barbs 7 is created by placing and holding a suture filament in the vise, and then, the set of blades, with a predetermined length, splices into the suture filament at an angle selected to create barbs 7 pointing in one direction toward pointed end 4. Second set of barbs 9 is created similarly after offsetting the blades longitudinally (to create the staggering) approximately half of the longitudinal distance between two of barbs 7 and also rotating the suture filament about 180 degrees on the vise, which is equipped to accommodate first set of barbs 7 that are already cut.

Shown in FIG. 2A is suture 10, which is another embodiment of the present invention and is like suture 1, except that suture 10 is bi-directional. Suture 10 includes elongated body 12 that is generally circular in cross section. Elongated body 12 terminates in first and second pointed ends 14, 16 for penetrating tissue. Also, it is contemplated that one or both ends 14, 16 may comprise a surgical needle (not shown) for insertion into tissue. Also, suture 10 includes plurality of closely spaced barbs 17, 18, 19, 20 arranged in a staggered bi-directional disposition.

More specifically, plurality of axially spaced barbs 17 are radially arranged about 180 degrees from and staggered with respect to plurality of axially spaced barbs 19, with barbs 17, 19 facing pointed end 14 for a portion (about half of the length) of suture 10. Similarly, plurality of axially spaced barbs 18 are radially arranged about 180 degrees from and staggered with respect to plurality of axially spaced barbs 20, with barbs 18, 20 facing pointed end 16 for another portion (approximately the other half of the length) of suture 10. First set of barbs 17, 18 define a plane that is substantially coplanar with the plane defined by second set of barbs 19, 20. As a result, all of barbs 17, 18, 19, 20 define substantially the same one plane due to the radial 180 degree arrangement of first set of barbs 17, 18 with respect to second set of barbs 19, 20.

FIG. 2B is a cross sectional view along line 2B-2B of suture 10 in FIG. 2A, more clearly illustrating angle X, namely the radial 180 degree arrangement. Due to the staggering, first barb 17 of barbs 17 is closer to pointed end 14 (not shown in FIG. 2B), and thus, appears larger than farther away first barb 19 of barbs 19, as is illustrated by the stippling. A transverse plane that is perpendicular to suture body 12 and that intersects the base of one barb 17 of barbs 17 does not intersect the base of any barb 19 of barbs 19. Likewise, a transverse plane that is perpendicular to suture body 12 and that intersects the base of one barb 18 of barbs 18 does not intersect the base of any barb 20 of barbs 20.

Suture 10 may be made with the same cutting machine as suture 1, such as the cutting device described in the above-noted Ser. No. 09/943,733 to Genova et al., except with the following change in blade direction.

For first set of bi-directional barbs 17, 18, after the suture filament is placed and held in the vise, the blades splice with a first cutting action into approximately half of the length of the suture filament to create barbs 17 facing in one direction toward pointed end 14. Next, the blades are rotated 180 degrees so that they are now disposed in the opposite direction and over the uncut half of the length. The blades are then allowed to splice into the other half of the length of the suture filament with a second cutting action to create barbs 18 facing in the opposite direction toward pointed end 16.

Next, the blades are offset longitudinally (to create the staggering) about half of the longitudinal distance between two of barbs 17, and also the suture filament is rotated about 180 degrees on the vice, which is equipped to accommodate first set of bi-directional barbs 17, 18 that are already cut. Then, for second set of bi-directional barbs 19, 20, the blades splice with a first cutting action into approximately half the length of the suture filament to create barbs 20 facing in one direction toward pointed end 16. The first cutting action is followed by rotating the blades longitudinally 180 degrees so that they are now disposed in the opposite direction and over the uncut half of the length. The blades are then allowed to splice into the other half of the length of the suture filament with a second cutting action to create barbs 19 facing in the opposite direction toward pointed end 14.

In an alternative embodiment (not shown) for bi-directional suture 10, the portion of suture 10 with barbs 17, 19 may have them facing toward pointed end 16 and the portion of suture 10 with barbs 18, 20 may have them facing toward pointed end 14. With this variation, the barbed suture would be inserted into tissue with an insertion device, such as that shown in the above-noted U.S. Pat. No. 5,342,376 to Ruff. Additionally, it is noted that, if desired, barbs may be escarped so that there may be two portions with barbs facing one end and one portion with barbs facing the other end, or two portions with barbs facing one end and two portions with barbs facing the other end, and so on (not shown), and thus, if a portion of barbs is not facing the suture end to which those barbs are adjacent, then, the barbed suture would be inserted into tissue with an insertion device.

An advantage of a barbed suture having a radial 180 degree arrangement with staggering is that the 180 degree spacing is readily fabricated on relatively small diameter filaments and the staggering improves anchoring performance. Thus, in thin and delicate tissue, where a smaller suture is desirable, the staggered 180 degree spacing generates effective anchoring performance.

Turning now to FIG. 3A, depicted is a side view of another embodiment of a suture according to the present invention, and generally designated at suture 30. Suture 30 is like suture 1 shown in FIG. 1A, except that the radial spacing for suture 30 is 120 degrees instead of 180 degrees as is shown for suture 1.

More particularly, suture 30 includes elongated body 32 that is generally circular in cross section and that terminates in pointed end 34 for penetrating tissue. It is contemplated that end 34 may comprise a surgical needle (not shown) so that the suture can be inserted into tissue. (The other end is not shown.) Additionally, suture 30 includes plurality of closely spaced barbs 35, 37, 39 arranged so that all face in the same direction toward pointed end 34. Hence, the disposition of barbs 35, 37, 39 is uni-directional.

Also, axial spaced barbs 35 are radially arranged about 120 degrees from and staggered with respect to axially spaced barbs 37, which are radially arranged about 120 degrees from and staggered with respect to axially spaced barbs 39. Hence, axially spaced barbs 39 are also arranged about 120 degrees from and staggered with respect to axially spaced barbs 35. As a result of the radial 120 degree arrangement, first set of barbs 35 define substantially the same one plane; second set of barbs 37 define substantially another same one plane; and third set of barbs 39 define substantially still another same one plane. Thus, suture 30 has barbs 35, 37, 39 arranged in a staggered uni-directional 120 degree disposition.

FIG. 3B is a cross sectional view along line 3B-3B of suture 30 in FIG. 3A and shows with more particularity angle Y, namely the radial 120 degree arrangement of barbs 35 with respect to barbs 37, barbs 37 with respect to barbs 39, and barbs 39 with respect to barbs 35.

As illustrated by the stippling, first barb 35 of barbs 35, because of the staggering, is closer to pointed end 34 (not shown in FIG. 3B), and thus, seems to be larger than farther away first barb 37 of barbs 37. Also, first barb 37 of barbs 37, due to the staggering, is closer to pointed end 34 (not shown in FIG. 3B), and thus, seems to be larger than even farther away first barb 39 of barbs 39. A transverse plane that is perpendicular to suture body 32 and that intersects the base of one barb 35 of barbs 35 does not intersect the base of any barb 37 of barbs 37. Likewise, a transverse plane that is perpendicular to suture body 32 and that intersects the base of one barb 37 of barbs 37 does not intersect the base of any barb 39 of barbs 39. Similarly, a transverse plane that is perpendicular to suture body 32 and that intersects the base of one barb 39 of barbs 39 does not intersect the base of any barb 35 of barbs 35.

Suture 30 may be made with the same cutting machine as suture 1, such as the cutting device described in the above-noted Ser. No. 09/943,733 to Genova et al. The cutting machine is now used to produce three sets of barbs 35, 37, 39, usually one set at a time, in a staggered position along suture 30.

First set of barbs 35 is created by placing and holding a suture filament in the vise, followed by the blades, after having been adjusted to a predetermined length, splicing into the suture filament at an angle that is chosen to create barbs 35 so that all are facing in the same direction toward pointed end 34.

Next, the blades are offset longitudinally (to create the staggering) approximately half of the longitudinal distance between two of barbs 35. Also, the filament is rotated about 120 degrees on the vise, which is equipped to accommodate first set of barbs 35 that have already been cut, and then second set of barbs 37 is created in a similar manner.

Likewise, the blades are again offset longitudinally (to create the staggering) approximately half the longitudinal distance between two of barbs 35, and also the suture filament is rotated about 120 degrees on the vise, which is equipped to accommodate both already cut first set of barbs 35 and already cut second set of barbs 37. Following the longitudinal movement and rotation, third set of barbs 39 is created in a similar manner.

Preferably, each successive barb is escarped at a position about 120 degrees around suture body 32 from the preceding barb and does not overlap with any other barb.

With reference now to FIG. 4A, illustrated is suture 40, another embodiment of the present invention. Suture 40 is similar to suture 30, except that suture 40 is bi-directional. Suture 40 includes elongated body 42 that is generally circular in cross section and that terminates in first and second pointed ends 44, 46 for penetrating tissue. Also, it is contemplated that one or both ends 44, 46 may comprise a surgical needle (not shown) in order to be inserted into tissue. Suture 40 further includes plurality of closely spaced barbs 47, 48, 49, 50, 51, 52 arranged in a staggered bi-directional disposition.

For about half of the length of suture 40, axially spaced barbs 47 are circumferentially arranged about 120 degrees from and staggered with respect to axially spaced barbs 49, which are radially arranged about 120 degrees from and staggered with respect to axially spaced barbs 51. Consequently, axially spaced barbs 51 are also arranged about 120 degrees from and staggered with respect to axially spaced barbs 47. Thus, a portion of suture 40 has all of barbs 47, 49, 51 facing in the same direction toward pointed end 44.

For the other half of the length of suture 40, axially spaced barbs 48 are radially arranged about 120 degrees from and staggered with respect to axially spaced barbs 50, which are radially arranged about 120 degrees from and staggered with respect to axially spaced barbs 52. Consequently, axially spaced barbs 52 are also arranged about 120 degrees from and staggered with respect to axially spaced barbs 48. Thus, another portion of suture 40 has all of barbs 48, 50, 52 facing in the same direction toward pointed end 46.

As a result of the radial 120 degree arrangement, first set of barbs 47, 48 define substantially the same one plane; second set of barbs 49, 50 define substantially another same one plane; and third set of barbs 51, 52 define substantially still another same one plane.

FIG. 4B, which is a cross sectional view along line 4B-4B of suture 40 in FIG. 4A, shows more clearly angle Y, namely the radial 120 arrangement with greater specificity. As illustrated by the stippling, first barb 47 of barbs 47, on account of the staggering, is closer to pointed end 44 (not shown in FIG. 4B), and thus, appears larger than farther away first barb 49 of barbs 49. Also because of the staggering, first barb 49 of barbs 49 is closer to pointed end 44 (not shown in FIG. 4B), and thus, appears larger than even farther away first barb 51 of barbs 51.

A transverse plane that is perpendicular to suture body 42 and that intersects the base of one barb 47 of barbs 47 does not intersect the base of any barb 49 of barbs 49. Likewise, a transverse plane that is perpendicular to suture body 32 and that intersects the base of one barb 49 of barbs 49 does not intersect the base of any barb 51 of barbs 51. Similarly, a transverse plane that is perpendicular to suture body 42 and that intersects the base of one barb 51 of barbs 51 does not intersect the base of any barb 47 of barbs 47. Also, a transverse plane that is perpendicular to suture body 42 and that intersects the base of one barb 48 of barbs 48 does not intersect the base of any barb 50 of barbs 50. Likewise, a transverse plane that is perpendicular to suture body 32 and that intersects the base of one barb 50 of barbs 50 does not intersect the base of any barb 52 of barbs 52. Similarly, a transverse plane that is perpendicular to suture body 42 and that intersects the base of one barb 52 of barbs 52 does not intersect the base of any barb 48 of barbs 48.

Suture 40 may be made with the same cutting machine as suture 1, such as the cutting device described in the above-noted Ser. No. 09/943,733 to Genova et al., except with the following change in blade direction.

For first set of bi-directional barbs 47, 48, after the suture filament is placed and held in the vise, the blades splice with a first cutting action into approximately half of the length of the suture filament to create barbs 47 facing in one direction toward pointed end 44. Then, the blades are rotated 180 degrees so that they are now disposed in the opposite direction and over the uncut half of the length. The blades then are allowed to splice into the other half of the length of the suture filament with a second cutting action to create barbs 48 facing in the opposite direction toward pointed end 46.

Next, the blades are offset longitudinally (to create the staggering) for about half the longitudinal distance between two of barbs 47, and also the suture filament is rotated about 120 degrees on the vise, which is equipped to accommodate first set of bi-directional barbs 47, 48 that are already cut. Then, for second set of bi-directional barbs 49, 50, the blades splice with a first cutting action into approximately half of the length of the suture filament to create barbs 50 facing in one direction toward pointed end 46. The first cutting action is followed by rotating the blades 180 degrees so that they are now disposed in the opposite direction and over the uncut half of the suture filament. They then splice into the other half of the length of the suture filament with a second cutting action to create barbs 49 facing in the opposite direction toward pointed end 44.

Then, the blades are again offset longitudinally (to create the staggering) for about half the longitudinal distance between two of barbs 47. Additionally, the suture filament again is rotated about 120 degrees on the vise, which is equipped to accommodate already cut first set of bi-directional barbs 47, 48 and already cut second set of bi-directional barbs 49, 50. Following the longitudinal movement and rotation, the third set of bi-directional barbs 51, 52 are made by having the blades splice with a first cutting action into approximately half of the length of the suture filament to create barbs 51 facing in one direction toward pointed end 44. The first cutting action is followed by rotating the blades 180 degrees so that they are now disposed in the opposite direction and over the uncut half of the suture filament. They next splice into the other half of the length of the suture filament with a second cutting action to create barbs 52 facing in the opposite direction toward pointed end 46.

Preferably, each successive barb is escarped at a position about 120 degrees around suture body 42 from the preceding barb and does not overlap with any other barb.

In an alternative embodiment (not shown) for bi-directional suture 40, the portion of suture 40 having barbs 47, 49, 51 may have them facing toward pointed end 46 and the portion of suture 40 having barbs 48, 50, 52 may have them facing toward pointed end 44. With this variation, the barbed suture would be inserted into tissue with an insertion device, such as that shown in the above-noted U.S. Pat. No. 5,342,376 to Ruff. Additionally, it is noted that, if desired, barbs may be escarped so that there may be two portions with barbs facing one end and one portion with barbs facing the other end, or two portions with barbs facing one end and two portions with barbs facing the other end, and so on (not shown), and thus, if a portion of barbs is not facing the suture end that those barbs are adjacent, then, the barbed suture would be inserted into tissue with an insertion device.

An advantage of a barbed suture with a radial 120 degree arrangement is that the barbs exert force in three distinct planes that compliment each other, resulting in maximization of the retention force of the suture overall. As noted above, the staggering enhances anchoring performance.

Turning now to FIG. 5A, shown is another embodiment of the present invention, which is generally designated at suture 60, with radial spacing that is in a twist cut multiple spiral. Suture 60 includes elongated body 62 of generally circular cross section. Elongated body 62 terminates in pointed end 64 for penetrating tissue. Also, it is contemplated that end 64 may comprise a surgical needle (not shown) for insertion into tissue. Furthermore, suture 60 includes plurality of closely spaced barbs 67 arranged in a twist cut multiple spiral pattern around body 62 and facing in the same direction toward pointed end 64.

FIG. 5B is a cross sectional view along line 5B-5B of suture 60 in FIG. 5A. Due to the twist cut multiple spiral disposition, each respective barb 67 seems to be smaller and smaller as each is farther and farther away from pointed end 64 (not shown in FIG. 5B), the illusion of size difference being illustrated by the stippling.

Suture 60 may be constructed with a similar cutting machine as that used for making suture 1, such as the cutting device described in the above-noted Ser. No. 09/943,733 to Genova et al. With a twist cutting method, barbs 67 may be produced in multiple spirals that preferably are created at the same time as the suture filament is held stationary, instead of being rotated, when the cutting takes place.

More particularly, a suture filament that is about 7 inches (about 178 mm) in length, is longitudinally twisted for a portion of the suture length, such as 39 times for a portion that is about 4.5 inches (about 114 mm) of the suture length. Thus, an end is secured, and the other end is grasped and rotated 360 degrees, 39 times, so the portion of the suture filament is twisted when the suture is then placed and held in the vise.

Twisting preferably is performed 28 to 50 times, and may be performed more or less, such as 19 to 70 times. Suitably, twisting may be from about 2 to about 17 twists per inch, or about 3 to about 15 twists per inch, or about 5 to about 13 twists per inch (per inch being per 25.4 mm).

Next, the blades, after having been adjusted to a predetermined length, simultaneously splice into the suture filament. The cutting action makes cuts to create barbs 67 so that all are facing in the same direction toward pointed end 64. After twist cut multiple spiral barbed suture 60 is released from the vice and untwisted, barbs 67 are disposed in multiple spirals on suture 60.

Turning now to FIG. 6A, shown is another embodiment of the present invention, which is generally designated at suture 70. Suture 70 is of a twist cut multiple spiral disposition and thus is similar to suture 60, except that suture 70 is bi-directional. Suture 70 includes elongated body 72 that is generally circular in cross section and that terminates in first and second pointed ends 74, 76 for penetrating tissue. It is contemplated that one or both of ends 74, 76 may comprise a surgical needle (not shown) for insertion into tissue.

Suture 70 further includes plurality of closely spaced barbs 77, 78 arranged in two respective spiral patterns, each being a multiple spiral around body 72. Barbs 77, 78 are disposed on middle portion MP that is approximately 3 inches (approximately 76 mm) of suture 70, with each end portion EP of suture 70 being barb-free. More particularly, plurality of barbs 77 are arranged in a multiple spiral pattern with all barbs 77 facing toward pointed end 74 for a part (about half) of middle portion MP along the length of suture 70. Similarly, plurality of barbs 78 are arranged in a multiple spiral pattern with all barbs 78 facing toward pointed end 76 for another part (the other approximate half) of middle portion MP along the length of suture 70.

FIG. 6B is a cross sectional view along line 6B-6B of suture 60 in FIG. 6A. Due to the multiple spiral configuration, each respective barb 77 seems to be smaller and smaller as each is farther and farther away from pointed end 74 (not shown in FIG. 6B), as illustrated by the stippling.

Suture 70 may be made with the same cutting machine as suture 60, such as the cutting device described in the above-noted Ser. No. 09/943,733 to Genova et al., but with the following change in blade direction. Using the twist cutting method, barbs 77 may be produced in multiple spirals that preferably are created at the same time, and then after the direction change for the blades, barbs 78 may be produced in multiple spirals that preferably are created at the same time. Thus during the cutting, the suture filament is held stationary instead of being rotated.

More specifically, a section of about 4.5 inches (about 114 mm) in length of a suture filament is twisted, such as 39 times for a suture about 7 inches (about 178 mm) in length. Thus, an end is secured, and the other end is grasped and rotated 360 degrees, 39 times, so the twisted section of the suture filament has about 8⅔ twists per inch (per 25.4 mm) when the suture filament is then placed and held in the vise.

Twisting preferably is performed 28 to 50 times, and may be performed more or less, such as 19 to 70 times. Suitably, twisting may be from about 2 to about 17 twists per inch, or about 3 to about 15 twists per inch, or about 5 to about 13 twists per inch (per inch being per 25.4 mm).

Next, the blades, after having been adjusted to a predetermined length, splice into approximately half of the approximately 3 inch (approximately 76 mm) length of middle portion MP of the approximately 4.5 inch (approximately 114 mm) twisted section of the suture filament in a first cutting action with the blades making cuts to create barbs 77 so that all are facing in one direction toward pointed end 74. Depending on how many blades there are on the cutting machine and how many barbs 77 are desired, there may be one cutting motion to cut all barbs 77 simultaneously, or there may be repeated cutting motions until the desired number of barbs 77 are escarped into a portion of the suture filament.

Then, the blades are rotated 180 degrees so that they are now disposed in the opposite direction and over the other half of the approximately 3 inch (approximately 76 mm) length of middle portion MP of the approximately 4.5 inch (approximately 114 mm) twisted section of the suture filament. The blades are then allowed to splice into the other half in a second cutting action with the blades making cuts to create barbs 78 so that all are facing in the opposite direction toward pointed end 76. Depending on how many blades there are on the cutting machine and how many barbs 78 are desired, there may be one cutting motion to cut all barbs 78 simultaneously, or there may be repeated cutting motions until the desired number of barbs 78 are escarped into a portion of the suture filament.

When twist cut multiple spiral barbed suture 70 is released from the vise and untwisted, the first cuts and the second cuts result in barbs 77, 78 being in two respective multiple spiral patterns on two respective portions of suture 70, the two respective portions defining middle portion MP of about 3 inches (about 76 mm) in length.

More particularly, several twist cut multiple spiral, barbed sutures were manufactured from a monofilament having a diameter of about 0.018 inch (about 0.457 mm) and spun from polydioxanone (which is a synthetic absorbable suture material). A diameter of about 0.018 inch (about 0.457 mm) is slightly larger than the size 0 synthetic absorbable suture, which has a diameter range from about 0.35 mm to about 0.399 mm in accordance with the specifications of the United States Pharmacopoeia (USP).

Each suture contained a total of 78 barbs introduced in two respective multiple spiral patterns around the circumference of the suture. Since the barbed suture was bi-directional, the barbs were divided into a left group with 39 barbs disposed on a first portion of the suture and a right group with 39 barbs on a second portion of the suture, each group opposing the direction of the other group from the approximate middle of the suture. The specific cutting machine employed had 13 blades. Thus, for each group of 39 barbs, there were 3 cutting motions (3×13=39), with the blades being offset with a guide for each of the 3 cutting motions.

Each suture was about 7 inches (about 178 mm) long. The middle portion MP was about 3 inches (about 76 mm) long and contained the 78 barbs that were escarped into the suture filament. Extending beyond the 3 inch (76 mm) barbed middle portion MP were two unbarbed end portions EP of the suture that were each about 2 inches (about 51 mm) long. Depending on the suturing technique, one or both ends of the barbed suture may be sufficiently pointed and rigid for insertion into tissue, or may comprise a straight or curved surgical needle.

The strength of the twist cut, 7 inch (178 mm) barbed sutures was tested by two methods. One method was a straight pull tensile strength test with a Universal Tester and the other method was an in vivo performance test with dogs.

For the straight pull tensile strength measurement, testing was performed using a Test Resources Universal Tester, Model 200Q. The average reading of 10 repeated measurements made for each kind of suture was recorded for the barbed sutures and for the comparison unbarbed sutures.

Comparison unbarbed sutures were polydioxanone monofilaments (a synthetic absorbable suture material) of various suture diameters of about 0.018 inch (about 0.457 mm), about 0.015 inch (about 0.381 mm), and about 0.0115 inch (about 0.292 mm), which are respectively slightly larger than the United States Pharmacopoeia sizes 0, 2-0, and 3-0 for synthetic absorbable sutures. In accordance with United States Pharmacopoeia specifications for synthetic absorbable sutures, size 0 has a diameter range of about 0.35 mm to about 0.399 mm; size 2-0 has a diameter range of about 0.30 mm to about 0.339 mm; and size 3-0 has a diameter range of about 0.20 mm to about 0.249 mm.

Each barbed suture was gripped at each end by being held with cork gasket padding in two respective serrated jaws, whereas each unbarbed suture was gripped at each end by being wrapped around two respective capstan roller grips. Capstan rollers were used for holding the unbarbed sutures to avoid stress and distension.

The portion of each suture specimen between the two gripped places was about 5 inches (about 126 mm) in length, which, in the case of barbed sutures, contained the entire 3 inches (76 mm) of the barbed middle portion.

Each specimen was pulled longitudinally at a rate of about 10 inches (about 254 mm) per minute until breakage occurred. The peak load was recorded as the straight pull tensile strength.

The results are summarized in Table 6A below, and the far right column denotes the USP knot pull test minimum requirements for conventional (unbarbed) sutures made from a synthetic absorbable material.

TABLE 6A (Tensile Strength)

| Barbed or Unbarbed | Suture Size | Straight Pull (pounds) | USP Minimum Requirements for Knot Pull (pounds) |
|---|---|---|---|
| Unbarbed | 0 | 17.72 | 8.60 |
| Unbarbed | 2-0 | 11.86 | 5.91 |
| Unbarbed | 3-0 | 8.82 | 3.90 |
| Barbed | 0 | 7.03 | not applicable |

As can be seen, escarpment of barbs into the size 0 polydioxanone monofilament reduced the straight pull tensile strength by approximately 60% as compared to the conventional unbarbed size 0 polydioxanone monofilament (7.03 pounds=40% of 17.72 pounds).

However, the straight pull tensile strength of 7.03 pounds at breakage for the size 0 polydioxanone barbed suture (which, due to the escarpment of the barbs, has an effective diameter that is smaller than the diameter of the conventional unbarbed size 0 polydioxanone suture) compared favorably with the minimum USP knot pull requirement of 8.60 pounds for the size 0 polydioxanone conventional unbarbed suture.

Additional straight pull tensile strength tests were performed on additional size 0 polydioxanone barbed sutures, as discussed below in Tables 7K-7Z, in connection with FIGS. 7A and 7B.

For the in vivo performance, 3 mongrel dogs, each about 14 kg, were used. On each dog, 7 incisions were made at the thorax (twice), thigh (twice), flank, ventral midline, and paramedian, each of the 7 incisions having 1, 2, or 3 closure sites. The length of each incision ranged from about 0.5 inch (about 12.5 mm) to about 4 inches (about 101 mm) and the depth of each incision was from the superficial dermis to the peritoneum.

Using the barbed sutures (all made from size 0 polydioxanone monofilament), 24 of the sites were closed. For comparison, the remaining sites were closed with various diameter sizes of conventional unbarbed sutures (1 site with size 2-0 silk braided filament, 6 sites with size 2-0 nylon monofilament, and 7 sites with size 3-0 polydioxanone monofilament), which were knotted. All closing of sites was performed according to a randomized scheme.

The dogs were monitored daily, and then subjected to euthanasia at 14 days. At the time of death, the incisions were evaluated macroscopically. With regard to various tissues, incision sizes, and locations on the dogs, all sites apposed with the size 0 polydioxanone barbed sutures stayed closed and appeared to be healing normally throughout the 14 day observation period. No dehiscence occurred.

The site apposed with the conventional unbarbed silk sutures and the sites apposed with the conventional unbarbed polydioxanone sutures also healed will without complications. No dehiscence occurred.

For the 6 topical skin sites closed with the size 2-0 nylon monofilament conventional unbarbed sutures, 3 sites exhibited partial or complete suture loss, apparently due to self-mutilation by the dogs. Knots in the conventional sutures possibly caused discomfort by creating localized pressure, and animals cannot understand that they should not manipulate the sutures. Thus, barbed sutures should help obviate the problem of an animal manipulating and pulling out the sutures.

In summary, the hi vivo performance of the size 0 polydioxanone barbed sutures was efficacious when compared to the size 2-0 silk braided filament unbarbed sutures, the size 2-0 nylon monofilament unbarbed sutures, and the size 3-0 polydioxanone monofilament unbarbed sutures.

In an alternative embodiment (not shown) for bi-directional twist cut, multiple spiral suture 70, the portion of suture 70 on which is disposed barbs 77 may have barbs 77 facing toward pointed end 76 and the portion of suture 70 on which is disposed barbs 78 may have barbs 78 facing toward pointed end 74. With this variation, the barbed suture would be inserted into tissue with an insertion device, such as that shown in the above-noted U.S. Pat. No. 5,342,376 to Ruff. Also if desired, it is noted that barbs may be escarped so that there may be 2 portions with barbs facing an end and 1 portion with barbs facing the other end, or 2 portions with barbs facing an end and 2 portions with barbs facing the other end, and so on (not shown), and thus, if a portion of barbs is not facing the suture end to which those barbs are adjacent, then, the barbed suture would be inserted into tissue with an insertion device.

An advantage of a barbed suture having a twist cut, multiple spiral disposition is that such a barbed suture affords better wound holding capability as compared to the 120 degree spaced barbed suture. The reason is that the twist cut, multiple spiral pattern results in groups of barbs that complement successive and preceding groups of barbs, which tends to provide improved anchoring when the suture is in tissue. This feature is especially useful for tissue such as fat tissue, which has fewer connective fibers compared with other types of tissues, so that greater suture retention force is desirable.

With reference now to FIG. 7A, shown is a sectional side view of barbed suture 80. Barbed suture 80 has plurality of closely spaced barbs 81 on elongated suture body 82 of generally circular cross section. Each barb 81 has barb tip 85. Shown are suture longitudinal axis A, suture diameter SD, barb length L, barb cut depth D, barb cut angle θ, cut distance P, spirality angle α, cut-out depression CD, and tip T of cut-out depression CD.

Figure 7B:
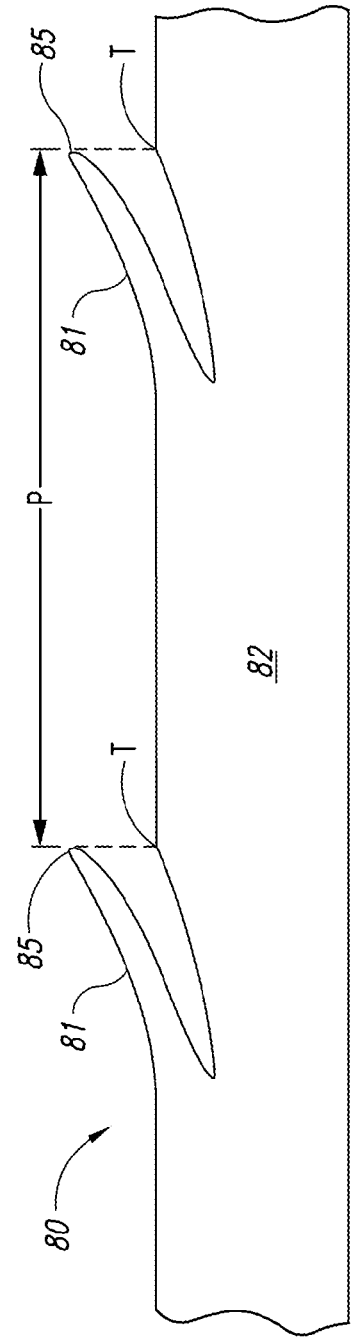
FIG. 7B is the sectional side view as illustrated in FIG. 7A, but rotated and clamped to align the barbs for measurement of the cut distance between the barbs.

FIG. 7B is the sectional side view as illustrated in FIG. 7A, but rotated and clamped to align the barbs for measurement of the cut distance P between barbs 81.

Barbed suture 80 is a twist cut, multiple spiral, bi-directional barbed suture, like suture 70 in FIG. 6A, but illustrated as an enlarged section in order to show more detail with respect to the configuration of barbs 81 vis-a-vis suture longitudinal axis A, suture diameter SD, barb length L, barb cut depth D, barb cut angle θ, cut distance P, spirality angle α, cut-out depression CD, and terminus T of cut-out depression CD.

More specifically, several twist cut, multiple spiral, barbed sutures were manufactured from monofilament spun from polydioxanone and having a diameter of about 0.018 inch (about 0.457 mm, which is slightly more than the USP requirement for a size 0 synthetic absorbable suture). Each suture contained 78 barbs introduced in 2 separate multiple spiral patterns around the circumference of the suture. Since the barbs were bi-directional, they were divided into a left group with 39 barbs and a right group with 39 barbs, each group opposing the direction of the other group from the approximate middle of the suture. Each suture was about 7 inches (about 178 mm) long. The middle portion was about 3 inches (about 76 mm) of the suture and contained the 78 barbs that were escarped into the suture filament. Extending beyond the 3 inch (76 mm) barbed middle portion toward each suture end were two unbarbed end portions of the suture filament that were each about 2 inches (about 51 mm) long. Depending on the stitching technique, one or both ends of the barbed suture may be sufficiently pointed and rigid for insertion into tissue, or may comprise a straight or curved needle.

In order to characterize the configuration of barbs 81, an Optem Zoom 100 custom microscope with both ring and back lighting was used together with a CCD brand video camera in order to measure selected barbs 81 at ×21.5 magnification from each of the left and right groups.

The average was calculated for 10 repeated measurements (5 from the left group of barbs and 5 from the right group of barbs on the same suture) that were made for each of cut angle θ and cut depth D. Barb cut angle θ was measured from the surface of the cut to the outer surface of barbed suture 80. Barb cut depth D was measured along a perpendicular from the outer surface of barbed suture 80 toward longitudinal axis A of barbed suture 80. The measurements enabled cut length L to be calculated using the following formula.

$$L = D / \{\mathrm{Sin}(180 - \theta)\}$$

Also, angle α of spirality was measured microscopically on various barbed sutures 80 as follows. When the twisted suture filament is gripped by the vise during cutting of barbs 81, the vise leaves a very light mark designated as line M impressed on the suture filament. Thus, line M will be parallel to the longitudinal axis of the vise while the twisted suture filament is being held in the vise. If the vise does not leave a light mark on the suture filament, then line M can be determined in that it is parallel to a line connecting the two respective terminus T of the two successive cut-out depressions CD left in suture body 82 from the escarpment of two successive barbs 81. After cutting of barbs 81, when barbed suture 80 is released from the vise and untwisted so that suture 80 lies free, then line M spirals on suture body 82 around barbed suture 80, forming angle α of spirality.

Specifically for measuring spirality angle α, the Optem Zoom 100 custom microscope was set with ring lighting at 60 and back lighting at coarse 12 and fine 10. Also, imaging analysis system software was used. Spirality angle α was then measured between the outer surface of the barbed suture and line M. The average was calculated for 10 repeated measurements (5 from the left group of barbs and 5 from the right group of barbs on the same suture).

Then, barbed suture 80 was mounted in a twisting device with one end of suture 80 clamped in a fixed position. The other end of suture 80 was rotated to insert twist until barbs 81 were aligned. Next on barbed suture 80, longitudinal cut distance P between two adjacent barbs 81 was measured microscopically between the two respective terminus T of the two successive cut-out depressions CD left in suture body 82 from the escarpment of two successive barbs 81. The average was calculated for 10 repeated measurements (5 from the left group of barbs and 5 from the right group of barbs on the same suture).

The results are summarized in the following Tables 7A, 7B, 7C, and 7D.

TABLE 7A (size 0 barbed suture)

| Measurement | Units | Left | Right | Ratio of D, L, or P over Suture Diameter (0.457 mm) |
|---|---|---|---|---|
| cut angle θ | degrees | 156 ± 2 | 157 ± 1 | not applicable |
| cut depth D | mm | 0.15 ± 0.02 | 0.16 ± 0.04 | 0.35 |
| cut length L | mm | 0.36 ± 0.03 | 0.40 ± 0.10 | 0.87 |
| cut distance P | mm | 0.90 ± 0.17 | 0.88 ± 0.15 | 1.92 |

TABLE 7B (size 0 barbed suture)

| Measurement | Units | Average | Standard Deviation | Ratio of D, L, or P over Suture Diameter (0.457 mm) |
|---|---|---|---|---|
| cut angle θ | degrees | 151 | 1.642 | not applicable |
| cut depth D | mm | 0.215 | 0.027 | 0.47 |
| cut length L | mm | 0.446 | 0.042 | 0.97 |
| cut distance P | mm | 0.962 | 0.073 | 2.1 |
| spirality angle α | degrees | 20.833 | 1.602 | not applicable |

TABLE 7C (size 0 barbed suture)

| Measurement | Units | Average | Standard Deviation | Ratio of D, L, or P over Suture Diameter (0.457 mm) |
|---|---|---|---|---|
| cut angle θ | degrees | 154 | 2.870 | not applicable |
| cut depth D | mm | 0.205 | 0.033 | 0.45 |
| cut length L | mm | 0.469 | 0.044 | 1.03 |
| cut distance P | mm | 0.975 | 0.103 | 2.13 |
| spirality angle α | degrees | 19.333 | 1.506 | not applicable |

TABLE 7D (size 0 barbed suture)

| Measurement | Units | Average | Standard Deviation | Ratio of D, L, or P over Suture Diameter (0.457 mm) |
|---|---|---|---|---|
| cut angle θ | degrees | 155 | 2.390 | not applicable |
| cut depth D | mm | 0.186 | 0.026 | 0.41 |
| cut length L | mm | 0.437 | 0.039 | 0.96 |
| cut distance P | mm | 0.966 | 0.071 | 2.11 |
| spirality angle α | degrees | 18.833 | 2.137 | not applicable |

Also, some additional measurements of angle α were performed on a few additional bi-directional twist cut, multiple spiral barbed sutures with a diameter of about 0.018 inch (about 0.457 mm, slightly more than the USP requirement for a size 0 synthetic absorbable suture). The mean average was 16.87 and the standard deviation was ±0.85.

Additionally, measurements of barb cut angle θ, barb length L, barb cut depth D, and cut distance P were performed on 3 additional bi-directional twist cut, multiple spiral barbed sutures like sutures 80, but having a diameter of about 0.0115 inch (about 0.292 mm, which is slightly more than the USP requirement for a size 3-0 synthetic absorbable suture), and measurements of spirality angle α were performed on 2 of these 3 additional barbed sutures. Also, measurements of barb cut angle θ, barb length L, barb cut depth D, cut distance P, and spirality angle α were performed on 3 additional bi-directional twist cut, multiple spiral barbed sutures like sutures 80, but with a diameter of about 0.015 inch (about 0.381 mm, which is slightly more than the USP requirement for a size 2-0 synthetic absorbable suture). The results are summarized in the following Tables 7E, 7F, 7G, 7H, 7I, and 7J.

TABLE 7E (size 3-0 barbed suture)

| Measurement | Units | Average | Standard Deviation | Ratio of D, L, or P over Suture Diameter (0.292 mm) |
|---|---|---|---|---|
| cut angle θ | degrees | 166 | 1.651 | not applicable |
| cut depth D | mm | 0.107 | 0.007 | 0.37 |
| cut length L | mm | 0.443 | 0.042 | 1.52 |
| cut distance P | mm | 0.956 | 0.079 | 3.27 |
| spirality angle α | degrees | not tested | not applicable | not applicable |

TABLE 7F (size 3-0 barbed suture)

| Measurement | Units | Average | Standard Deviation | Ratio of D, L, or P over Suture Diameter (0.292 mm) |
|---|---|---|---|---|
| cut angle θ | degrees | 164 | 2.055 | not applicable |
| cut depth D | mm | 0.106 | 0.006 | 0.36 |
| cut length L | mm | 0.395 | 0.042 | 1.35 |
| cut distance P | mm | 0.959 | 0.074 | 3.28 |
| spirality angle α | degrees | 7.329 | 0.547 | not applicable |

TABLE 7G (size 3-0 barbed suture)

| Measurement | Units | Average | Standard Deviation | Ratio of D, L, or P over Suture Diameter (0.292 mm) |
|---|---|---|---|---|
| cut angle θ | degrees | 165 | 1.031 | not applicable |
| cut depth D | mm | 0.104 | 0.009 | 0.36 |
| cut length L | mm | 0.390 | 0.035 | 1.34 |
| cut distance P | mm | 0.975 | 0.103 | 3.34 |
| spirality angle α | degrees | 7.258 | 0.636 | not applicable |

TABLE 7H (size 2-0 barbed suture)

| Measurement | Units | Average | Standard Deviation | Ratio of D, L, or P over Suture Diameter (0.381 mm) |
|---|---|---|---|---|
| cut angle θ | degrees | 160.2 | 1.320 | not applicable |
| cut depth D | mm | 0.152 | 0.019 | 0.40 |
| cut length L | mm | 0.449 | 0.057 | 1.18 |
| cut distance P | mm | 0.944 | 0.098 | 2.48 |
| spirality angle α | degrees | 9.40 | 1.606 | not applicable |

TABLE 7I (size 2-0 barbed suture)

| Measurement | Units | Average | Standard Deviation | Ratio of D, L, or P over Suture Diameter (0.381 mm) |
|---|---|---|---|---|
| cut angle θ | degrees | 161.0 | 1.707 | not applicable |
| cut depth D | mm | 0.158 | 0.014 | 0.41 |
| cut length L | mm | 0.489 | 0.054 | 1.28 |
| cut distance P | mm | 0.962 | 0.054 | 2.52 |
| spirality angle α | degrees | 7.96 | 1.075 | not applicable |

TABLE 7J (size 2-0 barbed suture)

| Measurement | Units | Average | Standard Deviation | Ratio of D, L, or P over Suture Diameter (0.381 mm) |
|---|---|---|---|---|
| cut angle θ | degrees | 161.0 | 1.506 | not applicable |
| cut depth D | mm | 0.154 | 0.017 | 0.40 |
| cut length L | mm | 0.474 | 0.058 | 1.24 |
| cut distance P | mm | 0.973 | 0.068 | 2.55 |
| spirality angle α | degrees | 6.53 | 1.755 | not applicable |

Additional measurements were performed on several other twist cut, multiple spiral, barbed sutures manufactured from monofilament spun from polydioxanone and having a diameter of about 0.018 inch (about 0.457 mm, which is slightly more than the USP requirement for a size 0 synthetic absorbable suture) and thus similar to the above-described tested barbed sutures, except that these other barbed sutures were cut with a different cutting machine, namely a machine with one blade that moved longitudinally along the twisted filament between cutting strokes and that was controlled with a computer to make the various cuts for the escarpment of the barbs. These other barbed sutures were also tested for straight pull tensile strength and for chamois cloth closure strength. (A discussion of how chamois cloth closure strength is performed can be seen below in connection with FIGS. 13A and 13B.) The results for these other barbed sutures are summarized in the following Tables 7K-7Z.

TABLE 7K (size 0 barbed suture)

| Measurement | Units | Average | Standard Deviation | Ratio of D, L, or P over Suture Diameter (0.457 mm) |
|---|---|---|---|---|
| cut angle θ | degrees | 152.6 | 0.718 | not applicable |
| cut depth D | mm | 0.221 | 0.011 | 0.48 |
| cut length L | mm | 0.479 | 0.022 | 1.05 |
| cut distance P | mm | 0.784 | 0.015 | 1.71 |
| spirality angle α | degrees | 12.9 | 0.453 | not applicable |

TABLE 7L (size 0 barbed suture)

| Measurement | Units | Average | Standard Deviation | Ratio of D, L, or P over Suture Diameter (0.457 mm) |
|---|---|---|---|---|
| cut angle θ | degrees | 152.4 | 0.947 | not applicable |
| cut depth D | mm | 0.216 | 0.014 | 0.47 |
| cut length L | mm | 0.465 | 0.024 | 1.02 |
| cut distance P | mm | 0.774 | 0.015 | 1.69 |
| spirality angle α | degrees | 13.2 | 0.349 | not applicable |

TABLE 7M (size 0 barbed suture)

| Measurement | Units | Average | Standard Deviation | Ratio of D, L, or P over Suture Diameter (0.457 mm) |
|---|---|---|---|---|
| cut angle θ | degrees | 152.3 | 0.576 | not applicable |
| cut depth D | mm | 0.227 | 0.015 | 0.50 |
| cut length L | mm | 0.489 | 0.034 | 1.07 |
| cut distance P | mm | 0.796 | 0.018 | 1.74 |
| spirality angle α | degrees | 13.1 | 0.193 | not applicable |

TABLE 7N (size 0 barbed suture)

| Measurement | Units | Average | Standard Deviation | Ratio of D, L, or P over Suture Diameter (0.457 mm) |
|---|---|---|---|---|
| cut angle θ | degrees | 152.8 | 0.612 | not applicable |
| cut depth D | mm | 0.207 | 0.007 | 0.45 |
| cut length L | mm | 0.453 | 0.016 | 0.99 |
| cut distance P | mm | 0.798 | 0.017 | 1.75 |
| spirality angle α | degrees | 13.6 | 0.560 | not applicable |

TABLE 7O (size 0 barbed suture)

| Measurement | Units | Average | Standard Deviation | Ratio of D, L, or P over Suture Diameter (0.457 mm) |
|---|---|---|---|---|
| cut angle θ | degrees | 152.9 | 0.549 | not applicable |
| cut depth D | mm | 0.188 | 0.016 | 0.41 |
| cut length L | mm | 0.413 | 0.030 | 0.90 |
| cut distance P | mm | 0.787 | 0.024 | 1.72 |
| spirality angle α | degrees | 13.8 | 0.270 | not applicable |

TABLE 7P (size 0 barbed suture)

| Measurement | Units | Average | Standard Deviation | Ratio of D, L, or P over Suture Diameter (0.457 mm) |
|---|---|---|---|---|
| cut angle θ | degrees | 153.1 | 0.655 | not applicable |
| cut depth D | mm | 0.204 | 0.007 | 0.45 |
| cut length L | mm | 0.451 | 0.019 | 0.99 |
| cut distance P | mm | 0.792 | 0.018 | 1.73 |
| spirality angle α | degrees | 13.6 | 0.410 | not applicable |

TABLE 7Q (size 0 barbed suture)

| Measurement | Units | Average | Standard Deviation | Ratio of D, L, or P over Suture Diameter (0.457 mm) |
|---|---|---|---|---|
| cut angle θ | degrees | 163.1 | 0.505 | not applicable |
| cut depth D | mm | 0.245 | 0.013 | 0.54 |
| cut length L | mm | 0.842 | 0.045 | 1.84 |
| cut distance P | mm | 0.774 | 0.009 | 1.69 |
| spirality angle α | degrees | 10.8 | 0.449 | not applicable |

TABLE 7R (size 0 barbed suture)

| Measurement | Units | Average | Standard Deviation | Ratio of D, L, or P over Suture Diameter (0.457 mm) |
|---|---|---|---|---|
| cut angle θ | degrees | 161.1 | 1.126 | not applicable |
| cut depth D | mm | 0.233 | 0.017 | 0.51 |
| cut length L | mm | 0.721 | 0.035 | 1.58 |
| cut distance P | mm | 0.773 | 0.010 | 1.69 |
| spirality angle α | degrees | 12.6 | 0.189 | not applicable |

TABLE 7S (size 0 barbed suture)

| Measurement | Units | Average | Standard Deviation | Ratio of D, L, or P over Suture Diameter (0.457 mm) |
|---|---|---|---|---|
| cut angle θ | degrees | 160.9 | 0.708 | not applicable |
| cut depth D | mm | 0.240 | 0.014 | 0.52 |
| cut length L | mm | 0.734 | 0.037 | 1.61 |
| cut distance P | mm | 0.774 | 0.009 | 1.69 |
| spirality angle α | degrees | 13.6 | 0.312 | not applicable |

TABLE 7T (size 0 barbed suture)

| Measurement | Units | Average | Standard Deviation | Ratio of D, L, or P over Suture Diameter (0.457 mm) |
|---|---|---|---|---|
| cut angle θ | degrees | 154.6 | 1.434 | not applicable |
| cut depth D | mm | 0.210 | 0.009 | 0.46 |
| cut length L | mm | 0.492 | 0.026 | 1.08 |
| cut distance P | mm | 0.538 | 0.011 | 1.18 |
| spirality angle α | degrees | 12.3 | 0.223 | not applicable |

TABLE 7U (size 0 barbed suture)

| Measurement | Units | Average | Standard Deviation | Ratio of D, L, or P over Suture Diameter (0.457 mm) |
|---|---|---|---|---|
| cut angle θ | degrees | 152.9 | 0.809 | not applicable |
| cut depth D | mm | 0.212 | 0.014 | 0.46 |
| cut length L | mm | 0.464 | 0.026 | 1.01 |
| cut distance P | mm | 0.530 | 0.015 | 1.16 |
| spirality angle α | degrees | 13.7 | 0.411 | not applicable |

TABLE 7V (size 0 barbed suture)

| Measurement | Units | Average | Standard Deviation | Ratio of D, L, or P over Suture Diameter (0.457 mm) |
|---|---|---|---|---|
| cut angle θ | degrees | 153.4 | 0.903 | not applicable |
| cut depth D | mm | 0.221 | 0.010 | 0.48 |
| cut length L | mm | 0.495 | 0.023 | 1.08 |
| cut distance P | mm | 0.537 | 0.012 | 1.17 |
| spirality angle α | degrees | 13.9 | 0.605 | not applicable |

TABLE 7W (size 0 barbed suture)

| Measurement | Units | Average | Standard Deviation | Ratio of D, L, or P over Suture Diameter (0.457 mm) |
|---|---|---|---|---|
| cut angle θ | degrees | 155.2 | 0.829 | not applicable |
| cut depth D | mm | 0.202 | 0.008 | 0.44 |
| cut length L | mm | 0.483 | 0.017 | 1.06 |
| cut distance P | mm | 0.789 | 0.031 | 1.73 |
| spirality angle α | degrees | 12.6 | 0.328 | not applicable |

TABLE 7X (size 0 barbed suture)

| Measurement | Units | Average | Standard Deviation | Ratio of D, L, or P over Suture Diameter (0.457 mm) |
|---|---|---|---|---|
| cut angle θ | degrees | 155.5 | 0.799 | not applicable |
| cut depth D | mm | 0.200 | 0.010 | 0.44 |
| cut length L | mm | 0.484 | 0.027 | 1.06 |
| cut distance P | mm | 0.798 | 0.017 | 1.75 |
| spirality angle α | degrees | 11.8 | 0.362 | not applicable |

TABLE 7Y (size 0 barbed suture)

| Measurement | Units | Average | Standard Deviation | Ratio of D, L, or P over Suture Diameter (0.457 mm) |
|---|---|---|---|---|
| cut angle θ | degrees | 155.4 | 0.560 | not applicable |
| cut depth D | mm | 0.196 | 0.008 | 0.43 |
| cut length L | mm | 0.471 | 0.017 | 1.03 |
| cut distance P | mm | 0.799 | 0.019 | 1.75 |
| spirality angle α | degrees | 11.8 | 0.496 | not applicable |

TABLE 7Z

| Barbed Suture | Straight Pull Strength (pounds) | Chamois Cloth Closure Strength (pounds to rupture) |
|---|---|---|
| Sample 1 (Tables 7K-7M) | 7.29 | 11.23 |
| Sample 2 (Tables 7N-7P) | 8.73 | 12.14 |
| Sample 3 (Tables 7Q-7S) | 8.5 | 9.22 |
| Sample 4 (Tables 7T-7V) | 5.92 | 9.27 |
| Sample 5 (Tables 7W-Y) | 7.69 | 9.97 |

Although all the above-noted measurements were performed on bi-directional, twist cut, multiple spiral barbed sutures, the below-noted desirable ranges for measurements for barb length L, barb cut depth D, barb cut angle θ, and/or cut distance P should be the same for the various other inventive barbed sutures described here.

A suitable ratio of cut length L to barbed suture diameter SD ranges from about 0.2 to about 2, more preferably from about 0.4 to about 1.7, even more preferably from about 0.8 to about 1.5. However, very suitable barbed sutures may have a ratio of cut length L to barbed suture diameter SD from about 1 down to about 0.2, whereby the ratio of the highest possible barb elevation (the elevation of barb tip 85 above suture body 82) to the suture diameter SD correspondingly ranges from about 1 down to about 0.2. (The highest possible barb elevation is the same as the barb length L.) Also, a suitable ratio of cut depth D to barbed suture diameter SD ranges from about 0.05 to about 0.6, more preferably from about 0.1 to about 0.55, even more preferably from about 0.2 to about 0.5.

Regardless, length L may be desirably varied depending on the intended end use, since larger barbs are more suitable for joining certain types of tissue such as fat tissue or soft tissue, whereas smaller barbs are more suitable for joining other types of tissues such as fibrous tissue. As discussed in more detail below vis-a-vis FIG. 11, there will also be instances where a barb configuration that is a combination of large, medium, and/or small barbs disposed on the same suture will be desirable, for instance, when the barbed suture is employed in tissue that has differing layer structures.

Cut angle θ formed between the barb and the elongated suture body desirably would range from about 140 degrees to about 175 degrees, more preferably would range from about 145 degrees to about 173 degrees. The most preferred cut angle θ for all barbs ranges from about 150° to about 170°.

For instance, for a polydioxanone barbed suture with a diameter of about 0.018 inch (about 0.457 mm), which is slightly larger that the USP requirement for a synthetic absorbable suture of size 0, the preferred barb length L would be 0.45 mm; the preferred barb depth D would be 0.2 mm; and the preferred barb cut angle would be 153 degrees.

Longitudinal spacing between any two barbs is generally effected with the goal of creating as many barbs as possible along the suture, and is a factor in the ability of the barbed suture to anchor tissues while maintaining firmness. As barbs are spaced farther apart, tissue-anchoring capacity decreases. Nevertheless, if barbs are spaced too close, the integrity of the filament may be jeopardized, which could lead to a tendency of the barbs to peel back and also to a decrease in suture tensile strength.

Generally, a suitable ratio of cut distance P to barbed suture diameter SD ranges from about 0.1 to about 6, more preferably from about 0.5 to about 4.5, even more preferably from about 1.0 to about 3.5. Very suitable barbed sutures may have a ratio of cut distance P to barbed suture diameter SD from about 1.5 down to about 0.2, whereby cut distance P may be as low as about 0.1, particularly for the overlapping barb embodiment, which is discussed in more detail below vis-à-vis FIGS. 12A, 12B, 12C, and 12D.

Additionally, spirality angle α formed between line M and the longitudinal direction of the elongated suture body for a twist cut, multiple spiral barbed suture typically would range from about 5 degrees to about 25 degrees, more preferably from about 7 degrees to about 21 degrees. The most preferred angle α for all barbs on a twist cut, multiple spiral barbed suture is about 10° to about 18°.

Figure 8:
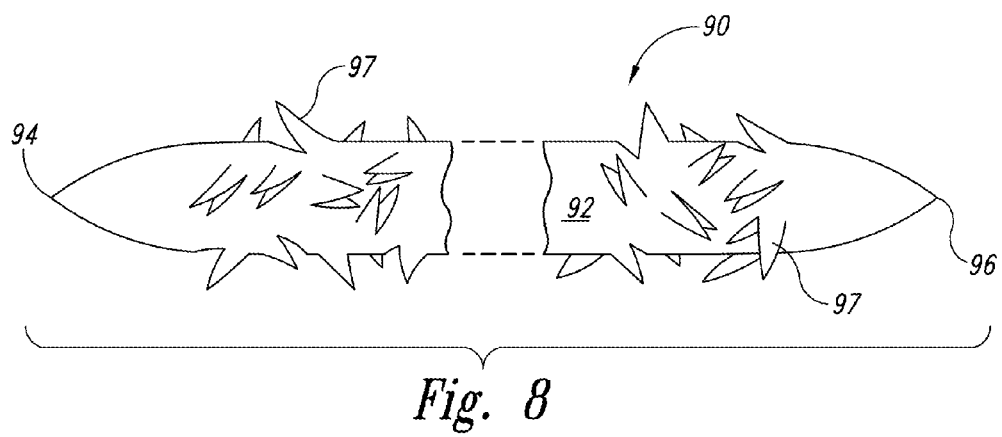
FIG. 8 is a side view of another embodiment of the present invention, showing a barbed suture with barbs in a random disposition.

Turning now to FIG. 8, shown is suture 90, which is another embodiment of the present invention. Suture 90 includes elongated body 92 that is generally circular in cross section. Elongated body 92 terminates in first and second pointed ends 94, 96 for penetrating tissue. It is contemplated that one or both ends 94, 96 may comprise a surgical needle (not shown) for insertion into tissue. Additionally, suture 90 includes plurality of closely spaced barbs 97 arranged in a random disposition.

Suture 90 may be made with the same cutting machine as the above-discussed sutures, such as the cutting device described in the above-noted Ser. No. 09/943,733 to Genova et al. With combinations of the above-described methods for making the 180 degree disposition (sutures 1, 10), the 120 degree disposition (sutures 30, 40), and/or the twist cut multiple spiral disposition (sutures 60, 70, 80), barbed suture 90 with a very random barb disposition is obtained. The advantage of the random disposition is that the many barb angles provide superior anchoring in tissues and thus afford superior wound holding properties. With the random disposition, the barbed suture would be inserted into tissue with an insertion device, such as that shown in the above-noted U.S. Pat. No. 5,342,376 to Ruff.

Figure 9:
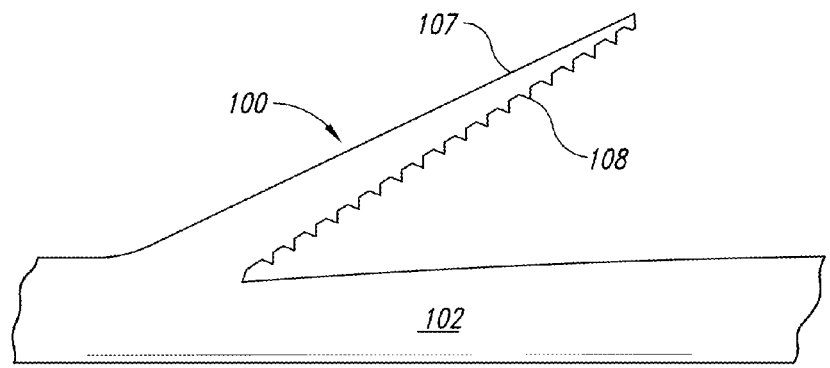
FIG. 9 is a sectional side view of another embodiment of the present invention, showing a barbed suture having a barb with a corrugated or serrated underside.

With regard to FIG. 9, shown is a sectional side view of barbed suture 100, which is another embodiment of the present invention. Suture 100 includes elongated suture body 102 of generally circular cross section. Also, suture body 102 has disposed on it a plurality of closely spaced barbs 107. Each barb 107 has a barb configuration such that barb underside 108 is serrated or corrugated. One or both suture ends (not shown) are pointed for penetrating tissue and it is contemplated that one or both may comprise a surgical needle (not shown) for insertion into tissue.

Suture 100 may be made with the same cutting machine as the above-discussed sutures, such as the cutting device described in the above-noted Ser. No. 09/943,733 to Genova et al. Barb 107 having serrated underside 108 is achieved by vibrating or oscillating the cutting blades of the cutting device when barbs are being escarped into the body of a monofilament. It is intended that any of the barbed sutures of the present invention as described here may have barbs with a configuration that includes a serrated or corrugated underside.

Figure 10A:
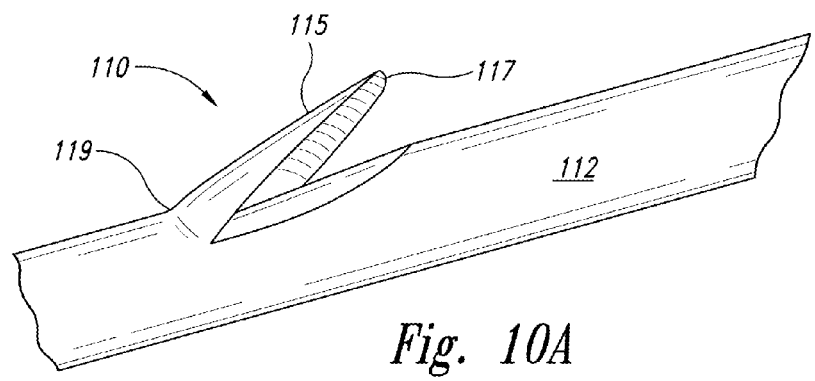
FIG. 10A is a sectional perspective view another embodiment of the present invention, showing a barbed suture having a barb with an arcuate base.
Figure 10B:
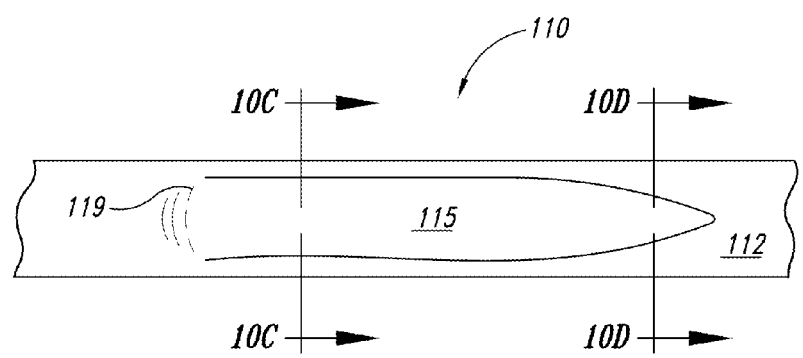
FIG. 10B is a sectional top plan view of the barbed suture in FIG. 10A.

With reference now to FIGS. 10A and 10B, depicted in FIG. 10A is a perspective view and depicted in FIG. 10B is a top view of barbed suture 110, which is another embodiment of the present invention. Suture 110 includes elongated suture body 112 of generally circular cross section. Also, suture body 112 has disposed on it a plurality of closely spaced barbs 115 having barb tips 117 (one barb 115 is shown for purposes of brevity). Barb 115 has a configuration with an arcuate base 119 where barb 115 is attached to suture body 112. One or both suture ends (not shown) are pointed for penetrating tissue and it is contemplated that one or both may comprise a surgical needle (not shown) for insertion into tissue.

Figure 10C:
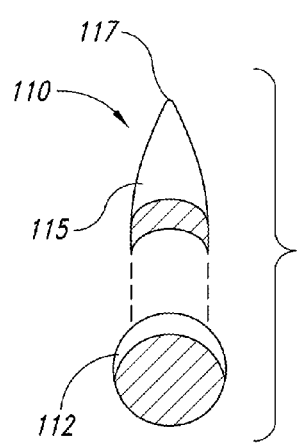
FIG. 10C is a cross-sectional view along line 10C-10C of FIG. 10B.
Figure 10D:
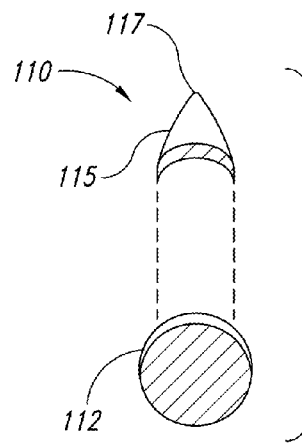
FIG. 10D is a cross-sectional view along line 10D-10D of FIG. 10B.

FIGS. 10C and 10D are cross-sectional views respectively along line 10C-10C and line 10D-10D of FIG. 10B. FIGS. 10C and 10D further clarify that barb 115 becomes narrower going from base 119 toward tip 117.

Suture 110 may be made with the same cutting machine as the above-discussed sutures, such as the cutting device described in the above-noted Ser. No. 09/943,733 to Genova et al. To achieve barb 115 having arcuate base 119, the cutting device is provided with cutting blades with ends that are correspondingly arcuate with respect to arcuate base 119.

It is intended that any of the barbed sutures of the present invention as described here may have barbs with a configuration that includes an arcuate base. The arcuate base should enhance tissue anchoring as compared to a flat, linear base. Regardless, it is not desired for the base to be circular or oval, which would result from conical shaped barbs, as that could decrease tissue anchoring.

Figure 11:
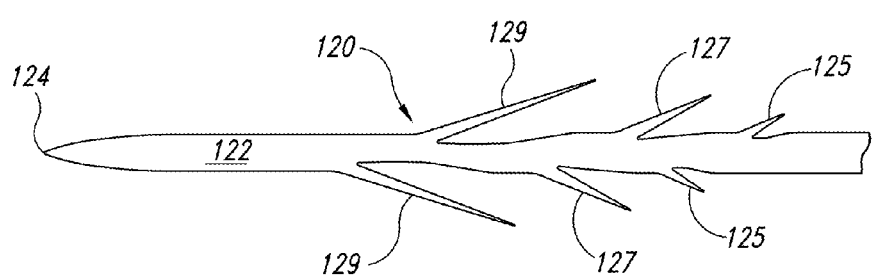
FIG. 11 is a sectional side view of another embodiment of the present invention, showing a barbed suture with barbs of various sizes.

Shown in FIG. 11 is a sectional side view of a barbed suture that is another embodiment of the present invention, and that is generally designated at 120. Suture 120 includes elongated body 122 that is generally circular in cross section. Elongated body 122 terminates in end 124. End 124 is pointed for penetrating tissue and it is contemplated that end 124 may comprise a surgical needle (not shown) for insertion into tissue. (The other end is not shown, and also may be pointed for penetrating tissue and may comprise a surgical needle for penetrating tissue.) Also, suture 120 includes plurality of closely spaced barbs 125, plurality of closely spaced barbs 127, and plurality of closely spaced barbs 129. Barbs 125 are relatively small in size with a relatively short barb length as compared to barbs 127, which are relatively medium in size with a relatively medium barb length, as compared to barbs 129, which are relatively large in size with a relatively long barb length.

Suture 120 may be made with the same cutting machine as the above-described sutures were made, such as the cutting device described in the above-noted Ser. No. 09/943,733 to Genova et al. By altering the amount of blade movement during cutting into a suture filament, then the barb cut length is made longer or shorter, as desired, to result in each of the three sets of barbs 125, 127, and 129 being of a size different from the others, where the varying sizes are designed for various surgical applications. The barb size may also vary in the transverse direction, whereby the barb base may be short, medium, or long, and regardless, the barb base typically is less than about ¼ of the suture diameter.

For instance, relatively larger barbs are desirable for joining fat and soft tissues, whereas relatively smaller barbs are desirable for joining fibrous tissues. Use of a combination of large, medium, and/or small barbs on the same suture helps to ensure maximum anchoring properties when barb sizes are customized for each tissue layer. Only two different sized sets of barbs (not shown) may be escarped into suture body 122, or additional sets of barbs (not shown) with four, five, six, or more different sized sets than three sizes as illustrated for sets of barbs 125, 127, and 129 may be escarped into suture body 122 as desired, in accordance with the intended end use. Also, although suture 120 is illustrated with the barbs being unidirectional, it is intended that barbed sutures with barbs having a configuration of varying sizes in accordance with the invention also may be bi-directional barbed sutures or random barbed sutures or any of the other inventive barbed sutures described here.

Figure 12A:
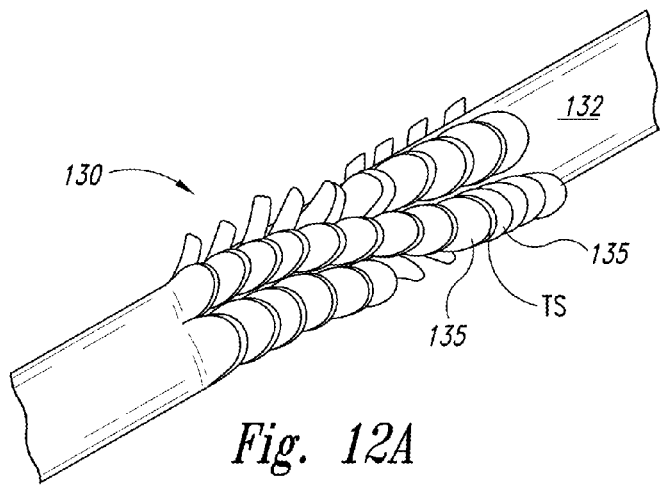
FIG. 12A is a sectional perspective view of another embodiment of the present invention, showing a barbed suture with barbs in an overlapping disposition.

FIG. 12A is a perspective view of another embodiment of the present invention, showing barbed suture 130 having elongated body 132 of generally circular cross section. One or both suture ends (not shown) are pointed for penetrating tissue and it is contemplated that one or both ends may comprise a surgical needle (not shown) for insertion into tissue.

Suture 130 further includes plurality of barbs 135 projecting from body 132 such that at least two longitudinally adjacent first and second barbs 135 are disposed on body 132 where first barb 135 overlaps second barb 135 if first and second barbs 135, which is readily apparent if barbs 135 are laid flat on body 132.

Figure 12B:
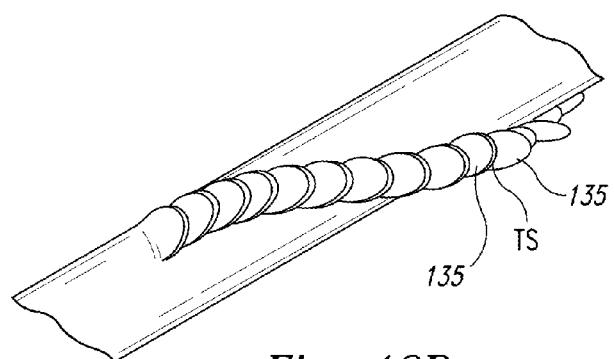
FIG. 12B is a perspective view of a portion of the overlapping barbs of the suture of FIG. 12A.
Figure 12C:
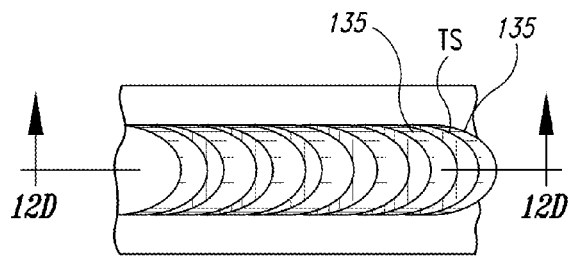
FIG. 12C is a plan view of the portion of barbs of FIG. 12B.
Figure 12D:
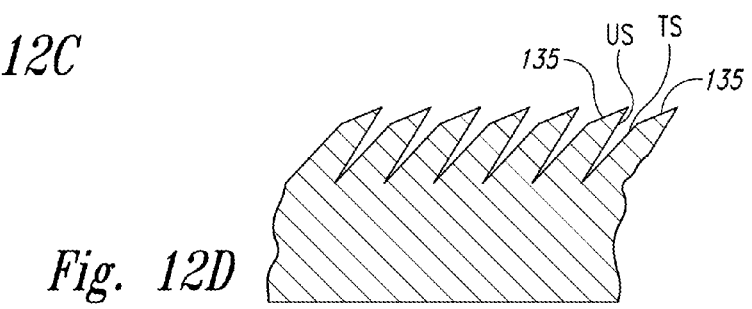
FIG. 12D is a side view along line 12D-12D of FIG. 12C.

FIG. 12B is a perspective view of a portion of overlapping barbs 135 of the overlapping disposition barbed suture 130 of FIG. 12A, and FIG. 12C is a top plan view of FIG. 12B. FIG. 12D is a cross-sectional view along line 12D-12D of FIG. 12C. As can be more clearly seen from FIGS. 12B, 12C, and 12D, during escarpment of barbs 135, overlapping first barb 135 is escarped into part of topside TS of overlapped second barb 135, and so on. Part of topside TS of overlapped second barb 135 becomes part of underside US of overlapping first barb 135.

Thus, with the overlapping disposition, the barb cut distance between first barb 135 and second barb 135 may be shorter than the barb cut length of overlapped second barb 135, whereas, in general for barbed sutures, the barb cut distance between two barbs≥the barb cut length. Particularly for the overlapping barb disposition, very suitable barbed sutures may have a ratio of the barb cut distance to the barbed suture diameter from about 1.5 down to about 0.2, since the barb cut distance P may be as low as about 0.1. (See discussion of FIG. 7 for comments vis-à-vis the barb cut length and the barb cut distance.) This overlapping disposition allows for closely packing many barbs 135 on body 132, and typically, barbs 135 are thin, as compared to when the barb cut distance between two barbs≥the barb cut length.

Also, although suture 130 is illustrated with barbs 135 being unidirectional, it is intended to include that suture 130 in accordance with the invention also may be a bi-directional barbed suture as described here.

FIGS. 13A, 13B, 13C, 13D, 14A, 14B, 14C, 14D, 15A, 15B, 15C, 15D, 16A, 16B, 16C, and 16D show various surgical needles, where a barbed suture is attached to each surgical needle. In order to facilitate insertion into tissue, the surgical needles may be coated with a polymer, for instance, as described above vis-à-vis U.S. Pat. No. 5,258,013 to Granger et al.

FIG. 13A shows surgical needle N1 that is a straight elongated needle in the longitudinal direction and that is generally circular in cross section. Surgical needle N1 has pointed tip T1 for insertion into tissue and also has hole H1. Surgical needle N1 is illustrated as attached, such as by swaging, to barbed suture S1. Barbed suture S1 is a barbed suture including, but not limited to, any of the above-described barbed sutures. Additionally, surgical needle N1 has diameter D1 in the transverse direction, which is illustrated as a relatively thin diameter, such as about 0.02 inch (about 0.51 mm). As discussed above vis-a-vis swaging, surgical needle N1, after having suture S1 inserted into hole H1, may be crimped by standard procedures about hole H1 to hold suture S1 in place for suturing tissue.

FIG. 13B shows surgical needle N2 that is a straight elongated needle in the longitudinal direction and that is generally circular in cross section. Surgical needle N2 has pointed tip T2 for insertion into tissue and also has hole H2. Surgical needle N2 is illustrated as attached, such as by swaging, to barbed suture S2. Barbed suture S2 is a barbed suture including, but not limited to, any of the above-described barbed sutures. Additionally, surgical needle N2 has diameter D2 in the transverse direction, which is illustrated as a suitably thin diameter, such as about 0.032 inch (about 0.81 mm), but not as thin as diameter D1 of surgical needle N1. As discussed above vis-à-vis swaging, surgical needle N2, after having suture S2 inserted into hole H2, may be crimped by standard procedures about hole H2 to hold suture S2 in place for use in suturing tissue.

FIG. 13C shows surgical needle N3 that is a curved elongated needle in the longitudinal direction and that is generally circular in cross section. Surgical needle N3 has pointed tip T3 for insertion into tissue and also has hole H3. Surgical needle N3 is illustrated as attached, such as by swaging, to barbed suture S3. Barbed suture S3 is a barbed suture including, but not limited to, any of the above-described barbed sutures. Additionally, surgical needle N3 has diameter D3 in the transverse direction, which is illustrated as a relatively thin diameter, such as about 0.02 inch (about 0.51 mm). As discussed above vis-à-vis swaging, surgical needle N3, after having suture S3 inserted into hole H3, may be crimped by standard procedures about hole H3 to hold suture S3 in place for use in suturing tissue.

FIG. 13D shows surgical needle N4 that is a curved elongated needle in the longitudinal direction and that is generally circular in cross section. Surgical needle N4 has pointed tip T4 for insertion into tissue and also has hole H4. Surgical needle N4 is illustrated as attached, such as by swaging, to barbed suture S4. Barbed suture S4 is a barbed suture including, but not limited to, any of the above-described barbed sutures. Additionally, surgical needle N4 has diameter D4 in the transverse direction, which is illustrated as a suitably thin diameter, such as about 0.032 inch (about 0.81 mm), but not as thin as diameter D3 of surgical needle N3. As discussed above vis-à-vis swaging, surgical needle N4, after having suture S4 inserted into hole H4, may be crimped by standard procedures about hole H4 to hold suture S4 in place for use in suturing tissue.

Figure 14A:
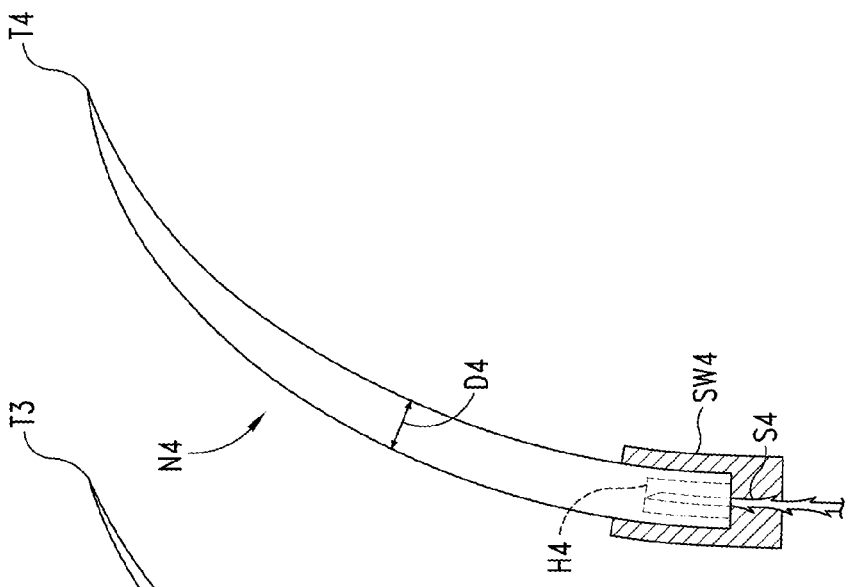
FIGS. 14A, 14B, 14C, and 14D show various surgical needles, where a barbed suture is attached to each surgical needle by shrink wrapping.

FIG. 14A shows surgical needle N1 that is a straight elongated needle in the longitudinal direction and that is generally circular in cross section. Surgical needle N1 has pointed tip T1 for insertion into tissue and also has hole H1. Barbed suture S1 is a barbed suture including, but not limited to, any of the above-described barbed sutures. Additionally, surgical needle N1 has diameter D1 in the transverse direction, which is illustrated as a relatively thin diameter, such as about 0.02 inch (about 0.51 mm). Surgical needle N1 is illustrated as attached by shrink wrapping SW1 to barbed suture 51. More particularly, surgical needle N1, after having suture S1 inserted into hole H1, is shown having shrink wrapping SW1, illustrated in cutaway and disposed about needle/suture N1/S1, where the end of suture S1 is disposed in hole H1 at the end of needle N1, in order to hold suture S1 in place for suturing tissue. Surgical needle S1 may be crimped by standard procedures about hole H1 to help hold suture S1 in place.

Figure 14B:
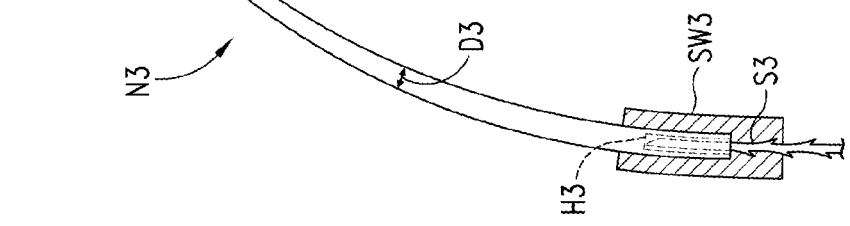

FIG. 14B shows surgical needle N2 that is a straight elongated needle in the longitudinal direction and that is generally circular in cross section. Surgical needle N2 has pointed tip T2 for insertion into tissue and also has hole H2. Barbed suture S2 is a barbed suture including, but not limited to, any of the above-described barbed sutures. Additionally, surgical needle N2 has diameter D2 in the transverse direction, which is illustrated as a suitably thin diameter, such as about 0.032 inch (about 0.81 mm), but not as thin as diameter D1 of surgical needle N1. Surgical needle N2 is illustrated as attached by shrink wrapping SW2 to barbed suture S2. More particularly, surgical needle N2, after having suture S2 inserted into hole H2, is shown having shrink wrapping SW2, illustrated in cutaway and disposed about needle/suture N2/S2, where the end of suture S2 is disposed in hole H2 at the end of needle N2, in order to hold suture S2 in place for suturing tissue. Surgical needle S2 may be crimped by standard procedures about hole H2 to help hold suture S2 in place.

Figure 14C:
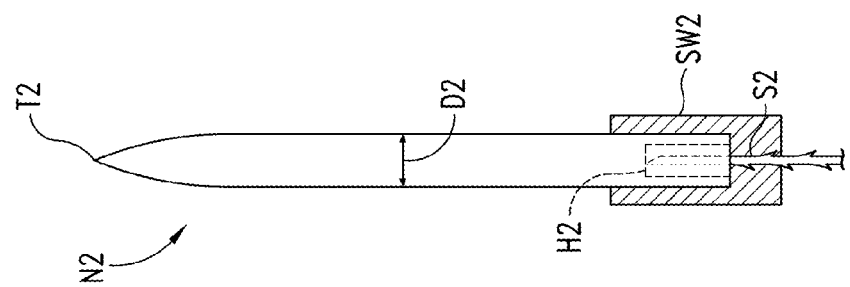

FIG. 14C shows surgical needle N3 that is a curved elongated needle in the longitudinal direction and that is generally circular in cross section. Surgical needle N3 has pointed tip T3 for insertion into tissue and also has hole H3. Barbed suture S3 is a barbed suture including, but not limited to, any of the above-described barbed sutures. Additionally, surgical needle N3 has diameter D3 in the transverse direction, which is illustrated as a relatively thin diameter, such as about 0.02 inch (about 0.51 mm). Surgical needle N3 is illustrated as attached by shrink wrapping SW3 to barbed suture S3. More particularly, surgical needle N3, after having suture S3 inserted into hole H3, is shown having shrink wrapping SW3, illustrated in cutaway and disposed about needle/suture N3/S3, where the end of suture S3 is disposed in hole H3, at the end of needle N3, in order to hold suture S3 in place for suturing tissue. Surgical needle S3 may be crimped by standard procedures about hole H3 to help hold suture S3 in place.

Figure 14D:
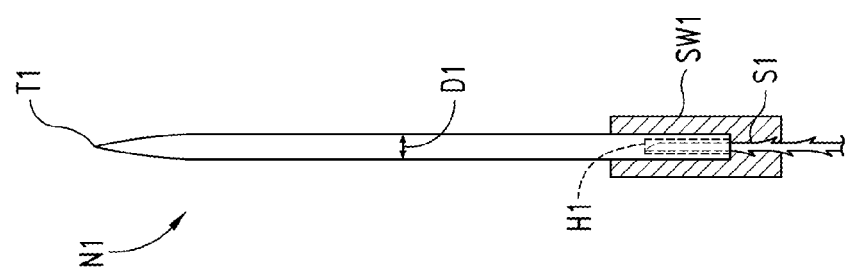

FIG. 14D shows surgical needle N4 that is a curved elongated needle in the longitudinal direction and that is generally circular in cross section. Surgical needle N4 has pointed tip T4 for insertion into tissue and also has hole H4. Barbed suture S4 is a barbed suture including, but not limited to, any of the above-described barbed sutures. Additionally, surgical needle N4 has diameter D4 in the transverse direction, which is illustrated as a suitably thin diameter, such as about 0.032 inch (about 0.81 mm), but not as thin as diameter D3 of surgical needle N3. Surgical needle N4 is illustrated as attached by shrink wrapping SW4 to barbed suture S4. More particularly, surgical needle N4, after having suture S4 inserted into hole H4, is shown having shrink wrapping SW4, illustrated in cutaway and disposed about needle/suture N4/S4, where the end of suture S4 is disposed in hole H4, at the end of needle N4, in order to hold suture S4 in place for suturing tissue. Surgical needle S4 may be crimped by standard procedures about hole H4 to help hold suture S4 in place.

FIG. 15A shows surgical needle N1 that is a straight elongated needle in the longitudinal direction and that is generally circular in cross section. Surgical needle N1 has pointed tip T1 for insertion into tissue and also has channel C1. Barbed suture S1 is a barbed suture including, but not limited to, any of the above-described barbed sutures. Additionally, surgical needle N1 has diameter D1 in the transverse direction, which is illustrated as a relatively thin diameter, such as about 0.02 inch (about 0.51 mm). Surgical needle N1 is illustrated as attached by channel wrapping CW1 to barbed suture S1. More particularly, surgical needle N1, after having suture S1 placed into channel C1, is shown having channel wrapping CW1, illustrated in cutaway and disposed about needle/suture N1/S1, where the end of suture S1 is disposed in channel C1 at the end of the needle N1, in order to hold suture S1 in place for suturing tissue. Surgical needle S1 may be crimped by standard procedures about channel C1 to help hold suture S1 in place.

FIG. 15B shows surgical needle N2 that is a straight elongated needle in the longitudinal direction and that is generally circular in cross section. Surgical needle N2 has pointed tip T2 for insertion into tissue and also has channel C2. Barbed suture S2 is a barbed suture including, but not limited to, any of the above-described barbed sutures. Additionally, surgical needle N2 has diameter D2 in the transverse direction, which is illustrated as a suitably thin diameter, such as about 0.032 inch (about 0.81 mm), but not as thin as diameter D1 of surgical needle N1. Surgical needle N2 is illustrated as attached by channel wrapping CW2 to barbed suture S2. More particularly, surgical needle N1, after having suture S2 placed into channel C2, is shown having channel wrapping CW2, illustrated in cutaway and disposed about needle/suture N2/52, where the end of suture S2 is disposed in channel C2 at the end of the needle N2, in order to hold suture S2 in place for suturing tissue. Surgical needle S2 may be crimped by standard procedures about channel C2 to help hold suture S2 in place.

FIG. 15C shows surgical needle N3 that is a curved elongated needle in the longitudinal direction and that is generally circular in cross section. Surgical needle N3 has pointed tip T3 for insertion into tissue and also has channel C3. Barbed suture S3 is a barbed suture including, but not limited to, any of the above-described barbed sutures. Additionally, surgical needle N3 has diameter D3 in the transverse direction, which is illustrated as a relatively thin diameter, such as about 0.02 inch (about 0.51 mm). Surgical needle N3 is illustrated as attached by channel wrapping CW3 to barbed suture S3. More particularly, surgical needle N3, after having suture S3 placed into channel C3, is shown having channel wrapping CW3, illustrated in cutaway and disposed about needle/suture N3/S3, where the end of suture S3 is disposed in channel C3, at the end of needle N3, in order to hold suture S3 in place for suturing tissue. Surgical needle S3 may be crimped by standard procedures about channel C3 to help hold suture S3 in place.

FIG. 15D shows surgical needle N4 that is a curved elongated needle in the longitudinal direction and that is generally circular in cross section. Surgical needle N4 has pointed tip T4 for insertion into tissue and also has channel C4. Barbed suture S4 is a barbed suture including, but not limited to, any of the above-described barbed sutures. Additionally, surgical needle N4 has diameter D4 in the transverse direction, which is illustrated as a suitably thin diameter, such as about 0.032 inch (about 0.81 mm), but not as thin as diameter D3 of surgical needle N3. Surgical needle N4 is illustrated as attached by channel wrapping CW4 to barbed suture S4. More particularly, surgical needle N4, after having suture S4 placed into channel C4, is shown having channel wrapping CW4, illustrated in cutaway and disposed about needle/suture N4/S4, where the end of suture S4 is disposed in channel C4, at the end of needle N4, in order to hold suture S4 in place for suturing tissue. Surgical needle S4 may be crimped by standard procedures about channel C4 to help hold suture S4 in place.

FIG. 16A shows surgical needle N1 that is a straight elongated needle in the longitudinal direction and that is generally circular in cross section. Surgical needle N1 has pointed tip T1 for insertion into tissue and also has eyelet E1. Barbed suture S1 is a barbed suture including, but not limited to, any of the above-described barbed sutures. Additionally, surgical needle N1 has diameter D1 in the transverse direction, which is illustrated as a relatively thin diameter, such as about 0.02 inch (about 0.51 mm). Surgical needle N1 is illustrated as attached by eyelet threading to barbed suture S1. More particularly, surgical needle N1 is shown having suture S1 placed through eyelet E1, where the end of suture S1 is disposed in eyelet E1 at the end of the needle N1. In order to help hold suture S1 in place for suturing tissue, suture S1 may be looped more than once by standard procedures through eyelet E1 or suture S1 may be knotted by standard procedures.

FIG. 16B shows surgical needle N2 that is a straight elongated needle in the longitudinal direction and that is generally circular in cross section. Surgical needle N2 has pointed tip T2 for insertion into tissue and also has eyelet E2. Barbed suture S2 is a barbed suture including, but not limited to, any of the above-described barbed sutures. Additionally, surgical needle N2 has diameter D2 in the transverse direction, which is illustrated as a suitably thin diameter, such as about 0.032 inch (about 0.81 mm), but not as thin as diameter D1 of surgical needle N1. Surgical needle N2 is illustrated as attached by eyelet threading to barbed suture S2. More particularly, surgical needle N2 is shown having suture S2 placed through eyelet E2, where the end of suture S2 is disposed in eyelet E2 at the end of the needle N2. In order to help hold suture S2 in place for suturing tissue, suture S2 may be looped more than once by standard procedures through eyelet E2 or suture S1 may be knotted by standard procedures.

FIG. 16C shows surgical needle N3 that is a curved elongated needle in the longitudinal direction and that is generally circular in cross section. Surgical needle N3 has pointed tip T3 for insertion into tissue and also has eyelet E3. Barbed suture S3 is a barbed suture including, but not limited to, any of the above-described barbed sutures. Additionally, surgical needle N3 has diameter D3 in the transverse direction, which is illustrated as a relatively thin diameter, such as about 0.02 inch (about 0.51 mm). Surgical needle N3 is illustrated as attached by eyelet threading to barbed suture S3. More particularly, surgical needle N3 is shown having suture S3 placed through eyelet E3, where the end of suture S3 is disposed in eyelet E3, at the end of needle N3. In order to help hold suture S3 in place for suturing tissue, suture S3 may be looped more than once by standard procedures through eyelet E3 or suture S3 may be knotted.

FIG. 16D shows surgical needle N4 that is a curved elongated needle in the longitudinal direction and that is generally circular in cross section. Surgical needle N4 has pointed tip T4 for insertion into tissue and also has eyelet E4. Barbed suture S4 is a barbed suture including, but not limited to, any of the above-described barbed sutures. Additionally, surgical needle N4 has diameter D4 in the transverse direction, which is illustrated as a suitably thin diameter, such as about 0.032 inch (about 0.81 mm), but not as thin as diameter D3 of surgical needle N3. Surgical needle N4 is illustrated as attached by eyelet threading to barbed suture S4. More particularly, surgical needle N4 is shown having suture S4 placed through eyelet E4, at the end of needle N4. In order to help hold suture S4 in place for suturing tissue, suture S4 may be looped more than once by standard procedures through eyelet E4 or suture S4 may be knotted by standard procedures.

Needle tips T1, T2, T3, and T4 are schematically illustrated as pointed, but, as is well known, surgical needles come with various kinds of pointed tips, such as taper point, taper cutting, ball point, cutting edge, diamond point, thin line, and lancet point, and it is intended to include, but not be limited to, all such needle tips. Taper point, taper cutting, and diamond point are preferred needle tips for surgical needles used with barbed sutures.

As is well known in the art, needle diameter for surgical needles used with conventional (i.e., unbarbed) sutures is considered unimportant, and often very thick surgical needles are used with thin conventional sutures such that the ratio of surgical needle diameter to conventional suture diameter is 4:1 or even higher, such as 4.43:1.

However, with the surgical needle/barbed suture combination of the present invention (for either a straight needle or a curved needle), the thinner that the surgical needle is, then the more preferable that the surgical needle/barbed suture is, with the desired needle diameter being thinner and thinner as it approaches the barbed suture diameter, and it is possible that the needle diameter may be even thinner than the barbed suture diameter.

In general for the present invention, a relatively thin surgical needle attached to a barbed suture is more preferable for approximating tissue when stitching a wound closed than a relatively thick surgical needle threaded with a barbed suture. The reason is that the relatively thin surgical needle attached to a barbed suture allows for greater engagement of barbs in tissue, and therefore provides better closure strength to the approximated tissue that has been sutured to prevent the opposing sides of the closed wound from pulling apart, as compared to the closure strength provided to approximated tissue that has been sutured with the relatively thick surgical needle.

The most important feature for the combination of the surgical needle attached to the barbed suture is that the surgical needle diameter should be of sufficient width in order to make a hole or a channel in the end, such by drilling, to allow for insertion of the barbed suture into the hole or the channel. Nevertheless, as the surgical needle diameter increases, the surgical needle is still suitable as long as the ratio of the surgical needle diameter to the barbed suture diameter is about 3:1 or less.

Accordingly, a desirable ratio of surgical needle diameter to barbed suture diameter, for either a straight needle or a curved needle, is about 3:1 or less, more preferably about 2:1 or less, most preferably about 1.8:1 or less. Furthermore, particularly if channel needles are employed, the ratio of surgical needle diameter to barbed suture diameter may be as low as about 1:1 or less, or even lower, for instance, about 0.9:1 or less, or about 08:1 or less, or as low as about 0.5:1. It will be appreciated by the person of ordinary skill in the art that care should be taken with extremely thin needles so as to ameliorate the possibility of localized weakness, which may compromise tissue insertion.

Closure strength of thin surgical needles, both having a ratio of surgical needle diameter to barbed suture diameter suitable for the present invention, was tested as follows.

Various pieces of chamois leather (manufactured by U.S. Chamois of Florida) having a thickness of about 0.6 in (about 15.2 mm) were cut with a wound having a length of about 1.25 inch (about 32 mm).

A first specimen was made from a piece of chamois leather by stitching together the respective edges of the wound with a drilled end surgical needle (item no. 382077A purchased from Sulzle Company) which was swaged with a barbed suture. In other words, after insertion of the barbed suture into the needle hole, the needle was crimped about the hole to secure the barbed suture during stitching. After stitching closed the wound, the piece of chamois leather was cut to a rectangular shape of about 3 inches (about 76 mm) in length by about 1.25 inches (about 32 mm) in width, where the stitched wound was in the middle of the length and transverse the width. The needle was a taper point, curved surgical needle (⅜ of a circle), with a length of about 22 mm and a relatively thin diameter of about 0.020 inch (about 0.51 mm).

Then, using the same stitching method, a second specimen was made from another piece of chamois leather by stitching together the respective edges of the wound, using a drilled end surgical needle (item no. 383271A purchased from Sulzle Company) swaged with the same kind of barbed suture, i.e., the surgical needle was crimped about the needle hole, after insertion of the barbed suture into the hole, to secure the barbed suture during stitching. For the second specimen, the needle was a taper point curved surgical needle (⅜ of a circle) with a length of about 22 mm and a suitable thin diameter of about 0.032 inch (about 0.81 mm), although not as thin as the diameter of the needle used for first specimen.

Each barbed suture for each specimen was a bi-directional, twist cut multiple spiral, polydioxanone barbed suture like suture 70 in FIG. 6A, except that each barbed suture had a diameter of about 0.0115 inch (about 0.291 mm, which is slightly larger than the USP requirement for a size 3-0 synthetic absorbable suture), instead of a suture diameter of about 0.018 inch (about 0.457 mm).

Both the first and the second specimens of stitched chamois cloth were tested for closure strength using a Test Resources Universal Tester, Model 200Q. Each specimen was gripped by two respective serrated jaws. Then, each specimen was pulled longitudinally at a rate of about 10 inches per minute (about 254 mm per minute) until complete rupture. The peak load in pounds reached before complete wound disruption was recorded as the closure strength. The results were that the first specimen (which was sutured with the needle that had a relatively thin diameter of about 0.020 inch, about 0.51 mm) took 5.88 pounds until wound disruption occurred and the specimen pulled apart back into 2 pieces, whereas the second specimen (which was stitched with the needle that had a suitably thin diameter of about 0.032 inch, about 0.81 mm, but not as thin as the needle for the first specimen) took only 2.88 pounds until the wound disruption and the specimen pulled apart back into 2 pieces.

The results are summarized in Table 13A below.

TABLE 13A (Chamois Cloth Closure Strength)

| Specimen | Needle Diameter | Barbed Suture Diameter | Ratio* | Pounds to Rupture |
|---|---|---|---|---|
| First | 0.020 inch | 0.0115 inch | 1.74 | 5.88 |
| Second | 0.032 inch | 0.0115 inch | 2.78 | 2.88 |

*Ratio of surgical needle diameter to barbed suture diameter.

Also, various pieces of rat skin were cut and stitched for testing of more surgical needles swaged with barbed sutures as follows.

Three freshly killed Sprague-Dawley rats, each about 600 to 700 g, were used. Two full-thickness skin incisions were made on the back of each rat to create wounds. Each wound was about 4 cm in length and parallel to the spine.

For each rat, one of the two wounds was closed with a drilled end, curved surgical needle that was a Sulzle item no. 382273A, which was ⅜ circle. The needle had a length of 18 mm and a diameter of about 0.022 inch (about 0.56 mm). Also, the needle had a taper point needle tip where the needle tip had been ground to a 3-facet cut to approximate a taper cutting needle tip to facilitate penetration of rat tissue. The needle was swaged to a barbed suture.

The other of the two wounds was closed using the same suturing technique, but with a drilled end, curved surgical needle that was a Sulzle item no. 832679A, which was ⅜ circle. The needle had a length of about 18 mm and a diameter of about 0.026 inch (about 0.66 mm). Also, the needle had a diamond point needle tip. The needle was swaged to a barbed suture.

Each barbed suture for each specimen was a bi-directional, twist cut multiple spiral, polydioxanone barbed suture like suture 70 in FIG. 6A, except that each barbed suture had a diameter of about 0.015 inch (about 0.381 mm, which is slightly larger than the USP requirement for a size 2-0 synthetic absorbable suture), instead of a suture diameter of about 0.018 inch (about 0.457 mm).

For each stitched wound, a tissue specimen that was approximately a square measuring about 4 cm×about 4 cm, with the stitched wound in the middle paralleling two opposing tissue edges, was retrieved for closure strength testing.

The force to open each wound was determined using a Test Resources Universal Tester, Model 200Q. For each tissue specimen, the two edges paralleling each stitched wound were mounted in the two respective serrated jaws of the tester.

Then, each specimen was pulled longitudinally at a rate of about 2 inches per minute (about 51 mm per minute) until complete rupture occurred. The maximum force encountered before complete wound disruption was recorded as the closure strength.

The results were averaged from the first set of three wounds closed with a needle having a diameter of about 0.022 inch (about 0.56 mm) and swaged to a barbed suture. Also, the results were averaged from the second set of three wounds closed with a needle having a diameter of about 0.026 inch (about 0.66 mm) and swaged to a barbed suture.

The results are summarized in Table 13B below.

TABLE 13B (Rat Skin Closure Strength)

| Specimens | Needle Diameter | Barbed Suture Diameter | Ratio* | Average of 3 Wounds Pounds to Rupture |
|---|---|---|---|---|
| First set of 3 | 0.022 inch | 0.015 inch | 1.47 | 11.9 |
| Second set of 3 | 0.026 inch | 0.015 inch | 1.73 | 8.1 |

*Ratio of surgical needle diameter to barbed suture diameter.

Thus, the lower the ratio of surgical needle diameter to barbed suture diameter, then the better the closure strength when suturing a wound closed with a surgical needle attached to a barbed suture. In general, the thinner the surgical needle, the better the closure strength, particularly for delicate tissues; however, for tough tissues, such as muscle and bowel, thicker needles are preferred. Thus, what is important, regardless of whether the needle is thick or thin or somewhere in the middle, is that the ratio of surgical needle diameter to barbed suture diameter should be about 3:1 or less, more preferably about 2:1 or less.

Although the present invention has been shown and described in detail with regard to only a few exemplary embodiments of the invention, it should be understood by those skilled in the art that it is not intended to limit the invention to the specific embodiments disclosed. Various modifications, omissions, and additions may be made to the disclosed embodiments without materially departing from the novel teachings and advantages of the invention, particularly in light of the foregoing teachings. For instance, the barbed suture of the present invention can be used alone or with other closure methods, such as staples and/or skin adhesives, to aid in holding the position of the tissue. Accordingly, it is intended to cover all such modifications, omissions, additions, and equivalents as may be included within the spirit and scope of the invention as defined by the following claims.

What is claimed is:

1. A unidirectional barbed suture for connecting human or animal tissue, said suture comprising:
    an elongated body having a generally circular cross section, a longitudinal axis, a cross-sectional distance (SD), a first end and a second end, where a needle having a needle diameter (ND) is attached to the first end; and
    a plurality of cuts in the elongated body that provide for a plurality of barbs projecting from the body towards the second end; wherein the barbs are staggered along the body in three sets with 120 degree radial spacing between any two sets; and a plurality of barbs comprising a configuration wherein a ratio of a barb cut depth (D) to the (SD) is about 0.05 to about 0.6.

2. The barbed suture of claim 1 wherein the ratio of the D to the SD is about 0.1 to 0.55.

3. The barbed suture of claim 2 wherein the ratio of the ND to the SD is less than 1.8.

4. The barbed suture of claim 1 wherein the ratio of the D to the SD is about 0.2 to 0.5.

5. The barbed suture of claim 4 wherein a ratio of a longitudinal distance between adjacent barbs (P) to the SD is about 1.0 to 3.5.

6. The barbed suture of claim 4 wherein a ratio of a barb cut length (L) to the SD is about 0.8 to 1.5.

7. The barbed suture of claim 1 wherein a ratio of a longitudinal distance between adjacent barbs (P) to the SD is about 0.1 to 6.0.

8. The barbed suture of claim 1 wherein a ratio of a longitudinal distance between adjacent barbs (P) to the SD is about 0.5 to 4.5.

9. The barbed suture of claim 1 wherein a ratio of a longitudinal distance between adjacent barbs (P) to the SD is about 1.0 to 3.5.

10. The barbed suture of claim 1 wherein a ratio of a barb cut length (L) to the SD is about 0.2 to 2.

11. The barbed suture of claim 1 wherein a ratio of a barb cut length (L) to the SD is about 0.4 to 1.7.

12. The barbed suture of claim 1 wherein a ratio of a barb cut length (L) to the SD is about 0.8 to 1.5.

13. The barbed suture of claim 1 wherein a ratio of the ND to the SD is less than 3.

14. The barbed suture of claim 1 wherein a ratio of the ND to the SD is less than 2.

15. The barbed suture of claim 1 wherein the ratio of the ND to the SD is less than 1.8.

16. The suture of claim 1 having a size of 0, 2-0 or 3-0.

17. The suture of claim 1 wherein the elongated body is a monofilament.

18. The suture of claim 1 formed from components comprising a synthetic biodegradable polymer.

19. The barbed suture of claim 1 wherein the needle is curved.

* * * * *